United States Patent
Wang et al.

(10) Patent No.: US 9,859,509 B2
(45) Date of Patent: Jan. 2, 2018

(54) THIOXANTHONE AROMATIC AMINE COMPOUND AND ORGANIC LIGHT EMITTING DEVICE USING THE SAME

(71) Applicant: Shenzhen China Star Optoelectronics Technology Co., Ltd., Shenzhen (CN)

(72) Inventors: Yifan Wang, Shenzhen (CN); Qinghua Zou, Shenzhen (CN); Shijian Su, Shenzhen (CN); Kunkun Liu, Shenzhen (CN); Zhiheng Wang, Shenzhen (CN); Yunchuan Li, Shenzhen (CN)

(73) Assignee: SHENZHEN CHINA STAR OPTOELECTRONICS TECHNOLOGY CO., LTD., Shenzhen, Guangdong (CN)

( * ) Notice: Subject to any disclaimer, the term of this patent is extended or adjusted under 35 U.S.C. 154(b) by 85 days.

(21) Appl. No.: 14/778,077

(22) PCT Filed: Apr. 22, 2015

(86) PCT No.: PCT/CN2015/077152
§ 371 (c)(1),
(2) Date: Sep. 17, 2015

(87) PCT Pub. No.: WO2016/149975
PCT Pub. Date: Sep. 29, 2016

(65) Prior Publication Data
US 2016/0351831 A1     Dec. 1, 2016

(30) Foreign Application Priority Data
Mar. 26, 2015    (CN) .......................... 2015 1 0137655

(51) Int. Cl.
*H01L 29/08*     (2006.01)
*H01L 51/00*     (2006.01)
(Continued)

(52) U.S. Cl.
CPC ........ *H01L 51/0074* (2013.01); *C07D 335/16* (2013.01); *C07D 409/04* (2013.01);
(Continued)

(58) Field of Classification Search
CPC ................................................... H01L 51/0074
(Continued)

(56) References Cited

U.S. PATENT DOCUMENTS

| | | | |
|---|---|---|---|
| 8,952,367 B2 * | 2/2015 | Kamatani | C07D 335/16 257/40 |
| 2013/0221340 A1 * | 8/2013 | Kamatani | C07D 335/16 257/40 |
| 2014/0167001 A1 * | 6/2014 | Lee | C09K 11/06 257/40 |

FOREIGN PATENT DOCUMENTS

| | | | | |
|---|---|---|---|---|
| CN | 103189368 A | | 7/2013 | |
| CN | WO 2014071836 A1 * | | 5/2014 | .......... H01L 51/005 |

(Continued)

*Primary Examiner* — Ajay K Arora
(74) *Attorney, Agent, or Firm* — Leong C. Lei

(57) ABSTRACT

The invention provides a thioxanthone aromatic amine compound and an organic light emitting device using the compound. The thioxanthone aromatic amine compound includes a compound expressed by formula (I) or formula (II):

(I)

(Continued)

-continued (II)

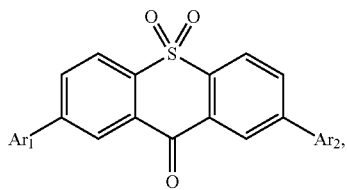

where Ar$_1$ and Ar$_2$ each are selected from ammonia compounds with structures respectively expressed by formula (III) to formula (VII), or hydrogen atom, (III)

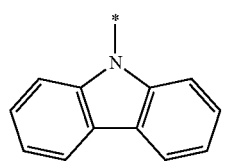

(IV)

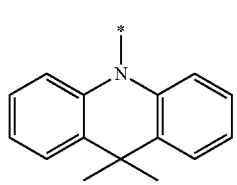

(V)

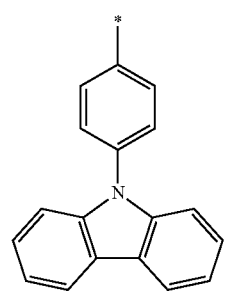

(VI)

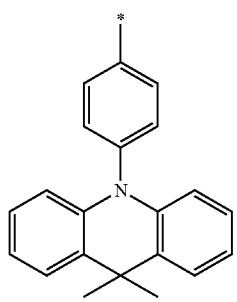

-continued (VII)

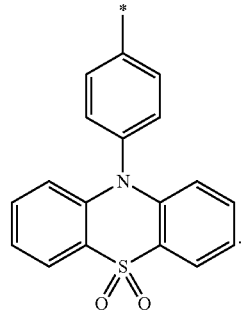

thioxanthone aromatic amine compound of the invention has single structure, determinate molecular weight, and has better solubility and film-forming property, and also has low biochemical temperature and decomposition temperature, and stable film morphology.

8 Claims, 11 Drawing Sheets

(51) Int. Cl.
*C07D 335/16* (2006.01)
*C07D 409/04* (2006.01)
*C07D 409/10* (2006.01)
*C07D 409/14* (2006.01)
*C07D 417/10* (2006.01)
*C07D 417/14* (2006.01)
*C09K 11/06* (2006.01)
*H01L 51/50* (2006.01)

(52) U.S. Cl.
CPC ......... *C07D 409/10* (2013.01); *C07D 409/14* (2013.01); *C07D 417/10* (2013.01); *C07D 417/14* (2013.01); *C09K 11/06* (2013.01); *H01L 51/0059* (2013.01); *H01L 51/0067* (2013.01); *H01L 51/0071* (2013.01); *H01L 51/0072* (2013.01); *H01L 51/5004* (2013.01); *C09K 2211/1007* (2013.01); *C09K 2211/1029* (2013.01); *C09K 2211/1037* (2013.01); *C09K 2211/1092* (2013.01); *H01L 51/5012* (2013.01); *H01L 51/5056* (2013.01); *H01L 51/5072* (2013.01); *H01L 51/5088* (2013.01); *H01L 2251/558* (2013.01)

(58) Field of Classification Search
USPC .......................................................... 257/40
See application file for complete search history.

(56) References Cited

FOREIGN PATENT DOCUMENTS

CN          104218157 A    12/2014
WO     WO2014071836 A1     5/2014

\* cited by examiner

THIOXANTHONE AROMATIC AMINE COMPOUND AND ORGANIC LIGHT EMITTING DEVICE USING THE SAME

TECHNICAL FIELD

The invention relates to the technical field of evaporation material of organic light emitting device, and particularly to a thioxanthone aromatic amine compound and an organic light emitting device using the same.

DESCRIPTION OF RELATED ART

An organic light emitting diode (OLED) display device is a highly promising flat panel display technology, it not only has a very excellent display performance, but also has self-luminous, simple structure, ultra-thin, fast response speed, wide viewing angle, low power consumption and realizable flexible display and other characteristics, so that it is known as the "Dream Monitor", and moreover owing to its investment in production facilities being far less than that of liquid crystal display (LCD) device, it is favored by major display manufacturers and has become the main force of third-generation display devices in the field of display technology.

The OLED display device uses an organic light emitting device to emit light, so that it is important to improve the efficiency and life of the organic light emitting device. Nowadays, the OLED has been made considerable progress; we can achieve a white-light device with simple device structure and high efficiency by fluorescent and phosphorescent hybridization. However, the efficiency of such fluorescent and phosphorescent hybridization device is largely dependent on the efficiency of the fluorescent, and therefore the development of high efficient fluorescent material still has an important significance. Compared with polymers, light-emitting small molecules can achieve higher duration efficiency due to simple preparation process, stable structures and purifiable and therefore can obtain commercial applications. Methods of making/preparing multilayer devices by using small molecules to perform evaporation or solution processing have gotten great concern and tremendous progress.

Due to single structure, determinate molecular weight and simple purification process, evaporation-type organic small molecules based on thioxanthone aromatic amine can be used in organic light emitting devices which include organic light-emitting diodes, and can use the valence state change of sulfur atom to further improve the balance carrier's ability of the material, so that the efficiency and stability of the device can be improved. However, so far, skeletons of most of evaporation molecules used in the organic light emitting devices use sulfur dibenzofuran, phosphorous oxide, triphenylamine and other units as core, however, an organic light-emitting small molecule using thioxanthone as core is rarely reported.

SUMMARY

An objective of the invention is to provide a thioxanthone aromatic amine compound, which has single structure, determinate molecular weight and better solubility and film-forming property.

Another objective of the invention is to provide an organic light emitting device, which has high luminous efficiency and stability.

In order to achieve the above mentioned objectives, the invention provides a thioxanthone aromatic amine compound including a compound expressed by the following formula (I) or formula (II):

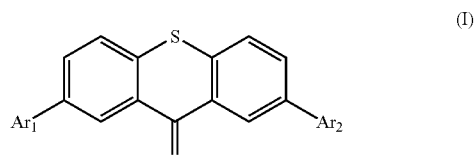

(I)

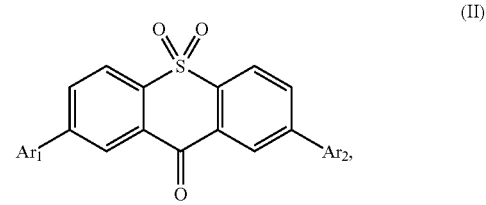

(II)

where $Ar_1$ and $Ar_2$ each are selected from ammonia compounds with structures respectively expressed by the following formula (III) to formula (VII) or hydrogen atom,

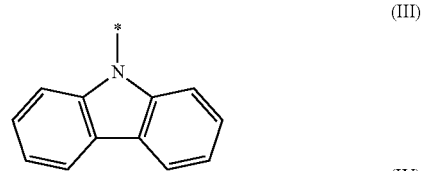

(III)

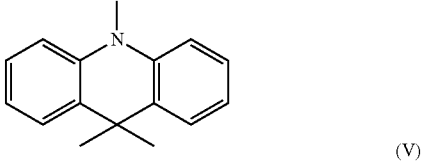

(IV)

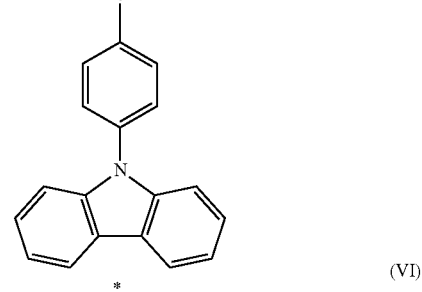

(V)

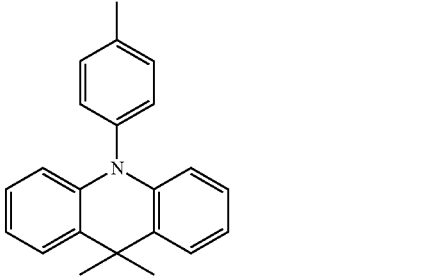

(VI)

-continued (VII)

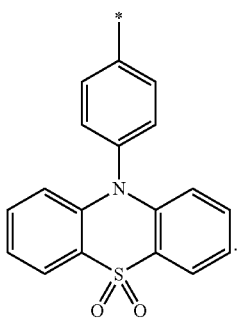

The Ar$_1$ and the Ar$_2$ each are selected from the ammonia compounds with structures respectively expressed by the formula (III) to formula (VII), and the Ar$_1$ and the Ar$_2$ having the same structure.

The thioxanthone aromatic amine compound includes compounds P1, P2, P5, P6, P9, P10, P11, P12, P13, P14, P21, P22, P23, P24, P25, P26, P33, P34, P35, P36, P37 and P38 respectively having structural formulas as follows:

P1

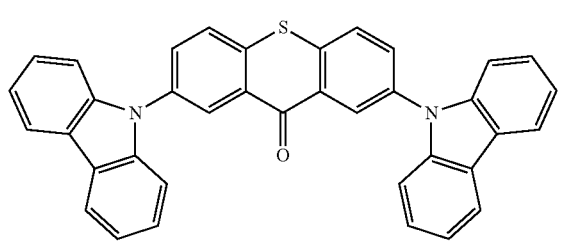

P2

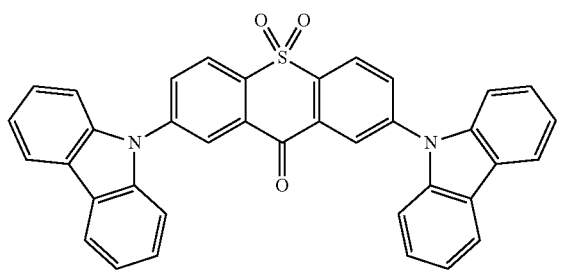

P5

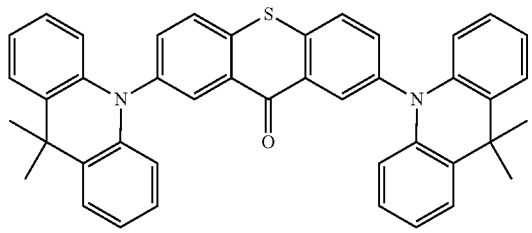

P6

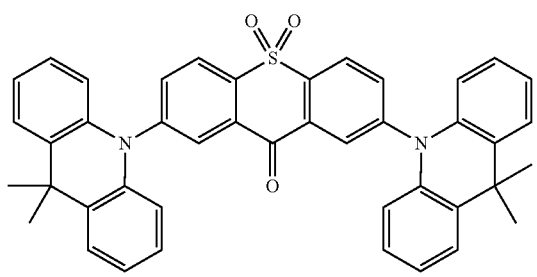

P9

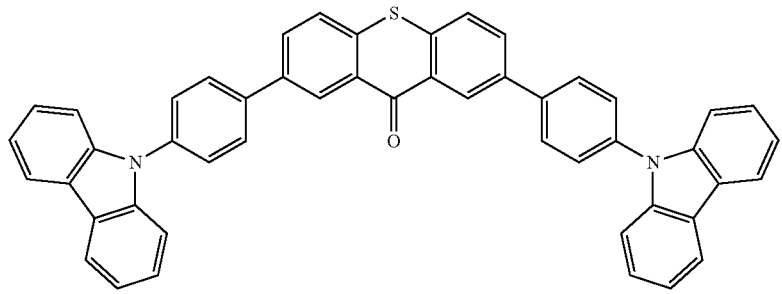

P10

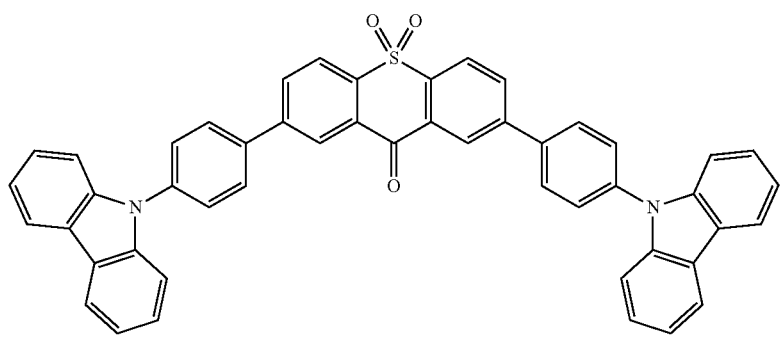

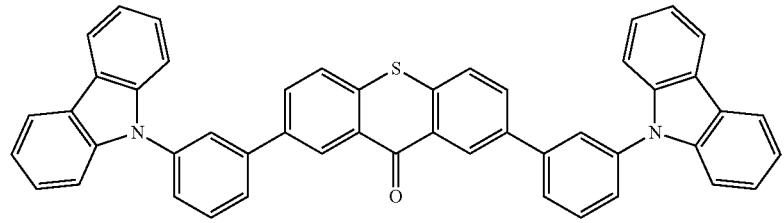
P11
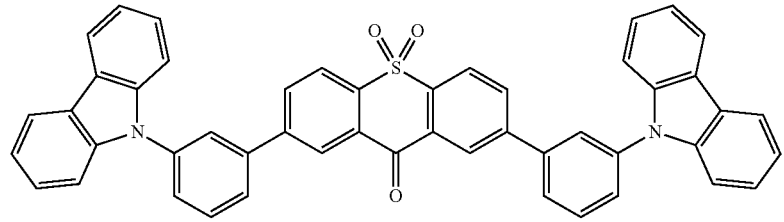
P12
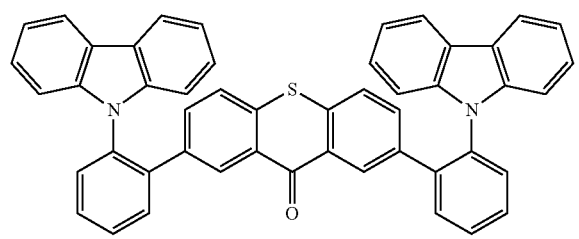
P13
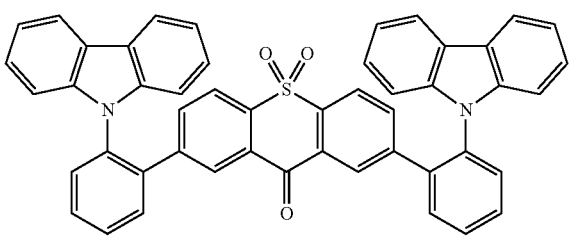
P14
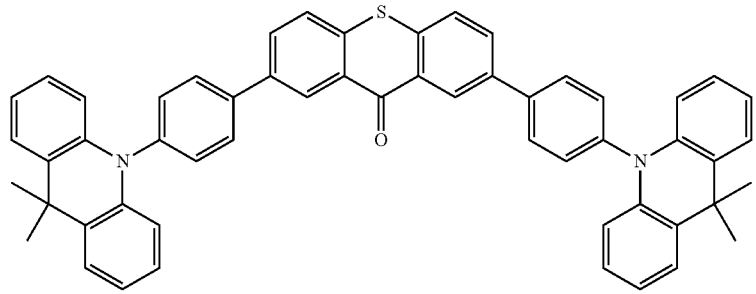
P21
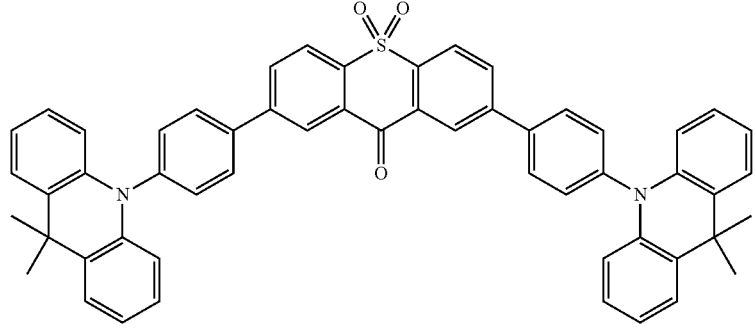
P22
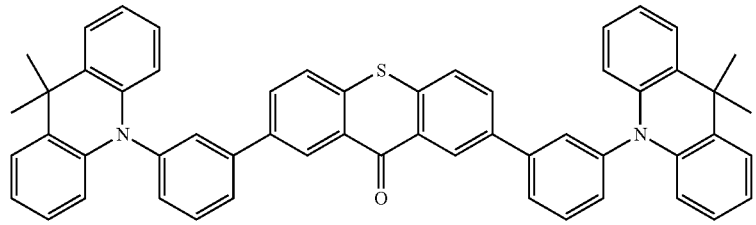
P23

-continued
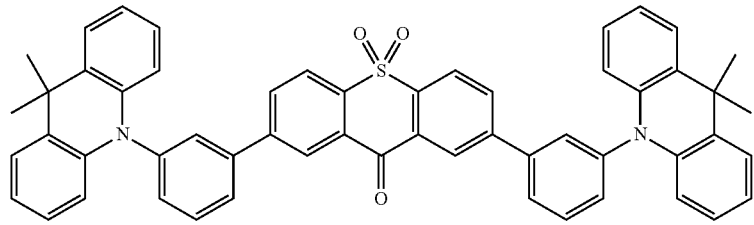
P24
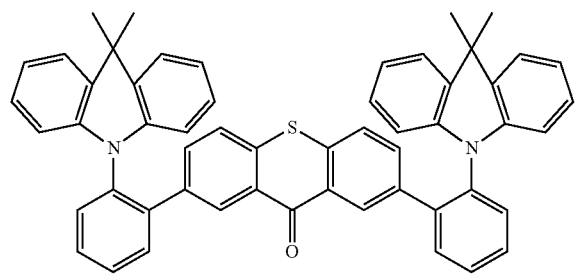
P25
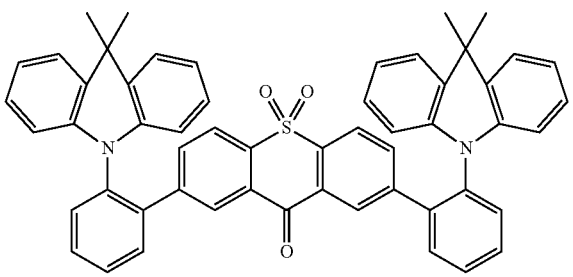
P26
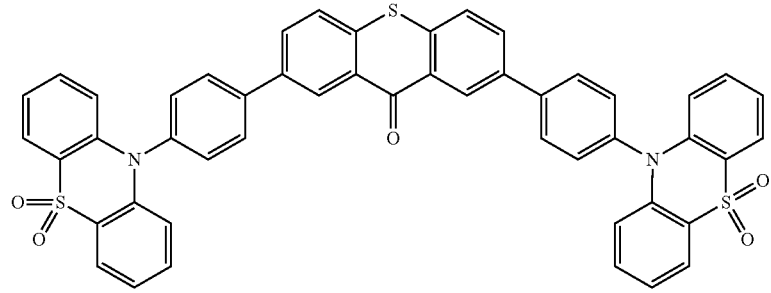
P33
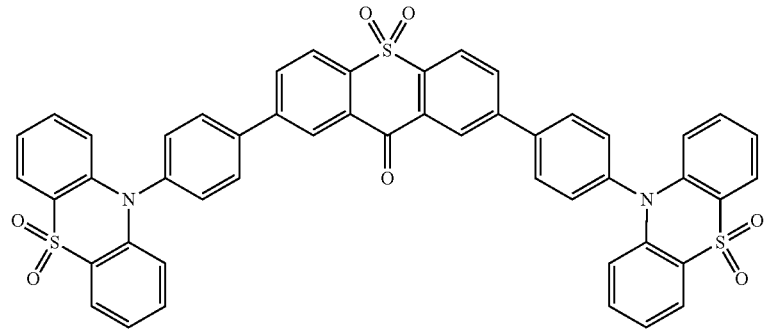
P34
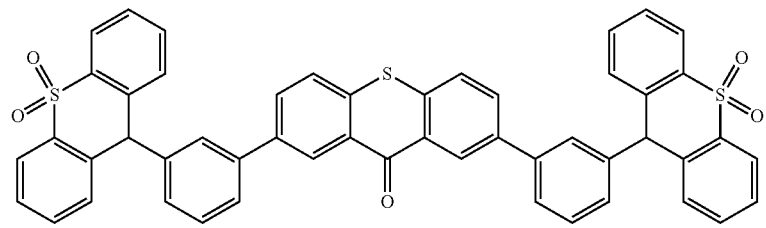
P35
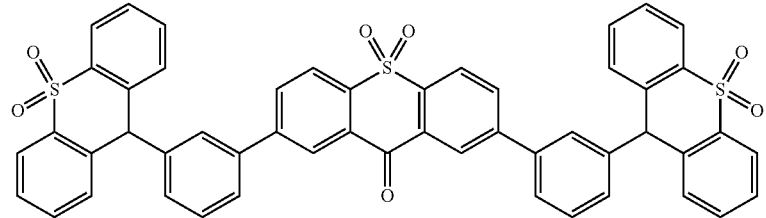
P36

P37

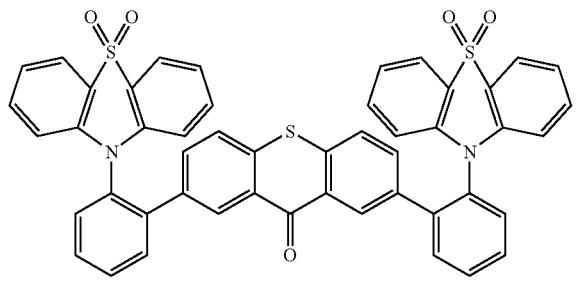

P38

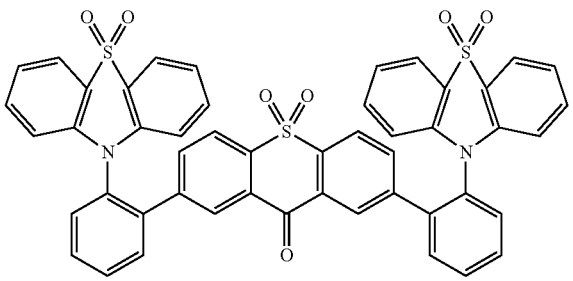

The Ar$_1$ and the Ar$_2$ each are selected from the ammonia compounds with the structures respectively expressed by the formula (III) to the formula (VII), and the Ar$_1$ and the Ar$_2$ having different structures.

The Ar$_1$ is hydrogen atom, the Ar$_2$ is selected from the ammonia compounds with the structures respectively expressed by the formula (III) to the formula (VII).

The thioxanthone aromatic amine compound includes compounds P3, P4, P7, P8, P15, P16, P17, P18, P19, P20, P27, P28, P29, P30, P31, P32, P39, P40, P41, P42, P43 and P44 respectively having structural formulas as follows:

P3

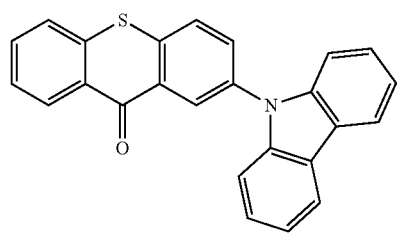

P4

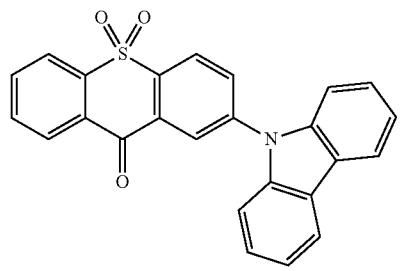

P7

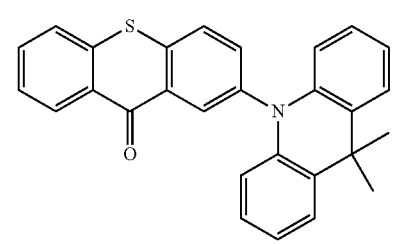

P8

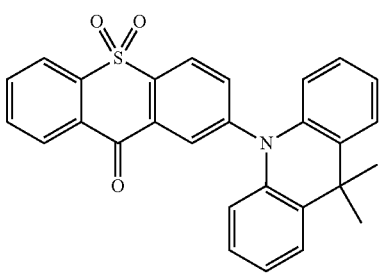

P15

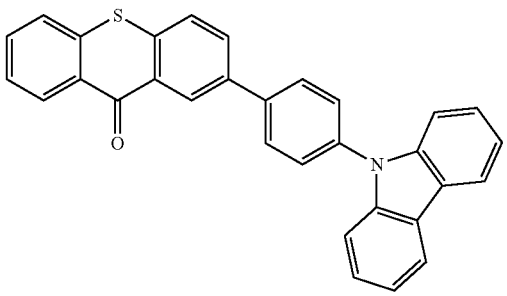

P16

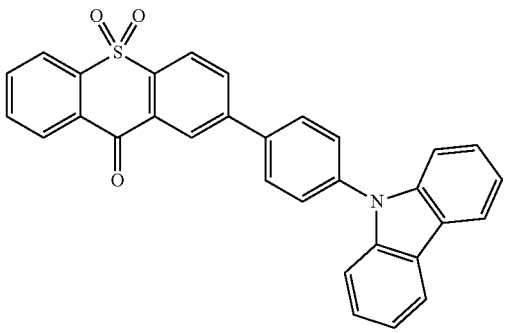

P17

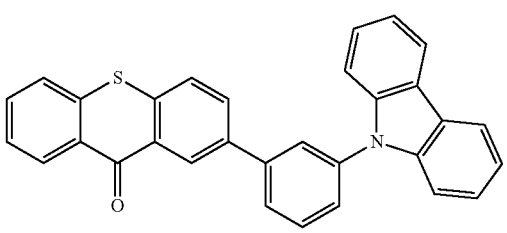

P18
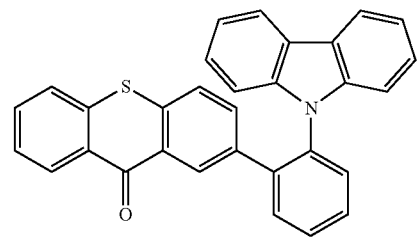
P19
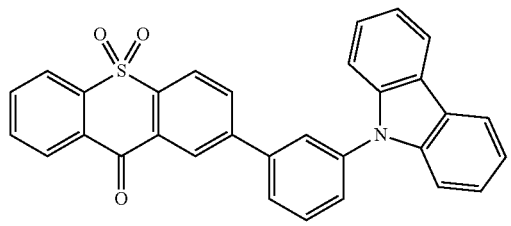
P20
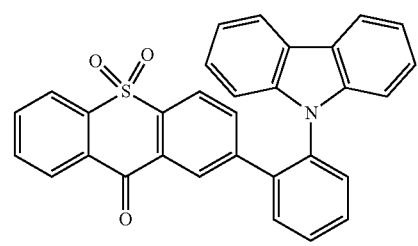
P27
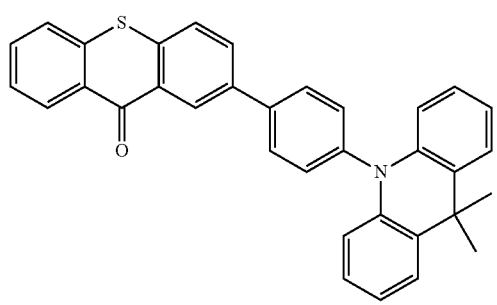
P28
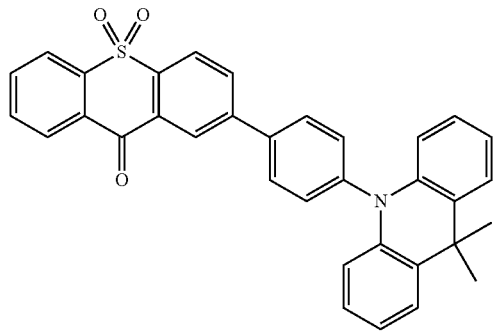
P29
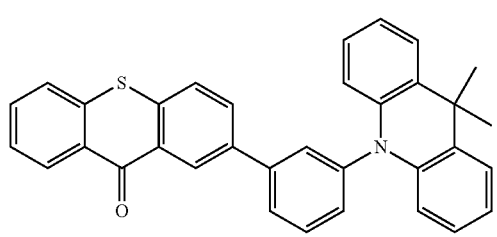
P30
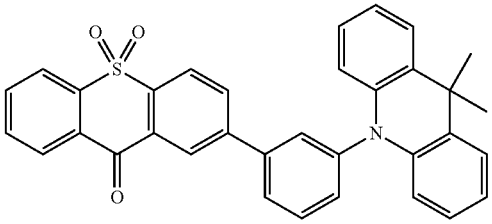
P31
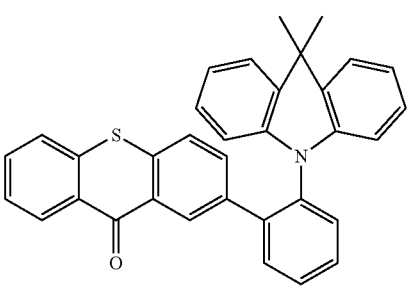
P32
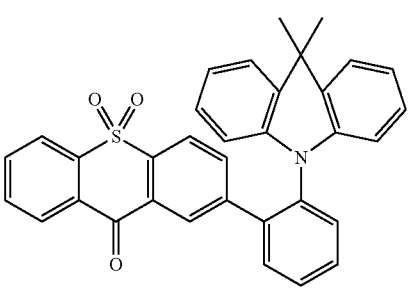
P39
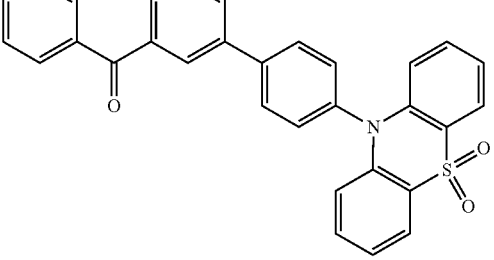
P40
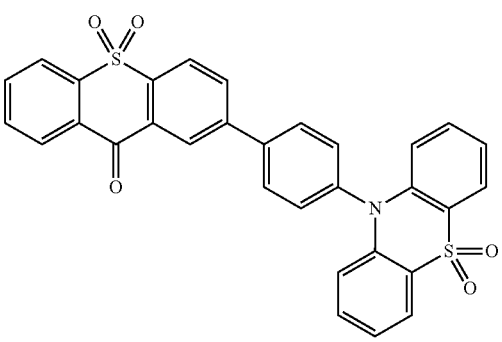

-continued

P41
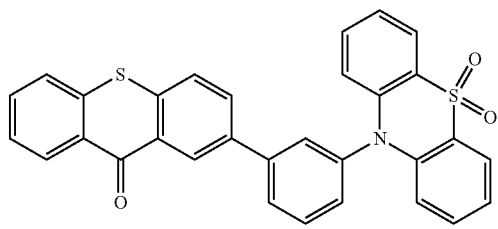

P42
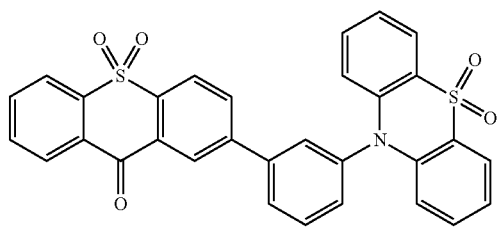

P43
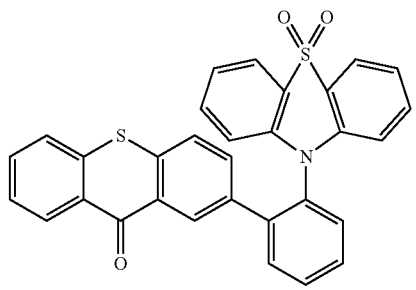

P44
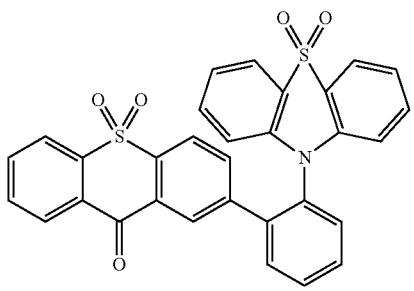

The invention further provides an organic light emitting device including a substrate, an anode formed on the substrate, a hole injection layer formed on the anode, a hole transport layer formed on the hole injection layer, a plurality of light-emitting layers formed on the hole transport layer, an electron transport layer formed on the plurality of light-emitting layers, and a cathode formed on the electron transport layer. A material of the plurality of the light-emitting layers is one or more thioxanthone aromatic amine compounds as above mentioned.

A material of the anode is indium tin oxide, an electron injection layer is provided between the cathode and the electron transport layer, a material of the cathode is aluminum, and a material of the electron injection layer is lithium fluoride.

A thickness of the anode is 95 nm, a thickness of the hole injection layer is 5 nm, a thickness of the hole transport layer is 20 nm, a thickness of the light-emitting layers is 35 nm, a thickness of the electron transport layer is 55 nm, a thickness of the cathode is greater than 80 nm, and a thickness of the electron injection layer is 1 nm.

A material of the hole injection layer is 2,3,6,7,10,11-hexacyano-1,4,5,8,9,12-hexaazatriphenylenehexacabonitrile (HAT-CN) whose structural formula is

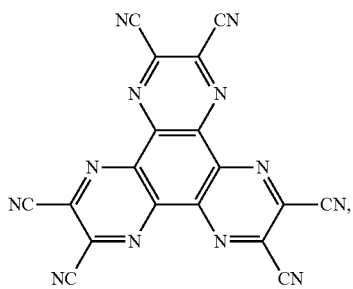 [SMILES: N#Cc1nc2c3nc(C#N)c(C#N)nc3c3nc(C#N)c(C#N)nc3c2nc1C#N]

a material of the hole transport layer is 4-(2-thiazolylazo)-phenyl-2-glycine (TAPC) whose structural formula is

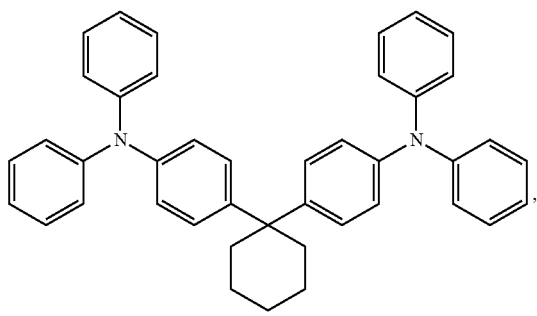 [SMILES: c1ccc(N(c2ccccc2)c2ccc(C3(c4ccc(N(c5ccccc5)c5ccccc5)cc4)CCCCC3)cc2)cc1]

a material of the light-emitting layers is 1,3-di-carbazolyl benzene (mCP) doped with a thioxanthone aromatic amine compound P2, a structural formula of the 1,3-di-carbazolyl benzene (mCP) is

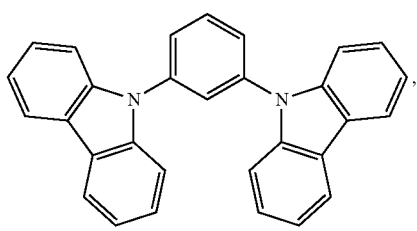 [SMILES: c1cc(-n2c3ccccc3c3ccccc32)cc(-n2c3ccccc3c3ccccc32)c1]

a structural formula of the thioxanthone aromatic amine compound P2 is

P2
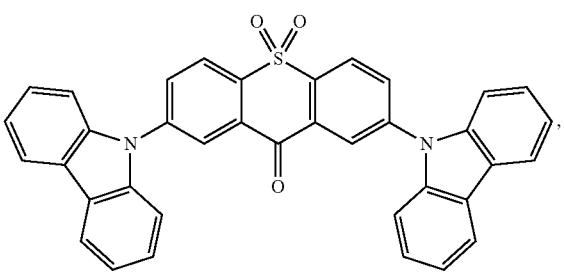

a material of the electron transport layer is 1,3,5-tri[(3-pyridyl)-3-phenyl] benzene (TmPyPB) whose structural formula is

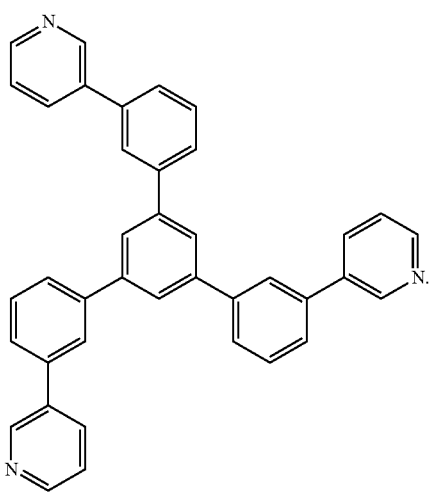 [SMILES: c1cncc(-c2cccc(-c3cc(-c4cccc(-c5cccnc5)c4)cc(-c4cccc(-c5cccnc5)c4)c3)c2)c1]

The invention further provides an organic light emitting device including a substrate, an anode formed on the substrate, a hole injection layer formed on the anode, a hole transport layer formed on the hole injection layer, a plurality of light-emitting layers formed on the hole transport layer, an electron transport layer formed on the plurality of light-emitting layers, and a cathode formed on the electron transport layer. A material of the plurality of light-emitting layers is one or more the thioxanthone aromatic amine compounds as claimed in claim 1;

wherein, a material of the anode is indium tin oxide, an electron injection layer is provided between the cathode and the electron transport layer, material of the cathode is aluminum, a material of the electron injection layer is lithium fluoride;

wherein, a material of the hole injection layer is 2,3,6,7,10,11-hexacyano-1,4,5,8,9,12-hexaazatriphenylenehexacabonitrile (HAT-CN) whose structural formula is

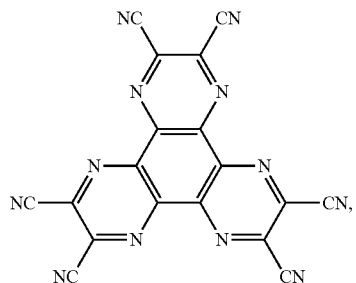 [SMILES: N#Cc1nc2c3nc(C#N)c(C#N)nc3c3nc(C#N)c(C#N)nc3c2nc1C#N]

a material of the hole transport layer is 4-(2-thiazolylazo)-phenyl-2-glycine (TAPC) whose structural formula is

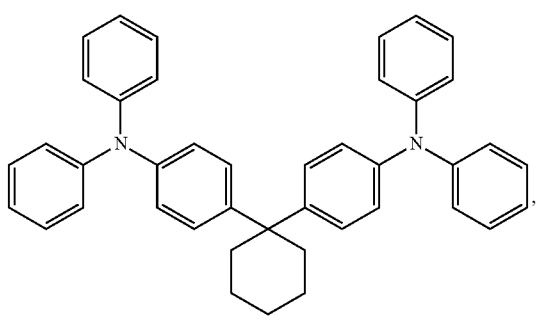 [SMILES: c1ccc(N(c2ccccc2)c2ccc(C3(c4ccc(N(c5ccccc5)c5ccccc5)cc4)CCCCC3)cc2)cc1]

a material of the light-emitting layers is 1,3-di-carbazolyl benzene (mCP) doped with a thioxanthone-aromatic amine compound P2, a structural formula of the 1,3-di-carbazolyl benzene (mCP) is

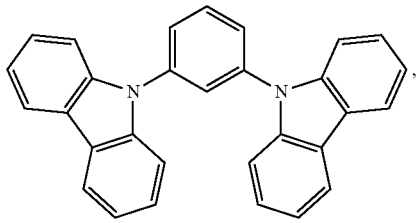 [SMILES: c1cc(-n2c3ccccc3c3ccccc32)cc(-n2c3ccccc3c3ccccc32)c1]

a structural formula of the thioxanthone aromatic amine compound P2 is

P2

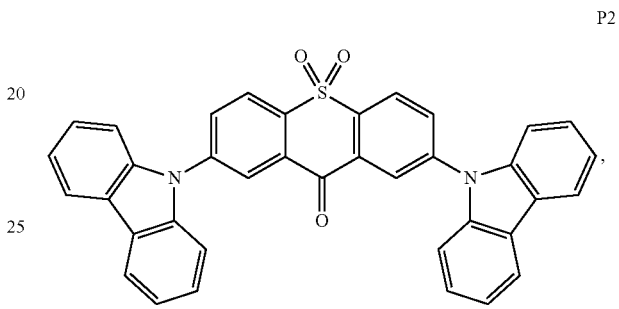

a material of the electron transport layer is 1,3,5-tri[(3-pyridyl)-3-phenyl] benzene (TmPyPB) whose structural formula is

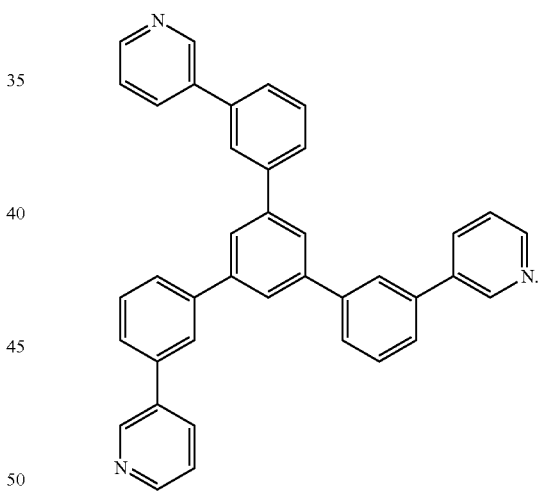

Beneficial effects of the invention are that: the thioxanthone aromatic amine compound of the invention has single structure, determinate molecular weight, and has better solubility and film-forming property, and also has low biochemical temperature and decomposition temperature, and stable film morphology; conjugation length and light-emitting color of such material can be adjusted by changing connected chemical structures, physical characteristics and performance of photoelectric devices based on the thioxanthone aromatic amine compound can be further improved by changing modified groups contained on the aromatic structure. The organic light emitting device of the invention can achieve high luminous efficiency and stability owing to the material of light-emitting layer thereof adopting the thioxanthone aromatic amine compound.

In order to further understand features and technical contents of the invention, please refer to following detailed description and accompanying drawings of the invention. The drawings only are used for reference and description and are not intended to limit the invention.

BRIEF DESCRIPTION OF THE DRAWINGS

In the following, with reference to accompanying drawings, concrete embodiments of the invention will be described in detail to make technical solutions and other beneficial effects of the invention more clear. In the drawings.

DETAILED DESCRIPTION OF EMBODIMENTS

Figure 1:
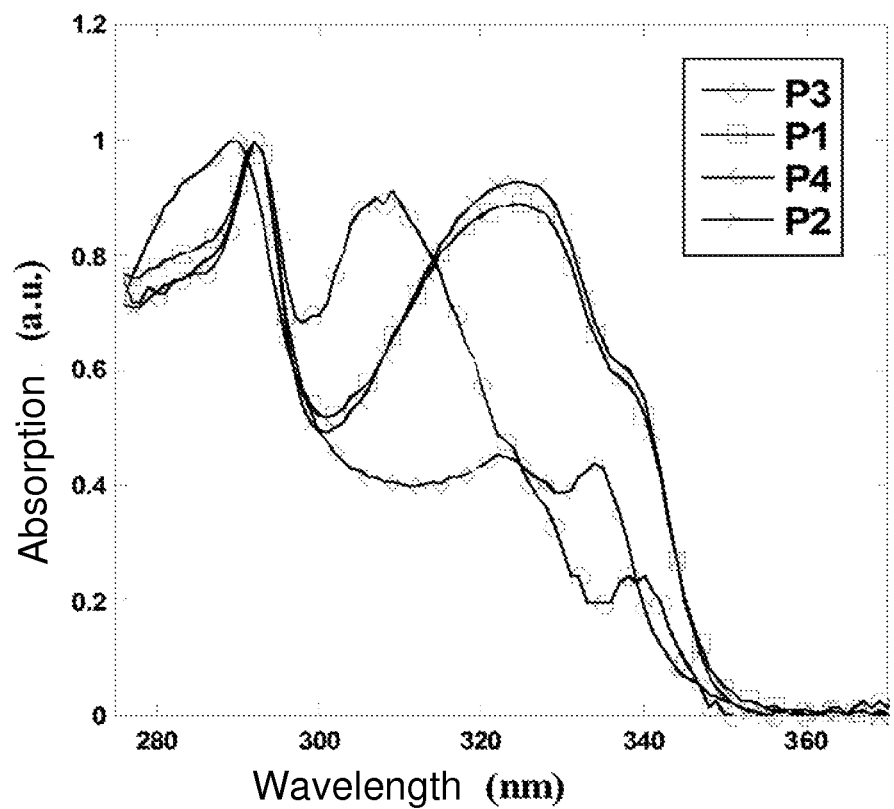
FIG. 1 is an absorption spectra view of thioxanthone aromatic amine compounds P1, P2, P3, P4 in a dichloromethane solution of the invention.

In order to further illustrate technical solutions and effects of the invention, preferred embodiments of the invention with reference to accompanying drawings will be described below in detail.

First, the invention provides a thioxanthone aromatic amine compound including a compound with a general structural formula expressed as formula (I) or formula (II):

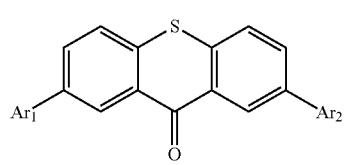

(I)

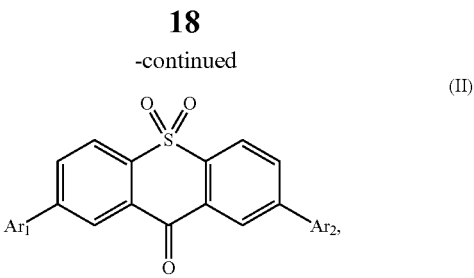

(II)

where $Ar_1$ and $Ar_2$ each are selected from ammonia compounds with structures expressed by formula (I) to formula (V) or hydrogen atom,

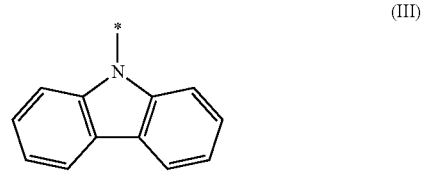

(III)

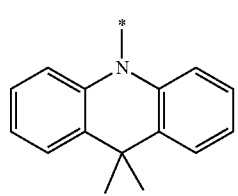

(IV)

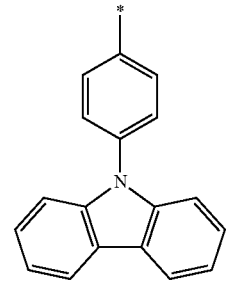

(V)

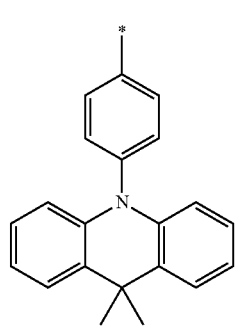

(VI)

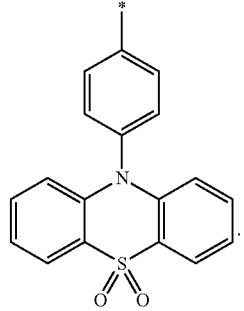

(VII)

Specifically, the $Ar_1$ and the $Ar_2$ each may be selected from the ammonia compounds with structures expressed by the formula (III) to formula (VII), and the $Ar_1$ and the $Ar_2$ having the same structure. At this time, the thioxanthone aromatic amine compounds include compounds P3, P4, P7, P8, P15, P16, P17, P18, P19, P20, P27, P28, P29, P30, P31, P32, P39, P40, P41, P42, P43 and P44, their structural formulas respectively are as follows:

P1
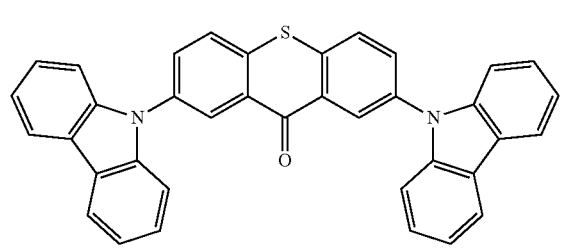

P2
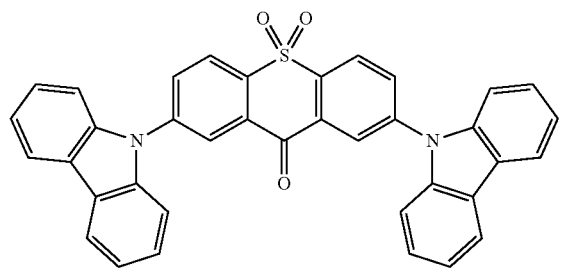

P5
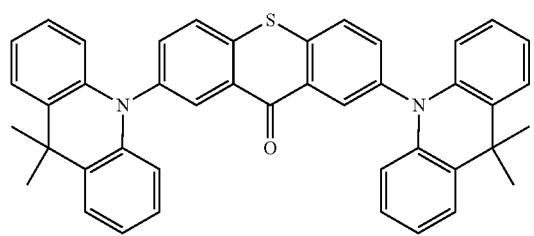

P6
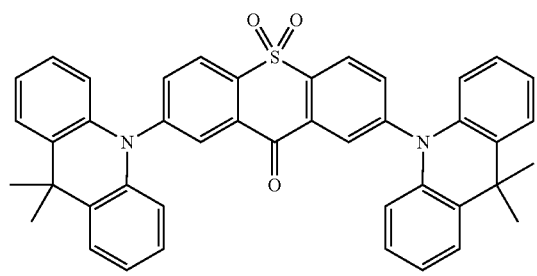

P9
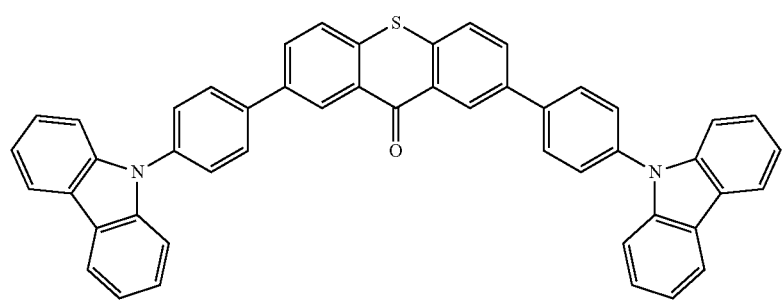

P10
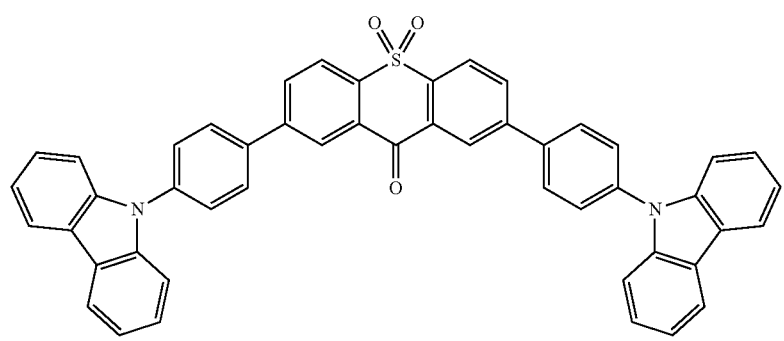

P11
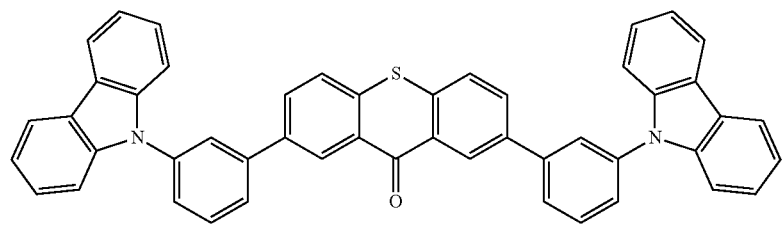

-continued
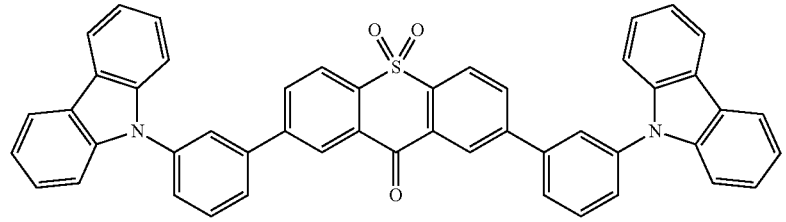
P12
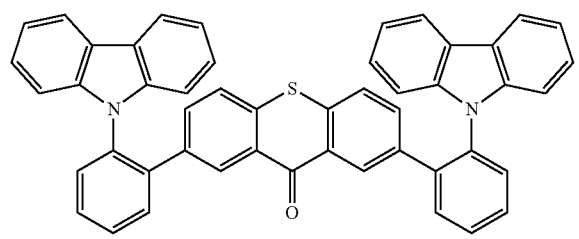
P13
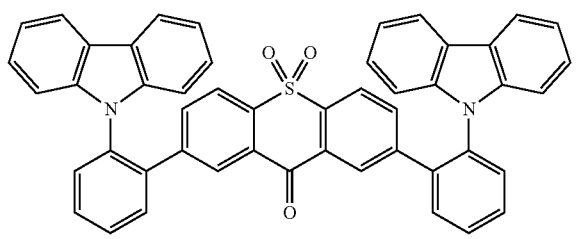
P14
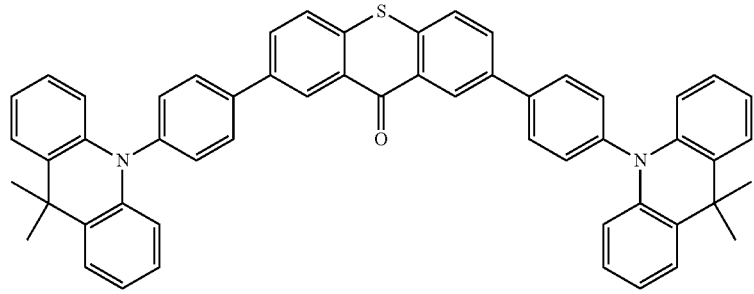
P21
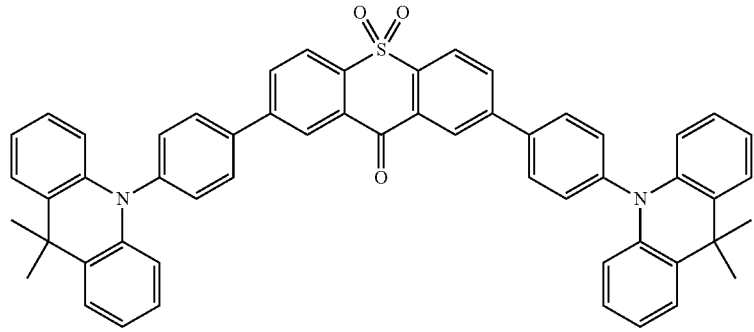
P22
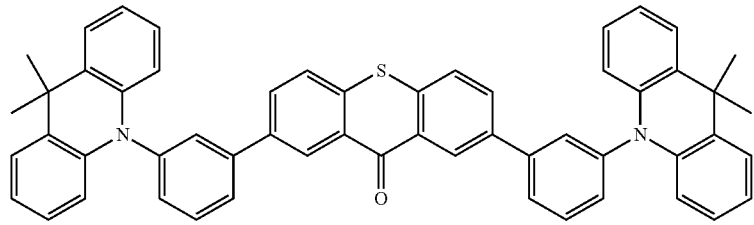
P23
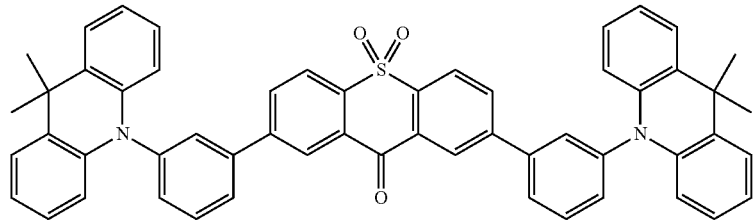
P24

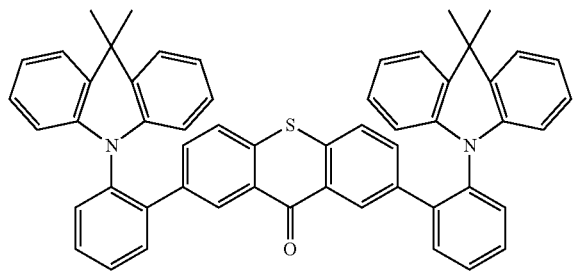
P25
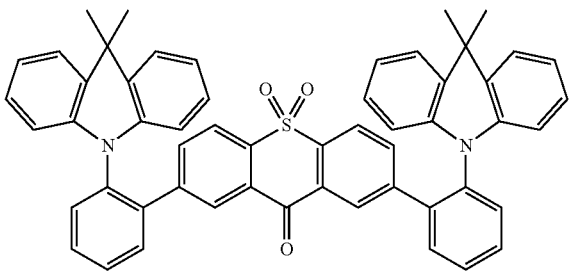
P26
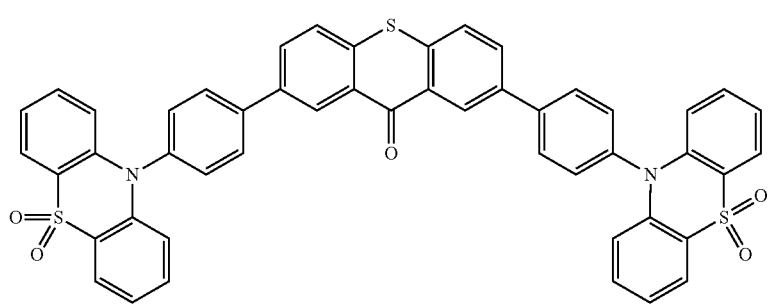
P33
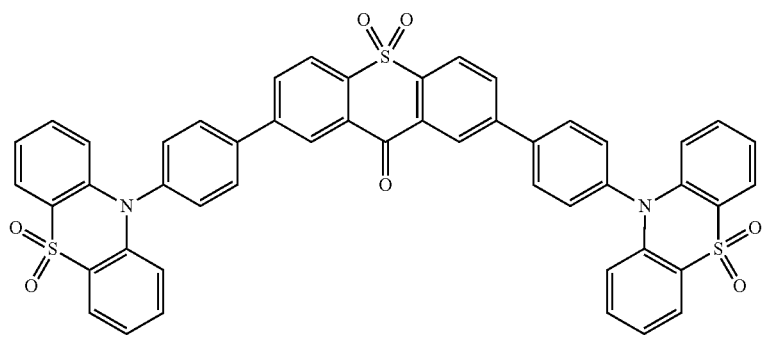
P34
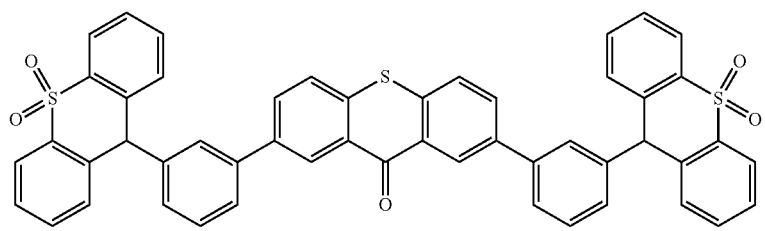
P35
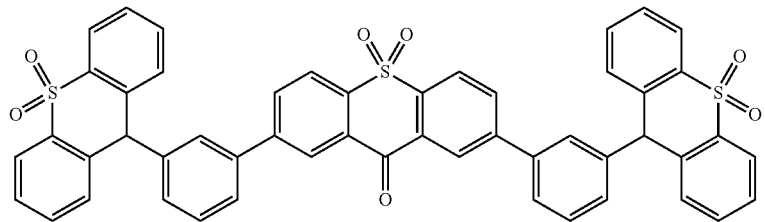
P36

P37
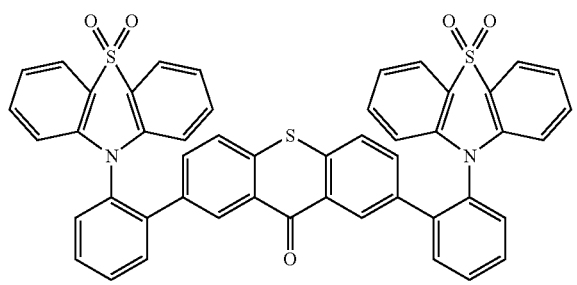

P38
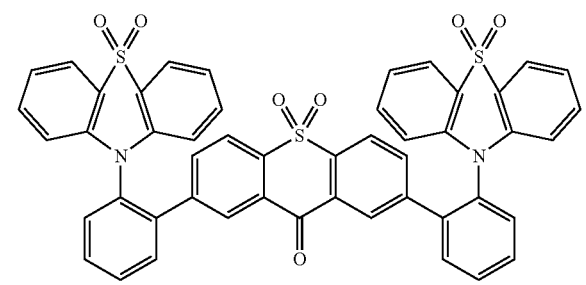

Alternatively, the $Ar_1$ and the $Ar_2$ each may be selected from the ammonia compounds with structures expressed by the formula (III) to formula (VII), and the $Ar_1$ and the $Ar_2$ having different structures.

In addition, the $Ar_1$ also may be a hydrogen atom, and the $Ar_2$ is selected from the ammonia compounds with structures expressed by the formula (III) to formula (VII). At this time, the thioxanthone aromatic amine compounds includes compounds P3, P4, P7, P8, P15, P16, P17, P18, P19, P20, P27, P28, P29, P30, P31, P32, P39, P40, P41, P42, P43 and P44, their structural formulas respectively are as follows:

P3
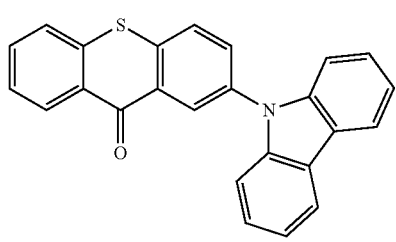

P4
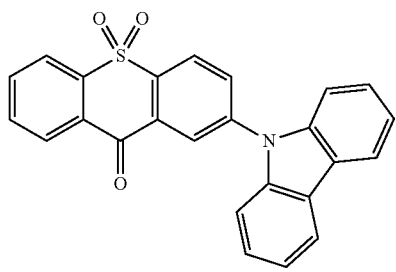

P7
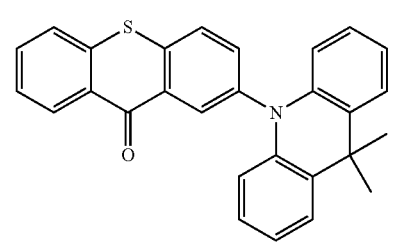

P8
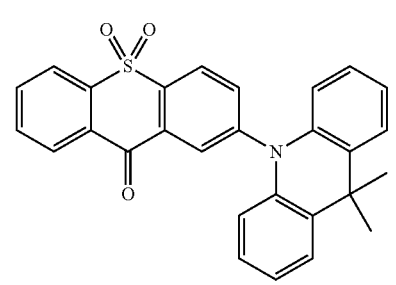

P15
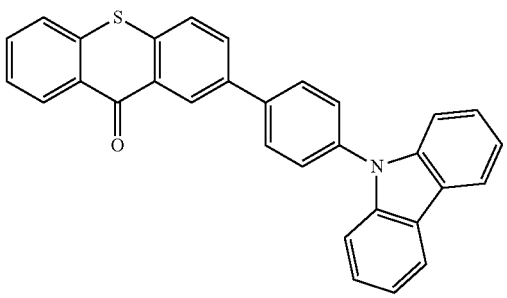

P16
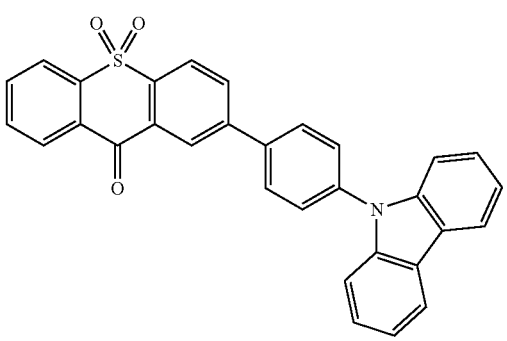

P17
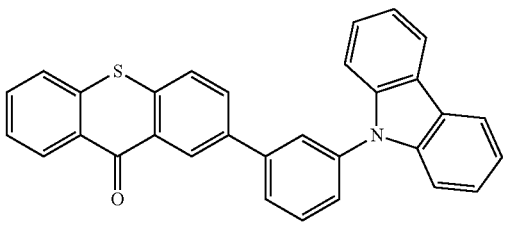

P18
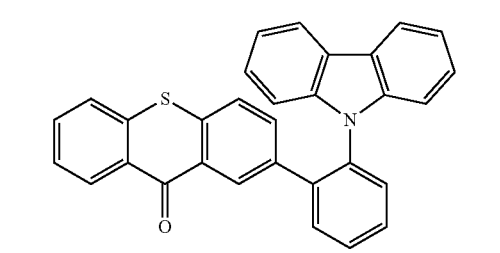

P19
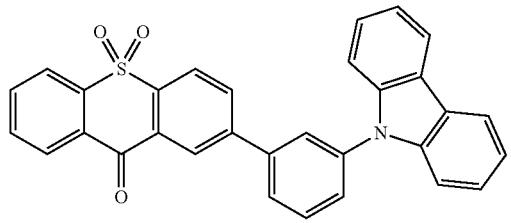
P20
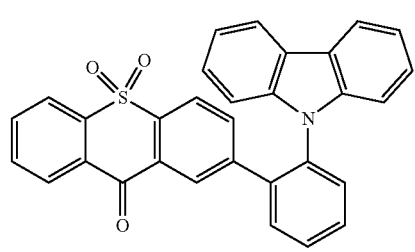
P27
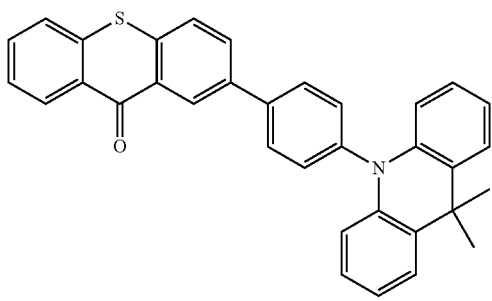
P28
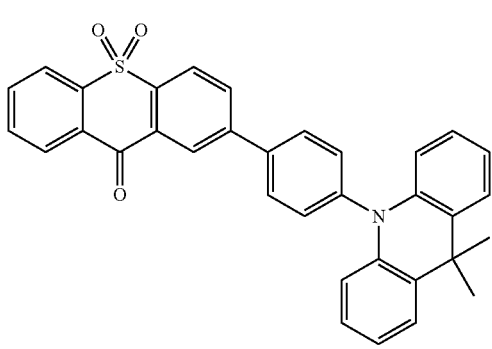
P29
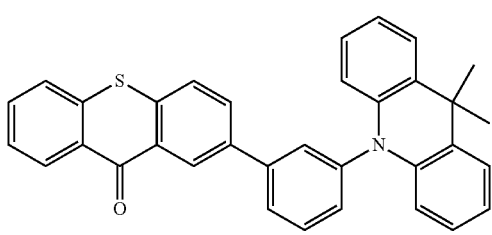
P30
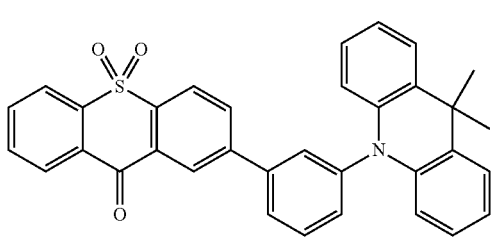
P31
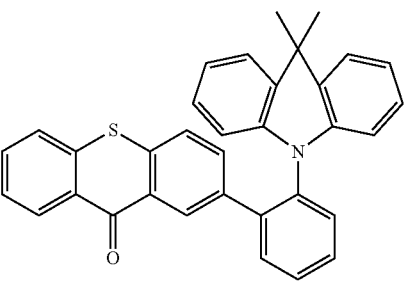
P32
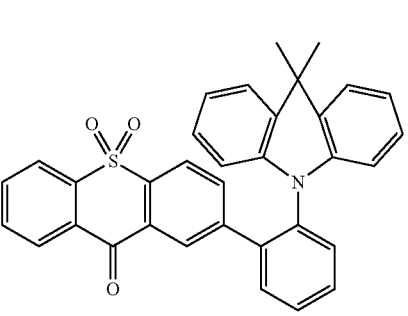
P39
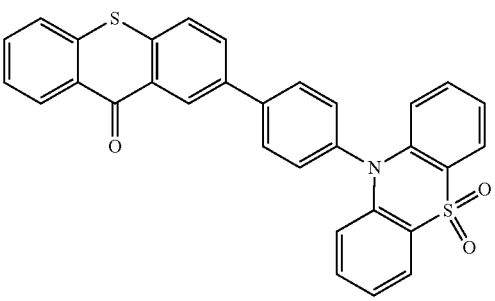
P40
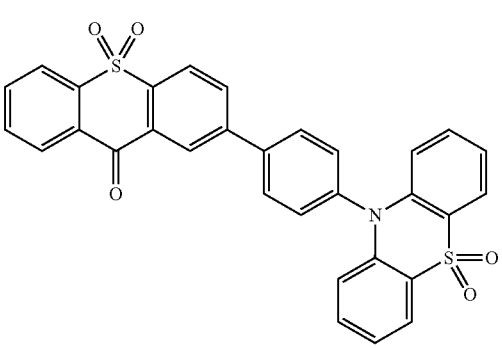
P41
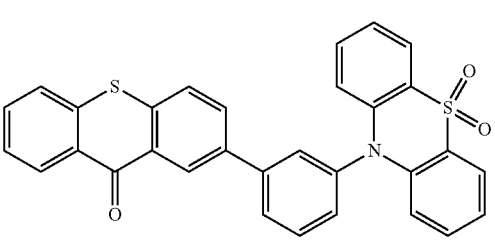

P42

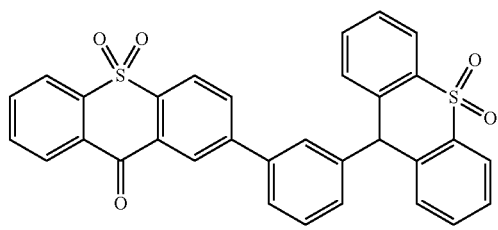

P43

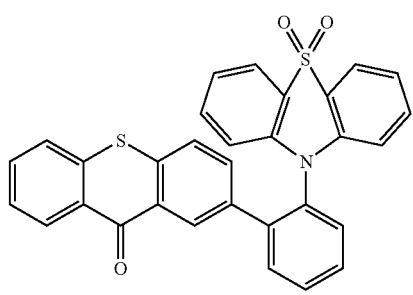

P44

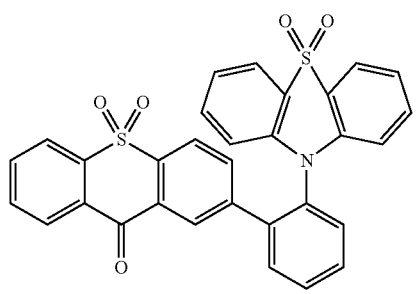

Before preparing the thioxanthone aromatic amine compound of the invention, an intermediate 1, an intermediate 2, an intermediate 3 or an intermediate 4 is need to be prepared firstly.

Specifically, a structural formula and a synthetic route of the intermediate 1 are shown as follows:

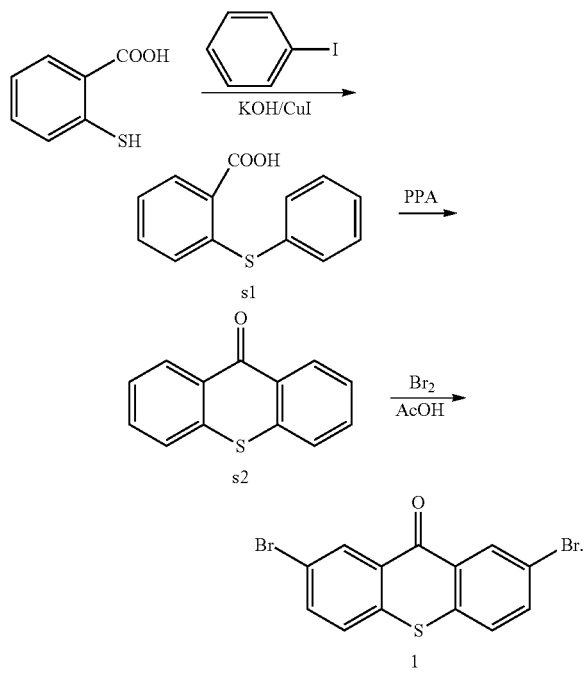

A preparation method of the compound expressed by formula s1 is that: using potassium hydroxide KOH (5.45 g, 97.3 mmol) and 60 ml water to form a solution and cooling the solution to the room temperature; under the protection of nitrogen (N2), adding mercapto salicylic acid (3.0 g, 38.9 mmol) to a 250 ml three-necked flask, adding copper bromide CuBr (0.167 g, 1.16 mmol), stirring at the room temperature for 20-30 min; Then, heating the reaction solution to 60° C., slowly dripping iodobenzene (6.08 g, 29.8 mmol) by a syringe, rising the temperature to reflux and reacting for 20-24 h, cooling to the room temperature and dripping 10 ml concentrated hydrochloric acid, after the dripping is completed, a large amount of solid is precipitated from the reaction solution, obtaining a yellow solid by suction filtration, washing with water to obtain a white solid, washing with a small amount of methanol, and drying in vacuum. Impure product does not affect next step, and carrying out the next step reaction directly.

A preparation method of the compound expressed by formula s2 is that: under the protection of nitrogen (N2), mixing the compound expressed by the formula s1 (6.53 g, 328.4 mmol) with 30 ml polyphosphoric acid, heating to 150° C., reacting for 7-8 h, cooling to the room temperature, pouring carefully into crushed ice, performing suction filtration and washing with 100 ml water, drying, extracting twice with 2×100 ml dichloromethane, spin-drying to obtain a gray solid, then drying to obtain 5.55 g solid, the yield is 95.5%.

Specifically, a preparation method of the intermediate 1 is that: under a nitrogen atmosphere, in a 100 ml three-neck flask, adding the compound 9-thioxanthone expressed by the formula s2 (1.0 g, 4.72 mmol), adding 20 ml acetic acid as a solvent dripping 2.5 ml bromine water in 30 min, refluxing reaction for 20 to 24 hours; cooling to the room temperature, pouring into an ice water, adding sodium sulfite, stirring, suction filtering and drying. A 0.83 g yellow-green solid is obtained by column chromatography separation, and the yield is 47%.

Specifically, a structural formula and a synthetic route of the intermediate 2 are shown as follows:

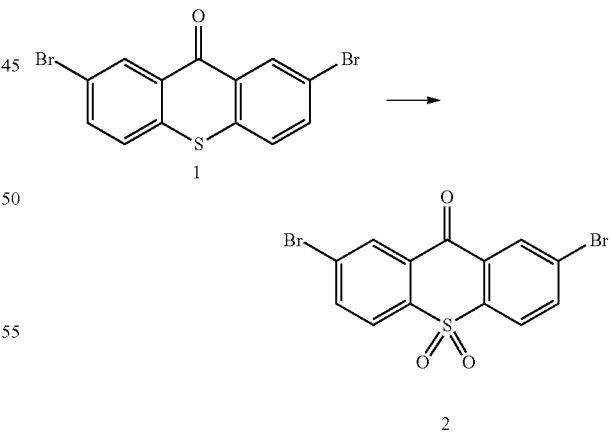

Specifically, a preparation method of the intermediate 2 is that: at the room temperature, in a 50 ml single-necked flask, adding 40 ml glacial acetic acid and 20 ml dichloromethane, adding the raw intermediate 1 (0.74 g, 2 mmol) and 5 times the equivalent of 30% hydrogen peroxide, stirring for 20-24 hours at 55-60° C., after cooling to the room temperature, extracting by dichloromethane, passing column, 0.66 g white solid then is obtained and the yield is 83%. $C_{13}H_6Br_2OS$ theoretical M/S=367.85 (100.0%), 367.85 (50.2%), 371.85 (47.8%), 370.85 (14.9%), 372.85 (7.7%), 368.85 (7.5%), 371.84 (4.4%), 373.84 (2.2%).

Specifically, a structural formula and a synthetic route of the intermediate 3 are shown as follows:

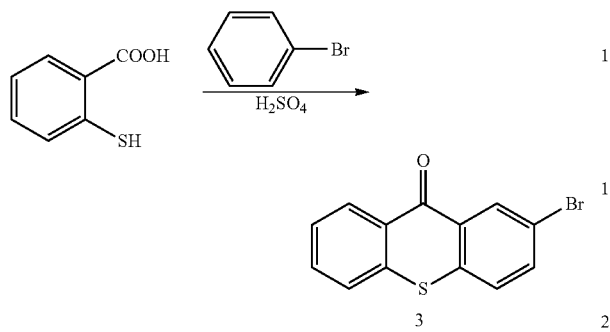

Specifically, a preparation method of the intermediate 3 is that: at the room temperature, in a 50 ml single-necked flask, adding 20 ml concentrated sulfuric acid, then adding 6 ml bromobenzene liquid, stirring for a half hour at the room temperature, obtaining a white turbid liquid, then adding 1.0 g mercapto salicylic acid in batches in half an hour; stirring at the room temperature for 20-24 hours, heating at 100° C. for 2-3 h, after cooling to the room temperature, carefully pouring into ice water, suction filtering to obtain a solid, then adding a 20% NaOH aqueous solution, stirring for 2 h, suction filtering, washing with water to neutral to thereby obtain a yellow solid, the yield is 83%. HNMR (400 MHz, $CDCl_3$, ppm): 7.70-7.90 (s, 2H), 7.40-7.60 (m, 4H), 7.30 (m, 1H).

Specifically, a structural formula and a synthetic route of the intermediate 4 are shown as follows:

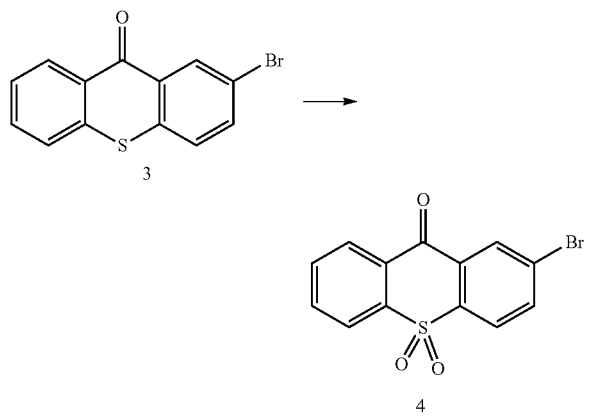

Specifically, a preparation method of the intermediate 4 is that: at the room temperature, in a 50 ml single-necked flask, adding 40 ml glacial acetic acid and 20 ml dichloromethane, adding the raw intermediate 3 (0.87 g, 3 mmol), 5 times the equivalent of 30% hydrogen peroxide, stirring for 20-24 hours at 55-60° C., after cooling to the room temperature, extracting by use of dichloromethane, passing column, 0.83 g white solid then is obtained and the yield is 86%. $C_{13}H_7BrO_3S$ theoretical M/S=321.93, 323.93 (100.0%), 321.93 (97.5%), 324.93 (14.9%), 322.93 (14.6%), 325.92 (4.3%), 325.93 (1.6%).

In the following specific embodiments, preparation methods of thioxanthone aromatic amine compounds of the invention will be described in detail.

Embodiment 1

This embodiment prepares the compound P1 (2,7-carbazol-thioxanthone), a structural formula and a synthetic route thereof are shown as follows:

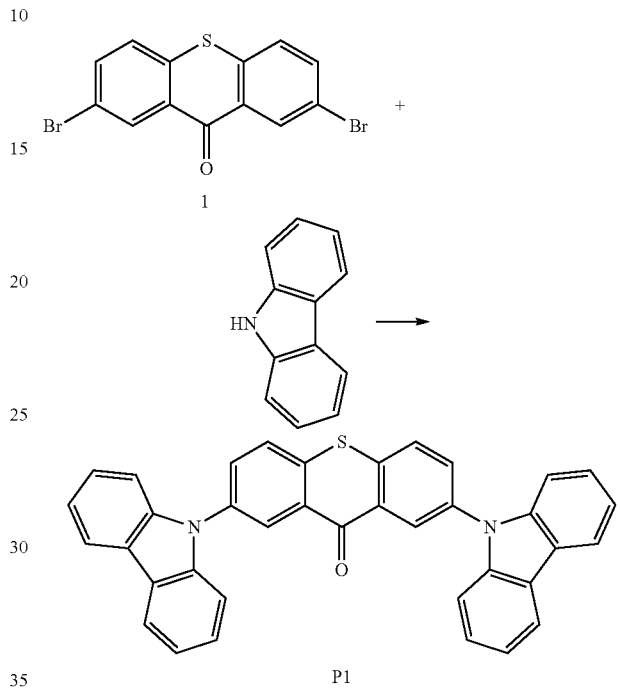

Figure 3:
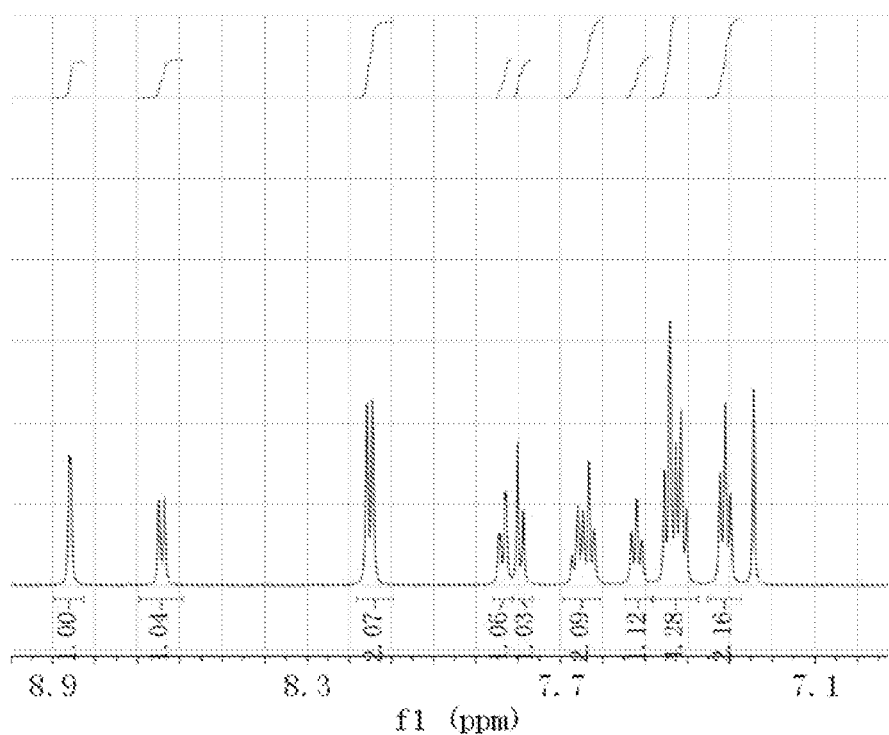
FIG. 3 is a hydrogen nuclear magnetic spectra view of a thioxanthone aromatic amine compound P1 of the invention.

Specific implementation steps are that:
under a nitrogen atmosphere, adding 3,7-dibromo-9-thioxanthone (2.22 g, 6 mmol), 20 ml DMPU, 0.167 g cuprous iodide, 0.600 g potassium carbonate, carbazole (2.22 g, 1.2 equ), 0.36 g 18-crown-6 in a 100 ml flask, ventilating for 5 min, reacting at 160-170° C. for 18-24 h. Extracting by dichloromethane, liquid separating, combining organic phases, drying by anhydrous magnesium sulfate, suction filtering, removing solvent from the resultant filtrate under reduced pressure, vacuum drying and column separating to obtain a yellow solid of 1.56 g, the yield is 48%. $C_{37}H_{22}N_2OS$ M/S=542.15; elemental analysis: C, 81.89; H, 4.09; N, 5.16; O, 2.95; S, 5.91. FIG. 3 is a hydrogen nuclear magnetic spectra view of the thioxanthone aromatic amine compound P1 of the invention.

Embodiment 2

This embodiment prepares the compound P2 (2,7-carbazol thioxanthone-sulfur, sulfur-dioxide), a structural formula and a synthetic route thereof are shown as follows:

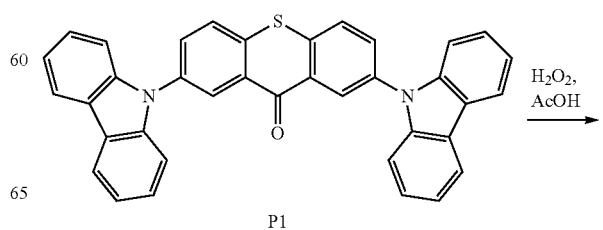

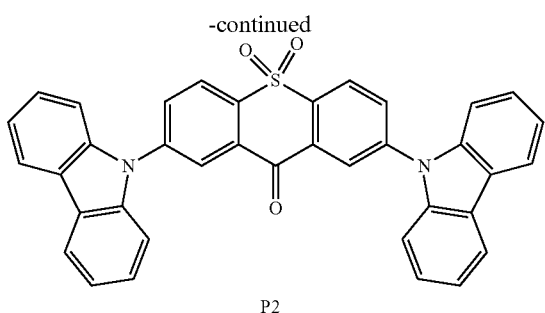

P2

Figure 4:
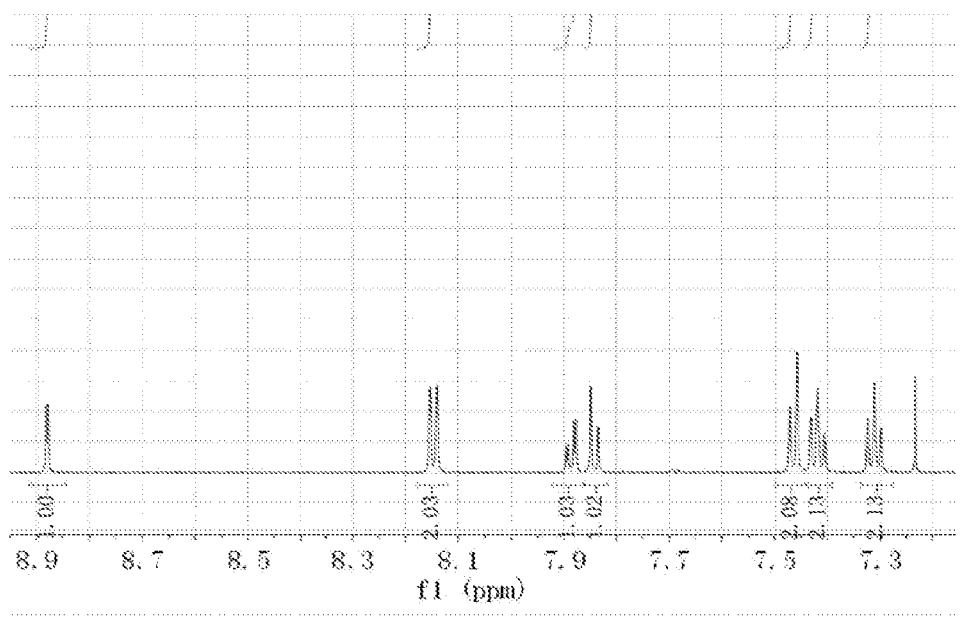
FIG. 4 is a hydrogen nuclear magnetic spectra view of a thioxanthone aromatic amine compound P2 of the invention.

Specific implementation steps are that:

at the room temperature, adding 0.60 g the compound P1 of 0.6 g to a 50 ml single-necked flask, adding 20 ml acetic acid and an excess amount of 30% hydrogen peroxide, oxidizing for 18-24 hours, suction filtering, washing with water, washing with a small amount of methanol, drying to obtain a product; passing short column, petroleum ether: dichloromethane=1:1 passing column, obtaining a yellow solid of 0.61 g, the yield is 97%. $C_{37}H_{22}N_2O_3S$ M/S=574.14, theoretical values: 574.14 (100.0%), 575.14 (40.4%), 576.14 (9.2%), 576.13 (4.5%), 577.13 (1.8%), 575.13 (1.5%), 577.15 (1.0%). Elemental analysis: C, 77.33; H, 3.86; N, 4.87; O, 8.35; S, 5.58. FIG. 4 is a hydrogen nuclear magnetic spectra view of the thioxanthone aromatic amine compound P2 of the invention.

Embodiment 3

This embodiment prepares the compound P3 (2-carbazole thioxanthone), a structural formula and a synthetic route thereof are shown as follows:

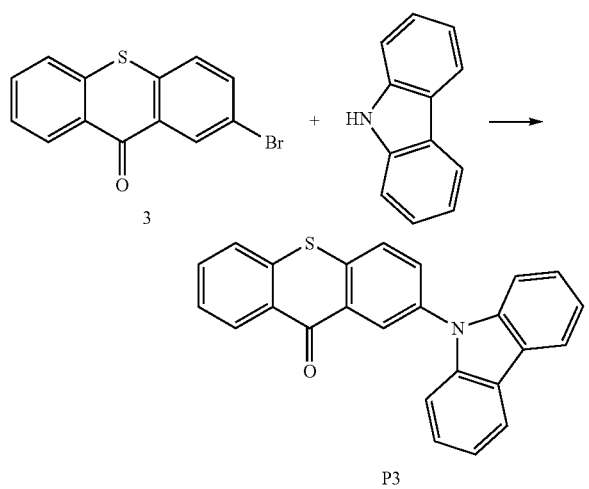

P3

Figure 5:
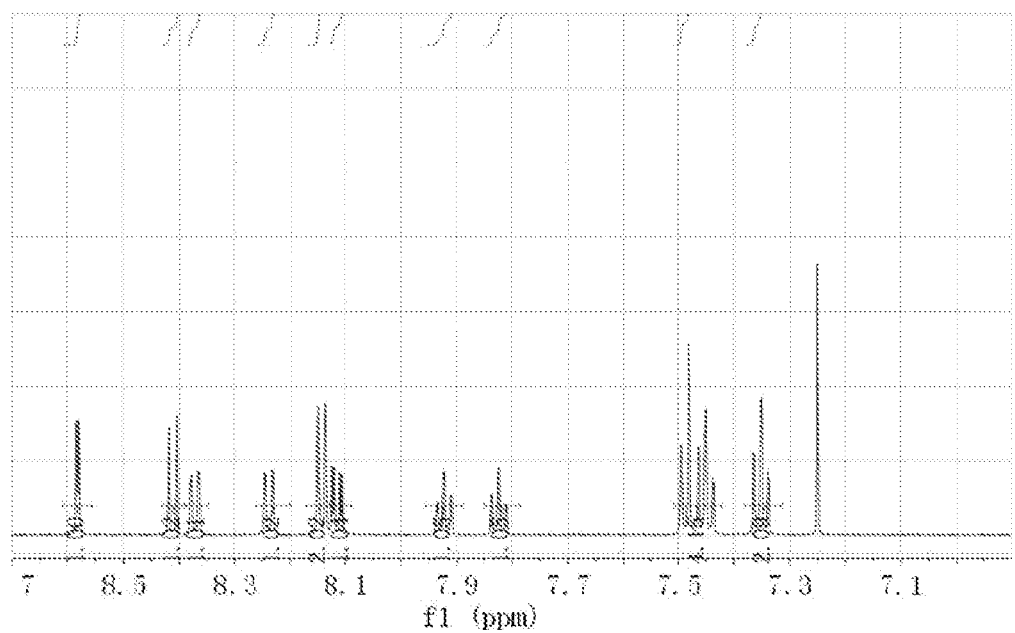
FIG. 5 is a hydrogen nuclear magnetic spectra view of a thioxanthone-aromatic amine compound P3 of the invention.

Specific implementation steps are that:

under a nitrogen atmosphere, adding 3-bromine-9-thioxanthone (1.01 g, 3.5 mmol), 15 ml DMPU, 0.56 g copper iodide, 1.40 g potassium carbonate, 0.71 g, 1.2 equ carbazole, 0.21 g 18-crown-6 in a 100 ml flask, ventilating for 5 min, reacting at 160-170° C. for 24 h. Extracting by dichloromethane, liquid separating, combining organic phases, drying by anhydrous magnesium sulfate, suction filtering, removing solvent from the resultant filtrate under reduced pressure, column separating to obtain a yellow solid of 0.739 g, the yield is 56%. $C_{25}H_{15}NOS$ M/S=377.09; theoretical values: 377.09 (100.0%), 378.09 (28.1%), 379.08 (4.5%), 379.09 (4.0%), 380.09 (1.3%). Elemental analysis: C, 79.55; H, 4.01; N, 3.71; O, 4.24; S, 8.49. FIG. 5 is a hydrogen nuclear magnetic spectra view of the thioxanthone aromatic amine compound P3 of the invention.

Embodiment 4

This embodiment prepares the compound P4 (2-carbazol thioxanthone-sulfur, sulfur-dioxide), a structural formula and a synthetic route thereof are shown as follows:

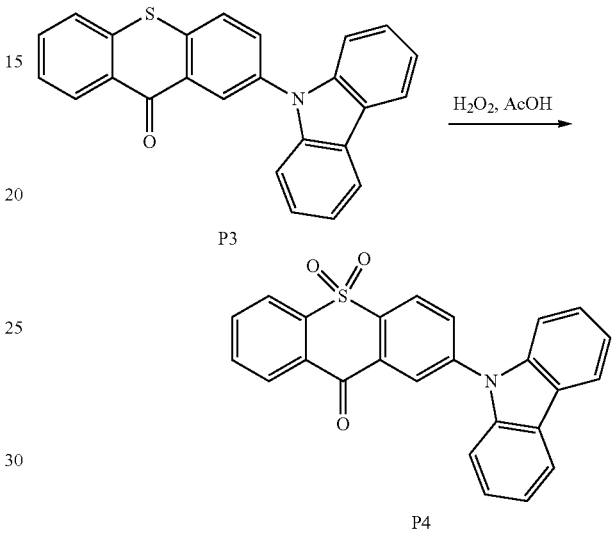

P4

Figure 6:
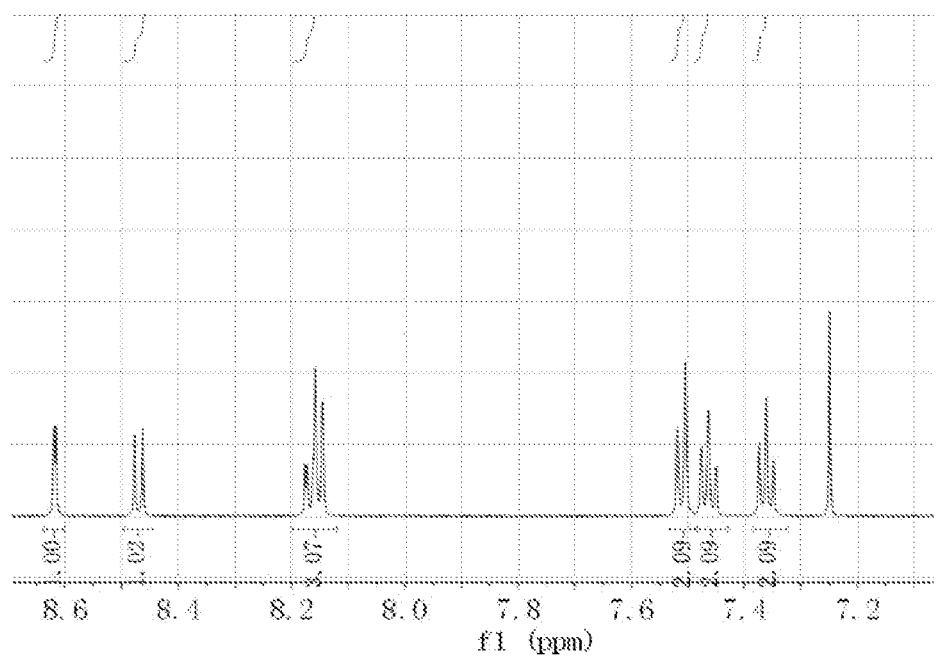
FIG. 6 is a hydrogen nuclear magnetic spectra view of a thioxanthone-aromatic amine compound P4 of the invention.

Specific implementation steps are that:

at room temperature, adding 0.50 g compound P3 to a 50 ml single-necked flask, adding 20 ml acetic acid and an excess amount of 30% hydrogen peroxide, oxidizing for 18-24 hours, suction filtering, washing with water, washing with a small amount of methanol, drying, dichloromethane: petroleum ether=1:1 passing column to obtain a yellow solid of 0.505 g, the yield is 98%. $C_{25}H_{15}NO_3S$ M/S=409.08, theoretical values: 409.08 (100.0%), 410.08 (28.1%), 411.07 (4.5%), 411.08 (4.5%), 412.08 (1.5%). Elemental analysis: C, 73.33; H, 3.69; N, 3.42; O, 11.72; S, 7.83. FIG. 6 is a hydrogen nuclear magnetic spectra view of the thioxanthone aromatic amine compound P4 of the invention.

Figure 2:
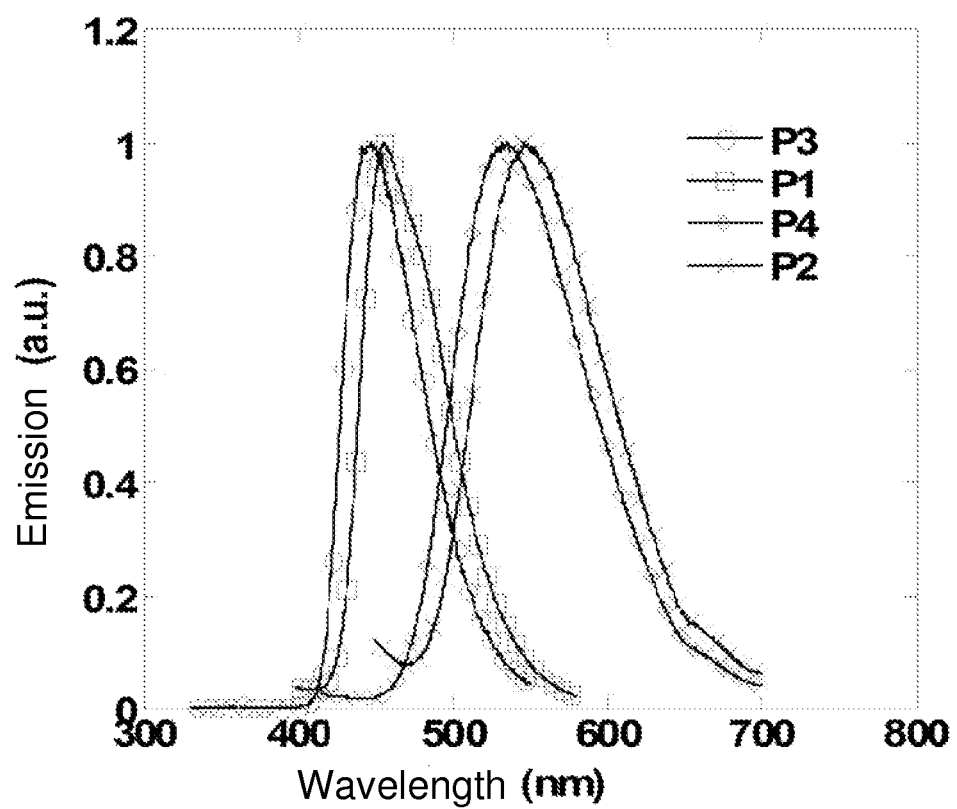
FIG. 2 is an emission spectra view of thioxanthone aromatic amine compounds P1, P2, P3, P4 in a methylbenzene solution of the invention.

FIG. 1 and FIG. 2 respectively are an absorption spectra view of the thioxanthone aromatic amine compounds P1, P2, P3, P4 in a dichloromethane solution of the invention and an emission spectra view of the thioxanthone aromatic amine compounds P1, P2, P3, P4 in toluene solution of the invention.

Embodiment 5

This embodiment prepares the compound P5, a structural formula and a synthetic route thereof are shown as follows:

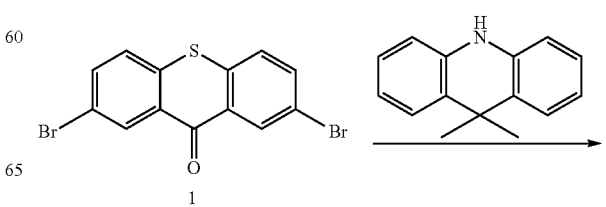

1

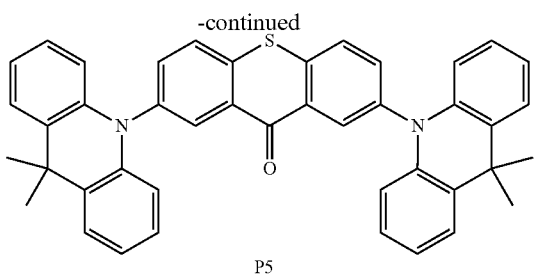

P5

Specific implementation steps are that:
under a nitrogen atmosphere, in a three-necked flask, adding 100 ml toluene, 0.74 g intermediate 1 (2 mmol) and 0.85 g dimethyl-acridine (5 mmol), adding 0.58 g sodium tert-butyl alcohol during stirring, and adding 20 mg Pd$_2$(dba)$_3$ (bis-dibenzylideneacetone palladium), and adding a 10% solution of tri-tert-butyl-n-hexane, heating to reflux, reacting for 18-24 h; cooling, extracting organic phase by dichloromethane, spin-drying, passing column, then obtaining a white solid product of 0.85 g, the yield is 56%. C$_{55}$H$_{42}$N$_2$S M/S=762.31, theoretical values: 762.31 (100.0%), 763.31 (62.6%), 764.31 (19.3%), 764.30 (4.4%), 765.32 (3.7%), 765.31 (3.0%). Elemental analysis: C, 86.58; H, 5.55; N, 3.67; S, 4.20.

Embodiment 6

This embodiment prepares the compound P6, a structural formula and a synthetic route thereof are shown as follows:

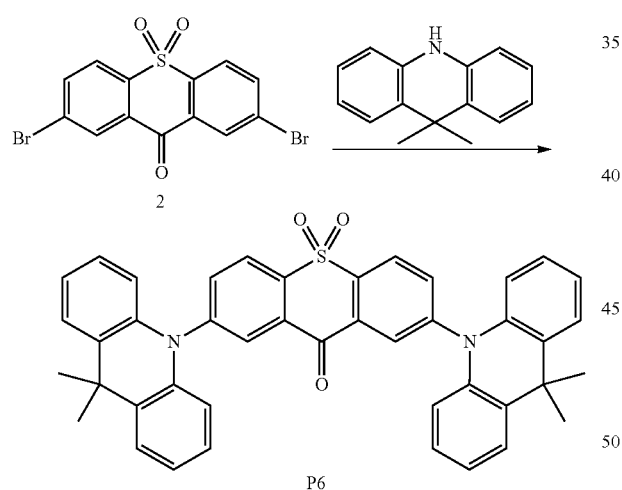

P6

Specific implementation steps are that:
the intermediate 1 in the embodiment 5 is replaced with the equivalent amount of the intermediate 2, other raw materials and steps are the same as that in the embodiment 5, thereby a white solid product of 0.81 g is obtained, and the yield is 51%. C$_{55}$H$_{42}$N$_2$O$_2$S M/S=794.30, theoretical values: 794.30 (100.0%), 795.30 (62.7%), 796.30 (19.8%), 796.29 (4.4%), 797.31 (3.7%), 797.30 (3.3%). Elemental analysis: C, 83.09; H, 5.32; N, 3.52; O, 4.03; S, 4.03.

Embodiment 7

This embodiment prepares the compound P7, a structural formula and a synthetic route thereof are shown as follows:

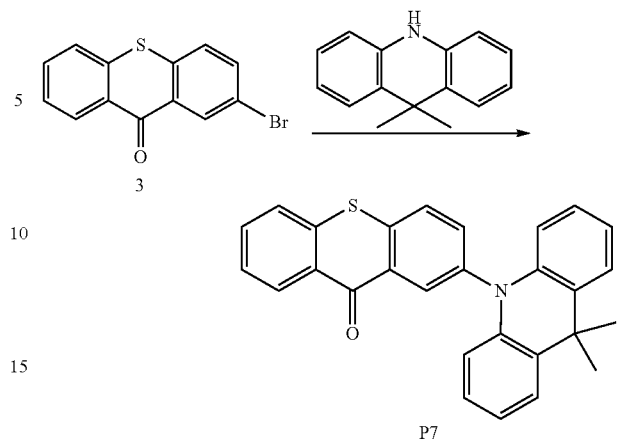

P7

Specific implementation steps are that:
the intermediate 1 in the embodiment 5 is replaced with the equivalent amount of the intermediate 3, other raw materials and steps are the same as that in the embodiment 5, thereby a white solid product of 0.57 g is obtained, and the yield is 52%. C$_{40}$H$_{29}$NS M/S=555.20, theoretical values: 555.20 (100.0%), 556.21 (44.9%), 557.21 (9.8%), 557.20 (4.9%), 558.20 (2.0%), 558.21 (1.5%), 556.20 (1.2%). Elemental analysis: C, 86.45; H, 5.26; N, 2.52; S, 5.77.

Embodiment 8

This embodiment prepares the compound P8, a structural formula and a synthetic route thereof a compound P8 are shown as follows:

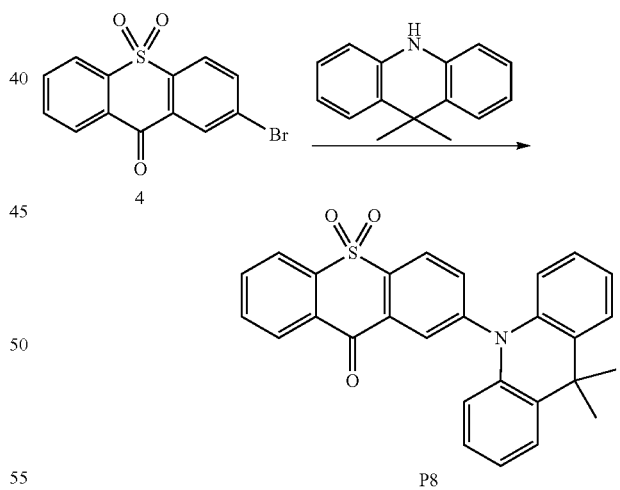

P8

Specific implementation steps are that:
the intermediate 1 shown in the embodiment 5 is replaced with the equivalent amount of the intermediate 4, other raw materials and steps are the same as that in the embodiment 5, thereby a white solid product of 0.61 g is obtained, and the yield is 52%. C$_{40}$H$_{29}$NO$_2$S M/S=587.19, theoretical values: 587.19 (100.0%), 588.20 (45.0%), 589.20 (10.3%), 589.19 (5.0%), 590.19 (2.0%), 590.20 (1.7%), 588.19 (1.2%). Elemental analysis: C, 81.74; H, 4.97; N, 2.38; O, 5.44; S, 5.46.

Embodiment 9

This embodiment prepares compound P9, a structural formula and a synthetic route thereof are shown as follows:

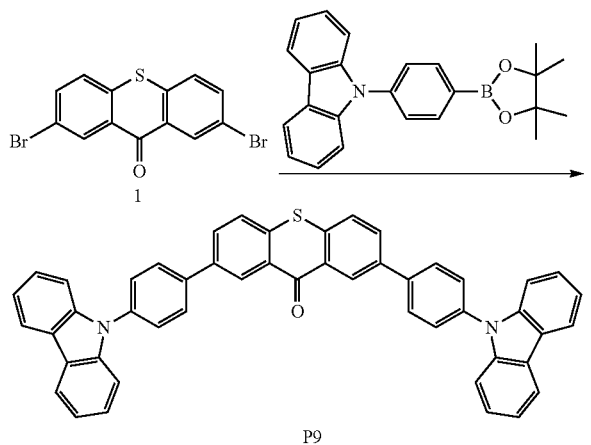

Specific implementation steps are that:

under a nitrogen atmosphere, in a 100 ml flask, adding 24 ml toluene, 8 ml ethanol, 5 ml 2M aqueous solution of potassium carbonate, 0.555 g, 1.5 mmol 3,7-dibromo-9-thioxanthone, 1.545 g, 1.2 equ carbazole phenyl borate ester; stirring at room temperature, then adding triphenylphosphine palladium catalyst, refluxing at 90-96° C. for 24 hours; cooling to the room temperature, extracting by dichloromethane, drying by anhydrous magnesium sulfate; thereby a light yellow solid of 0.68 g is obtained by column chromatography separation, and the yield is 65%. $C_{49}H_{30}N_2O_3S$ M/S=726.20, theoretical values: 726.20 (100.0%), 727.20 (54.3%), 728.20 (15.2%), 728.19 (4.5%), 729.21 (2.7%), 729.20 (2.6%). Elemental analysis: C, 80.97; H, 4.16; N, 3.85; O, 6.60; S, 4.41.

Embodiment 10

This embodiment prepares the compound P10, a structural formula and a synthetic route thereof are shown as follows:

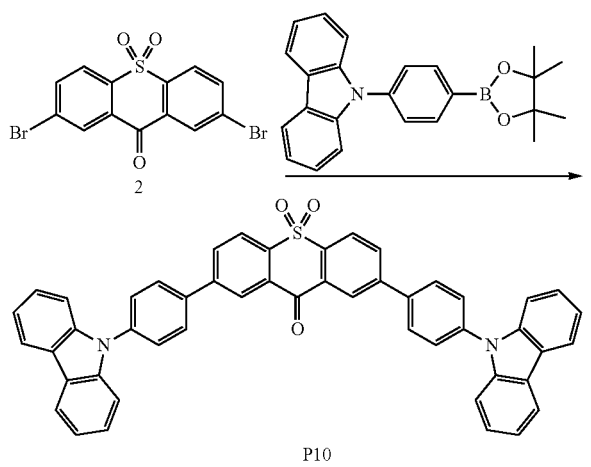

Specific implementation steps are that:

the intermediate 1 shown in the embodiment 9 is replaced with the equivalent amount of the intermediate 2, other raw materials and steps are the same as that in the embodiment 9, thereby a product of 1.05 g is obtained, and the yield is 97%. $C_{49}H_{30}N_2O_3S$ M/S=726.2, theoretical values: 726.20 (100.0%), 727.20 (54.3%), 728.20 (15.2%), 728.19 (4.5%), 729.21 (2.7%), 729.20 (2.6%). Elemental analysis: C, 80.97; H, 4.16; N, 3.85; O, 6.60; S, 4.41.

Embodiment 11

This embodiment prepares the compound P11, a structural formula and a synthetic route thereof are shown as follows:

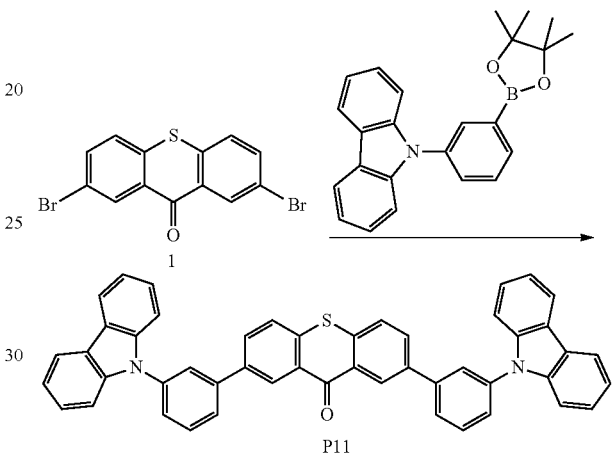

Specific implementation steps are that:

the para-phenylcarbazole borate ester in the embodiment 9 is replaced with the equivalent amount of meta-phenylcarbazole borate ester, other raw materials and steps are the same as that in the embodiment 9, thereby a white solid product of 0.99 g is obtained, and the yield is 80%. $C_{61}H_{38}N_2S$ M/S=830.28, theoretical values: 830.28 (100.0%), 831.28 (68.4%), 832.28 (23.7%), 833.29 (5.1%), 832.27 (4.4%), 833.27 (3.0%), 831.27 (1.5%), 834.28 (1.1%). Elemental analysis: C, 88.16; H, 4.61; N, 3.37; S, 3.86.

Embodiment 12

This embodiment prepares the compound P12, a structural formula and a synthetic route thereof are shown as follows:

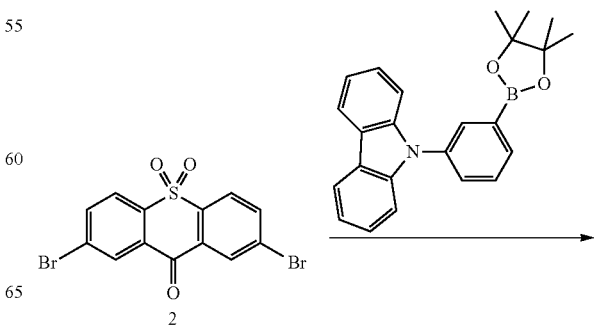

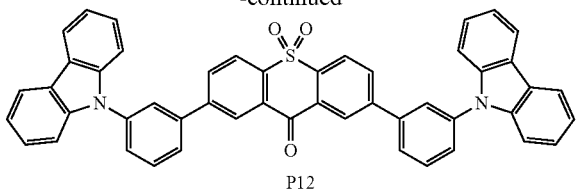

P12

Specific implementation steps are that:

the para-phenylcarbazole borate ester in the embodiment 9 is replaced with the equivalent amount of meta-phenylcarbazole borate ester, the intermediate 1 in the embodiment 9 is replaced with the equivalent amount of the intermediate 2, other raw materials and steps are the same as that in the embodiment 9, thereby a white solid product of 1.05 g is obtained, and the yield is 81%. $C_{61}H_{38}N_2O_2S$ M/S=862.27, theoretical values: 862.27 (100.0%), 863.27 (68.5%), 864.27 (24.5%), 865.28 (5.1%), 864.26 (4.4%), 865.26 (3.0%), 863.26 (1.5%), 866.27 (1.1%). Elemental analysis: C, 84.89; H, 4.44; N, 3.25; O, 3.71; S, 3.72.

Embodiment 13

This embodiment prepares the compound P13, a structural formula and a synthetic route thereof are shown as follows:

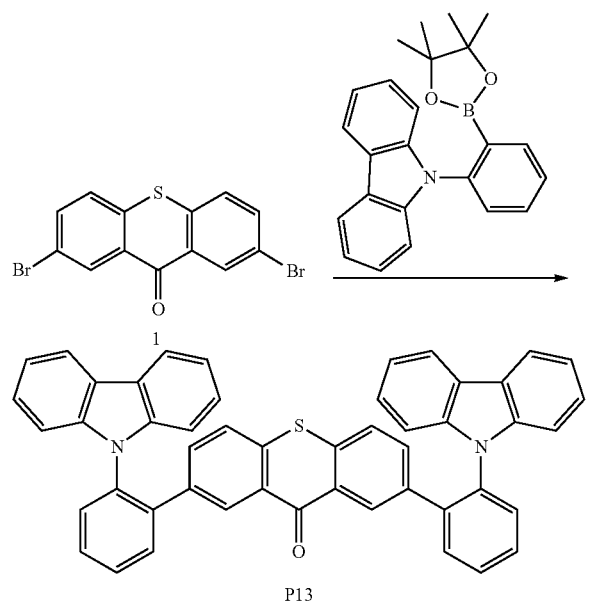

P13

Specific implementation steps are that:

the para-phenylcarbazole borate ester in the embodiment 9 is replaced with the equivalent amount of ortho-phenylcarbazole borate ester, other raw materials and steps are the same as that in the embodiment 9, thereby a white solid product of 1.0 g is obtained, and the yield is 81%. $C_{61}H_{38}N_2S$ M/S=830.28, theoretical values: 830.28 (100.0%), 831.28 (68.4%), 832.28 (23.7%), 833.29 (5.1%), 832.27 (4.4%), 833.27 (3.0%), 831.27 (1.5%), 834.28 (1.1%). Elemental analysis: C, 88.16; H, 4.61; N, 3.37; S, 3.86.

Embodiment 14

This embodiment prepares the compound P14, a structural formula and a synthetic route thereof are shown as follows:

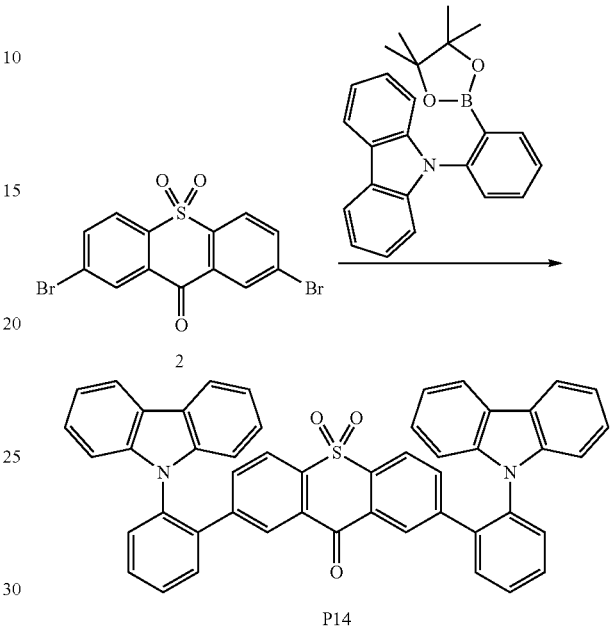

P14

Specific implementation steps are that:

the para-phenylcarbazole borate ester in the embodiment 9 is replaced with the equivalent amount of ortho-phenylcarbazole borate ester, the intermediate 1 is replaced with the equivalent amount of the intermediate 2, other raw materials and steps are the same as that in the embodiment 9, thereby a white solid product of 1.08 g is obtained, and the yield is 82%. $C_{62}H_{42}N_2O_2S$ M/S=878.30, theoretical values: 878.30 (100.0%), 879.30 (70.5%), 880.30 (24.9%), 881.31 (5.4%), 880.29 (4.4%), 881.30 (3.7%), 882.30 (1.1%), 882.31 (1.0%). Elemental analysis: C, 84.71; H, 4.82; N, 3.19; O, 3.64; S, 3.65.

Embodiment 15

This embodiment prepares the compound P15, a structural formula and a synthetic route thereof are shown as follows:

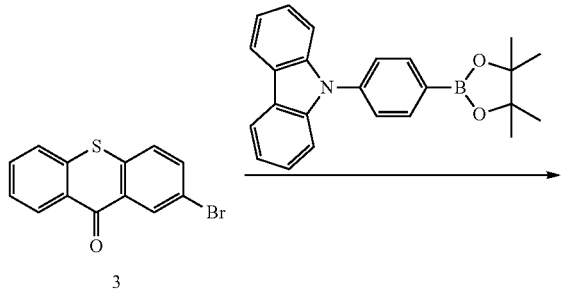

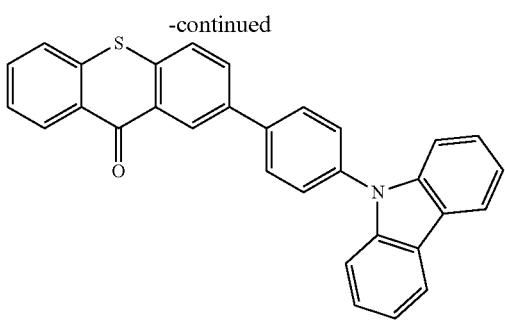

P15

Specific implementation steps are that:

under a nitrogen atmosphere, in a 100 ml flask, adding 48 ml toluene, 16 ml ethanol, 10 ml 2M aqueous solution of potassium carbonate, 3-bromine-9-thioxanthone (0.582 g, 2 mmol), 1.03 g, 1.2 equ carbazole phenyl borate ester, stirring at room temperature, then adding 75 mg triphenylphosphine palladium catalyst, refluxing at 90-96° C. for 18-24 hours; cooling to room temperature, extracting by dichloromethane, drying by anhydrous magnesium sulfate; petroleum ether:dichloromethane=1:3 passing column to obtain a light green solid of 0.580 g, and the yield is 64%, $C_{105}H_{64}N_4O_5S_3$ M/S=1556.40, theoretical values: m/z: 1557.41 (100.0%), 1556.40 (87.3%), 1558.41 (60.0%), 1559.41 (24.2%), 1559.40 (13.9%), 1558.40 (13.4%), 1560.41 (9.1%), 1560.42 (5.9%), 1557.40 (3.4%), 1561.41 (3.3%), 1561.42 (1.7%), 1560.40 (1.1%). Elemental analysis: C, 80.95; H, 4.14; N, 3.60; O, 5.14; S, 6.17.

Embodiment 16

This embodiment prepares the compound P16, a structural formula and a synthetic route thereof are shown as follows:

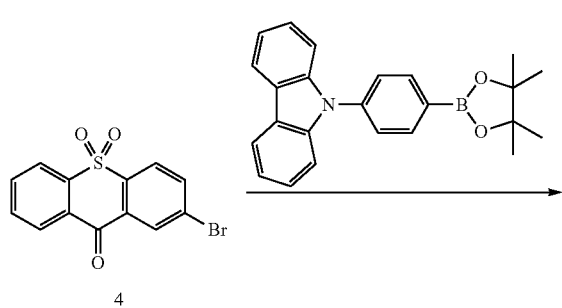

P16

Specific implementation steps are that:

the para-phenylcarbazole borate ester in the embodiment 15 is replaced with the equivalent amount of ortho-phenylcarbazole borate ester, and the intermediate 3 is replaced with the equivalent amount of the intermediate 4, other raw materials and steps are the same as that in the embodiment 15, after passing column, a light green solid is obtained, and the yield is 97%, $C_{31}H_{19}NO_3S$, M/S=485.11, theoretical values: m/e: 485.11 (100.0%), 486.11 (35.0%), 487.12 (5.6%), 487.10 (4.5%), 488.11 (1.6%), 487.11 (1.0%). Elemental analysis: C, 76.68; H, 3.94; N, 2.88; O, 9.89; S, 6.60.

Embodiment 17

This embodiment prepares the compound P17, a structural formula and a synthetic route thereof are shown as follows:

Specific implementation steps are that:

the para-phenylcarbazole borate ester in the embodiment 15 is replaced with the equivalent amount of meta-phenylcarbazole borate ester, other raw materials and steps are the same as that in the embodiment 15, thereby a white solid product of 0.68 g is obtained, and the yield is 78%, $C_{43}H_{27}NS$ M/S=589.19, theoretical values: 589.19 (100.0%), 590.19 (49.0%), 591.19 (11.7%), 591.18 (4.4%), 592.19 (2.3%), 592.20 (1.7%). Elemental analysis: C, 87.57; H, 4.61; N, 2.38; S, 5.44.

Embodiment 18

This embodiment prepares the compound P18, a structural formula and a synthetic route thereof are shown as follows:

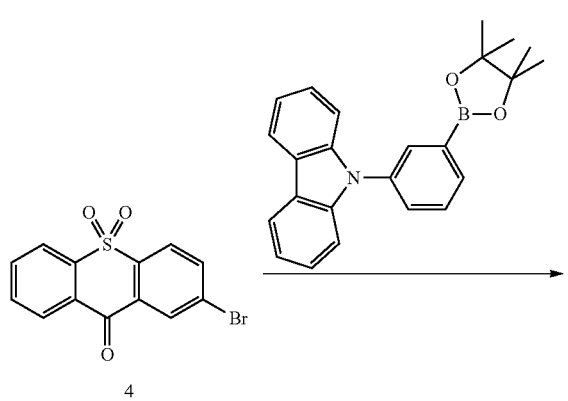

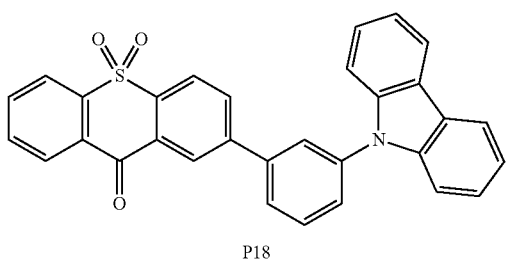

P18

Specific implementation steps are that:

the para-phenyl-carbazole borate ester in the embodiment 15 is replaced with the equivalent amount of meta-phenyl-carbazole borate ester, and the intermediate 3 is replaced with the equivalent amount of the intermediate 4, other raw materials and steps are the same as that in the embodiment 15, thereby a white solid product of 0.72 g is obtained, and the yield is 78%, $C_{43}H_{27}NO_2S$ M/S=621.18, theoretical values: 621.18 (100.0%), 622.18 (49.1%), 623.18 (12.2%), 623.17 (4.4%), 624.18 (2.5%), 624.19 (1.8%). Elemental analysis: C, 83.07; H, 4.38; N, 2.25; O, 5.15; S, 5.16.

Embodiment 19

This embodiment prepares the compound P19, a structural formula and a synthetic route thereof are shown as follows:

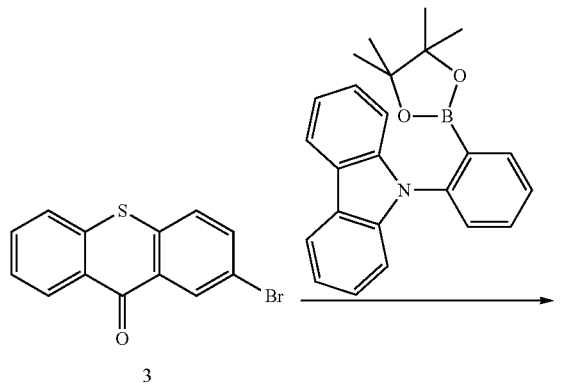

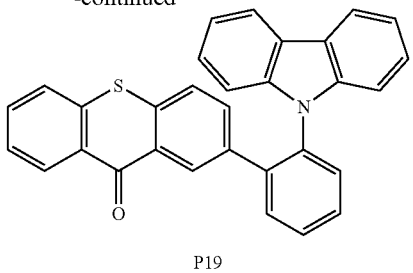

P19

Specific implementation steps are that:

the para-phenyl-carbazole borate ester in the embodiment 15 is replaced with the equivalent amount of ortho-phenyl-carbazole borate ester, other raw materials and steps are the same as that in the embodiment 15, thereby a white solid product of 0.68 g is obtained, and the yield is 77%. $C_{43}H_{27}NS$ M/S=589.19, theoretical values: 589.19 (100.0%), 590.19 (49.0%), 591.19 (11.7%), 591.18 (4.4%), 592.19 (2.3%), 592.20 (1.7%). Elemental analysis: C, 87.57; H, 4.61; N, 2.38; S, 5.44.

Embodiment 20

This embodiment prepares the compound P20, a structural formula and a synthetic route thereof are shown as follows:

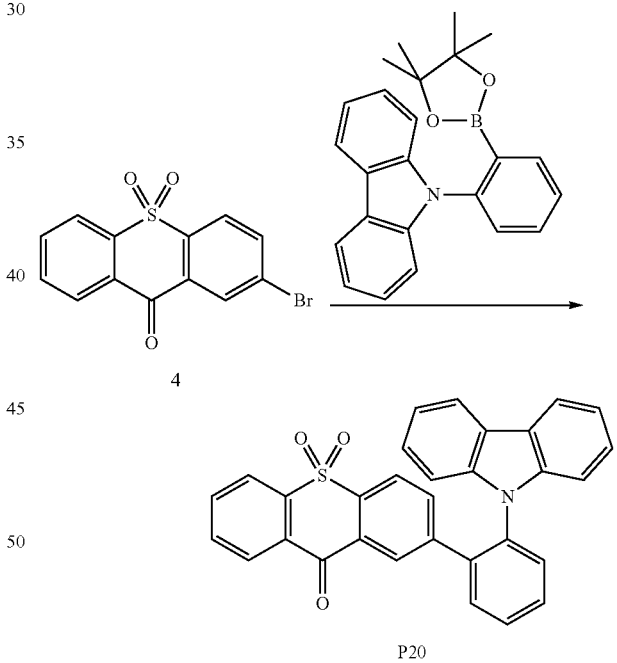

P20

Specific implementation steps are that:

the para-phenylcarbazole borate ester in the embodiment 15 is replaced with the equivalent amount of ortho-phenyl-carbazole borate ester, and the intermediate 3 in the embodiment 15 is replaced with the equivalent amount of the intermediate 4, other raw materials and steps are the same as that in the embodiment 15, thereby a white solid product of 0.708 g is obtained, and the yield is 76%. $C_{43}H_{27}NO_2S$ M/S=621.18, theoretical values: 621.18 (100.0%), 622.18 (49.1%), 623.18 (12.2%), 623.17 (4.4%), 624.18 (2.5%), 624.19 (1.8%). Elemental analysis: C, 83.07; H, 4.38; N, 2.25; O, 5.15; S, 5.16.

Embodiment 21

This embodiment prepares the compound P21, a structural formula and a synthetic route thereof are shown as follows:

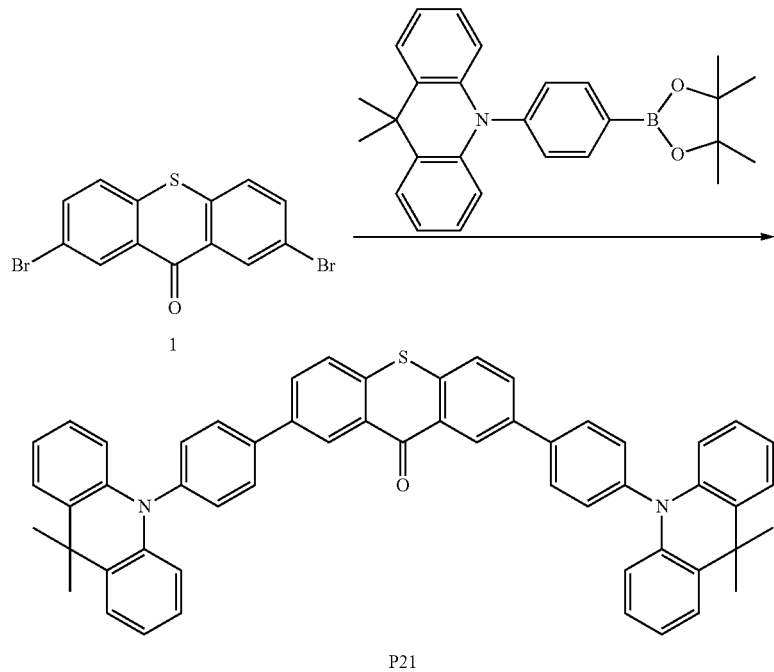

Specific implementation steps are that:

the benzoic carbazole borate ester in the embodiment 9 is replaced with the equivalent amount of benzene-substituted acridine borate ester, other raw materials and steps are the same as that in the embodiment 9, thereby a white solid product of 0.685 g is obtained, and the yield is 75%. $C_{67}H_{50}N_2S$ M/S=914.37, theoretical values: 914.37 (100.0%), 915.37 (76.1%), 916.38 (27.9%), 917.38 (7.0%), 916.37 (5.6%), 917.37 (3.5%), 918.38 (1.3%), 918.37 (1.3%). Elemental analysis: C, 87.93; H, 5.51; N, 3.06; S, 3.50.

Embodiment 22

This embodiment prepares the compound P22, a structural formula and a synthetic route thereof are shown as follows:

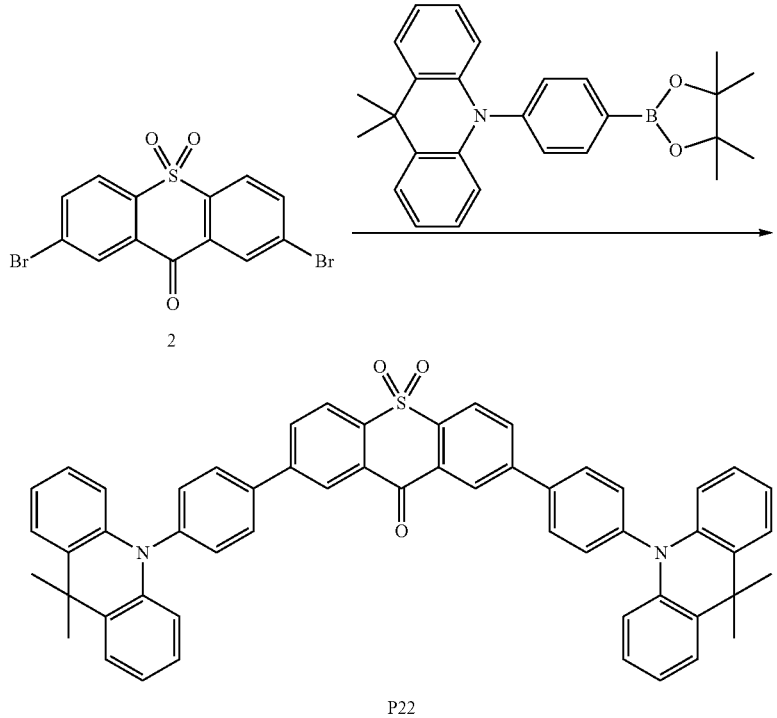

Specific implementation steps are that:

the benzoic carbazole borate ester in the embodiment 9 is replaced with the equivalent amount of benzene-substituted acridine borate ester, and the intermediate 1 is replaced with the equivalent amount of the intermediate 2, other raw materials and steps are the same as that in the embodiment 9, thereby a white solid product of 1.05 g is obtained, and the yield is 74%. $C_{67}H_{50}N_2O_2S$ M/S=946.36, theoretical values: 946.36 (100.0%), 947.36 (76.1%), 948.37 (28.0%), 949.37 (7.3%), 948.36 (6.0%), 949.36 (3.6%), 950.37 (1.4%), 950.36 (1.3%). Elemental analysis: C, 84.96; H, 5.32; N, 2.96; O, 3.38; S, 3.39.

Embodiment 23

This embodiment prepares the compound P23, a structural formula and a synthetic route thereof are shown as follows:

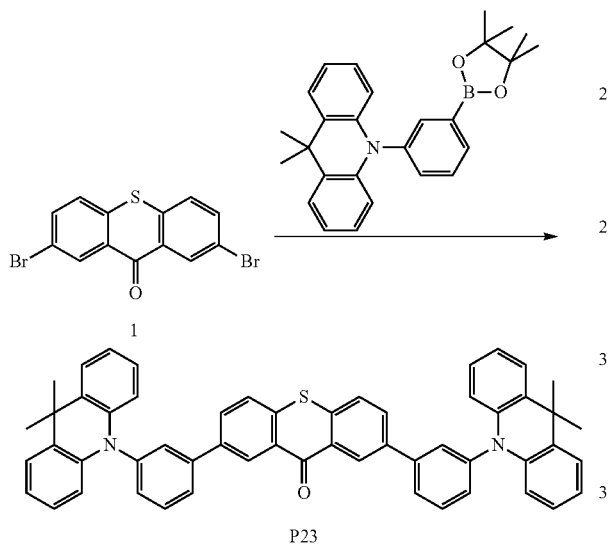

P23

Specific implementation steps are that:

the benzoic carbazole borate ester in the embodiment 9 is replaced with the equivalent amount of benzene-substituted acridine borate ester, other raw materials and steps are the same as that in the embodiment 9, thereby a white solid product of 1.10 g is obtained, and the yield is 81%. $C_{67}H_{50}N_2S$ M/S=914.37, theoretical values: 914.37 (100.0%), 915.37 (76.1%), 916.38 (27.9%), 917.38 (7.0%), 916.37 (5.6%), 917.37 (3.5%), 918.38 (1.3%), 918.37 (1.3%). Elemental analysis: C, 87.93; H, 5.51; N, 3.06; S, 3.50.

Embodiment 24

This embodiment prepares the compound P24, a structural formula and a synthetic route thereof are shown as follows:

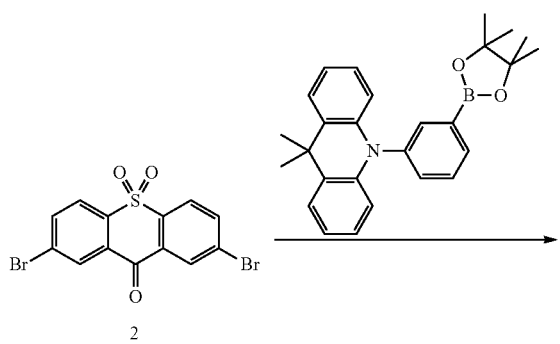

-continued

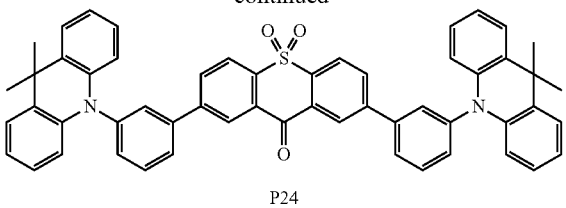

P24

Specific implementation steps are that:

the benzoic carbazole borate ester in the embodiment 9 is replaced with the equivalent amount of benzene-substituted acridine borate ester, and the intermediate 1 is replaced with the equivalent amount of the intermediate 2, other raw materials and steps are the same as that in the embodiment 9, thereby a white solid product of 1.15 g is obtained, and the yield is 81%. $C_{67}H_{50}N_2O_2S$ M/S=946.36, theoretical values: 946.36 (100.0%), 947.36 (76.1%), 948.37 (28.0%), 949.37 (7.3%), 948.36 (6.0%), 949.36 (3.6%), 950.37 (1.4%), 950.36 (1.3%). Elemental analysis: C, 84.96; H, 5.32; N, 2.96; O, 3.38; S, 3.39.

Embodiment 25

The compound P25 and a synthetic route thereof in this embodiment are shown as follows:

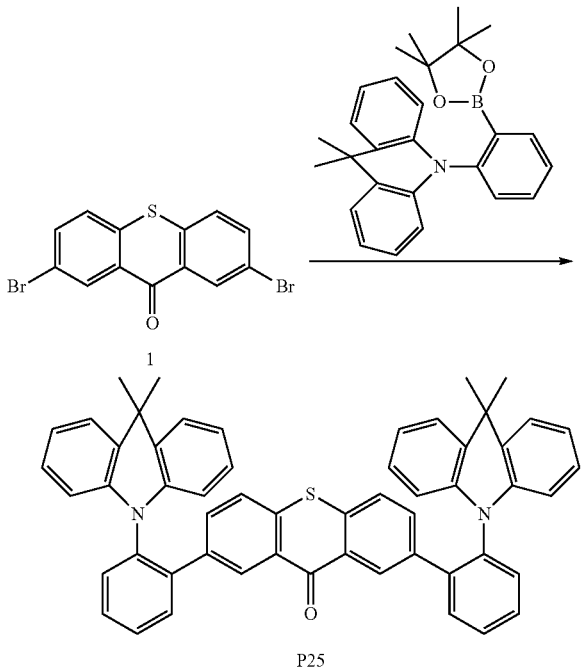

P25

Specific implementation steps are that:

the benzoic carbazole borate ester in the embodiment 9 is replaced with the equivalent amount of benzene-substituted acridine borate ester, other raw materials and steps are the same as that in the embodiment 9, a white solid product of 1.07 g is obtained, and the yield is 78%. $C_{67}H_{50}N_2S$ M/S=914.37, theoretical values: 914.37 (100.0%), 915.37 (76.1%), 916.38 (27.9%), 917.38 (7.0%), 916.37 (5.6%), 917.37 (3.5%), 918.38 (1.3%), 918.37 (1.3%). Elemental analysis: C, 87.93; H, 5.51; N, 3.06; S, 3.50.

Embodiment 26

This embodiment prepares the compound P26, a structural formula and a synthetic route thereof are shown as follows:

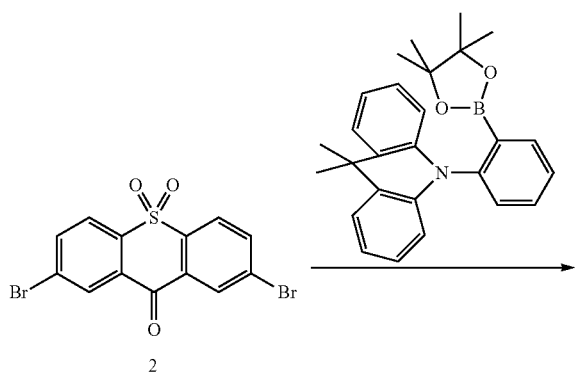

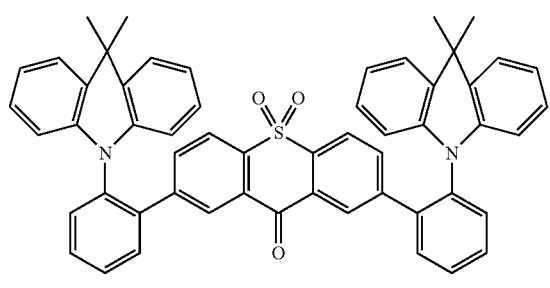

P26

Specific implementation steps are that:

the phenylcarbazole borate ester in the embodiment 9 is replaced with an equivalent amount of benzene-substituted acridine, the intermediate 1 is replaced with an equivalent amount of the intermediate 2, other raw materials and steps are the same as that in the embodiment 9, thereby a white solid product of 1.078 g is obtained, and the yield is 76%. $C_{67}H_{50}N_2O_2S$ M/S=946.36, theoretical values: 946.36 (100.0%), 947.36 (76.1%), 948.37 (28.0%), 949.37 (7.3%), 948.36 (6.0%), 949.36 (3.6%), 950.37 (1.4%), 950.36 (1.3%). Elemental analysis: C, 84.96; H, 5.32; N, 2.96; O, 3.38; S, 3.39.

Embodiment 27

This embodiment prepares the compound P27, a structural formula and a synthetic route thereof are shown as follows:

P27

Specific implementation steps are that:

the phenylcarbazole borate ester in the embodiment 15 is replaced with an equivalent amount of benzene-substituted acridine, other raw materials and steps are the same as that in the embodiment 15, thereby a white solid product of 0.719 g is obtained, and the yield is 76%. $C_{46}H_{33}NS$ M/S=631.23, theoretical values: 631.23 (100.0%), 632.24 (51.7%), 633.24 (13.5%), 633.23 (4.6%), 634.23 (2.3%), 634.24 (2.3%), 632.23 (1.2%). Elemental analysis: C, 87.44; H, 5.26; N, 2.22; S, 5.07.

Embodiment 28

This embodiment prepares the compound P28, a structural formula and a synthetic route thereof are shown as follows:

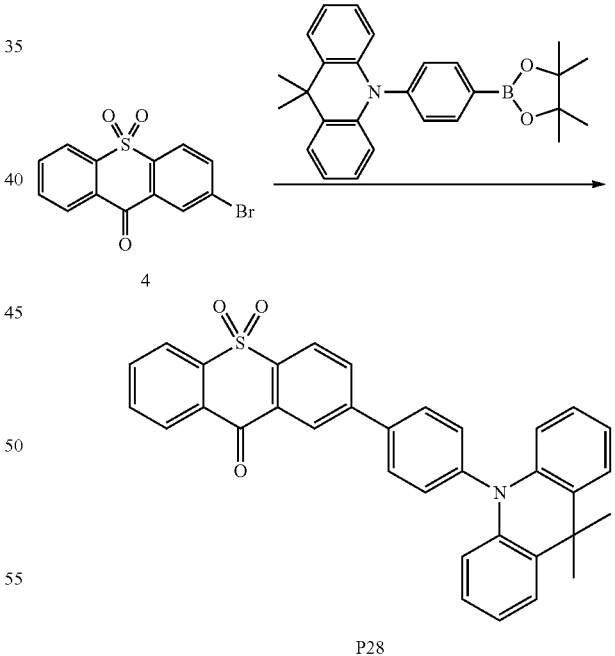

P28

Specific implementation steps are that:

the phenylcarbazole borate ester in the embodiment 15 is replaced with an equivalent amount of benzene-substituted acridine borate ester, the intermediate 3 is replaced with an equivalent amount of the intermediate 4, other raw materials and steps are the same as that in the embodiment 15, thereby a white solid product of 0.75 g is obtained, and the yield is 76%. $C_{46}H_{33}NO_2S$ M/S=663.22, theoretical values: 663.22

(100.0%), 664.23 (51.7%), 665.23 (13.9%), 665.22 (4.6%), 666.23 (2.5%), 666.22 (2.3%), 664.22 (1.2%). Elemental analysis: C, 83.23; H, 5.01; N, 2.11; O, 4.82; S, 4.83.

Embodiment 29

This embodiment prepares the compound P29, a structural formula and a synthetic route thereof are shown as follows:

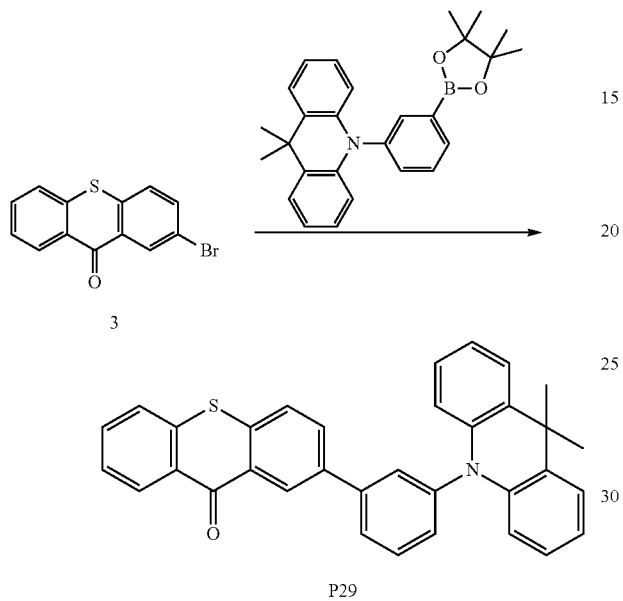

P29

Specific implementation steps are that:
the benzoic carbazole borate ester in the embodiment 15 is replaced with an equivalent amount of benzene-substituted acridine borate ester, other raw materials and steps are the same as that in the embodiment 15, thereby a white solid product of 0.64 g is obtained, and the yield is 68%. $C_{46}H_{33}NS$ M/S=631.23, theoretical values: 631.23 (100.0%), 632.24 (51.7%), 633.24 (13.5%), 633.23 (4.6%), 634.23 (2.3%), 634.24 (2.3%), 632.23 (1.2%). Elemental analysis: C, 87.44; H, 5.26; N, 2.22; S, 5.07.

Embodiment 30

This embodiment prepares the compound P30, a structural formula and a synthetic route thereof are shown as follows:

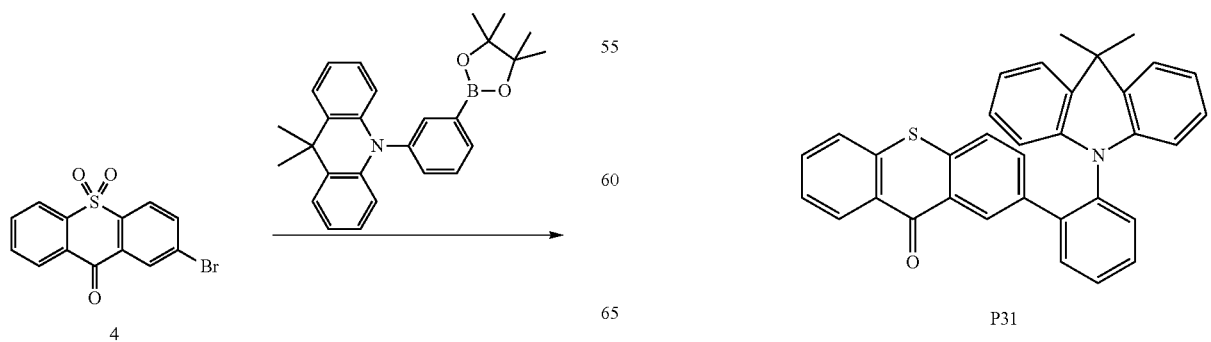

P30

Specific implementation steps are that:
the benzoic carbazole borate ester in the embodiment 15 is replaced with the equivalent amount of benzene-substituted acridine borate ester, the intermediate 3 is replaced with the equivalent amount of the intermediate 4, other raw materials and steps are the same as that in the embodiment 15, thereby a white solid product of 0.76 g is obtained, and the yield is 76%. $C_{46}H_{33}NO_2S$ M/S=663.22, theoretical values: 663.22 (100.0%), 664.23 (51.7%), 665.23 (13.9%), 665.22 (4.6%), 666.23 (2.5%), 666.22 (2.3%), 664.22 (1.2%). Elemental analysis: C, 83.23; H, 5.01; N, 2.11; O, 4.82; S, 4.83.

Embodiment 31

The compound P31 and a synthetic route thereof in this embodiment are shown as follows:

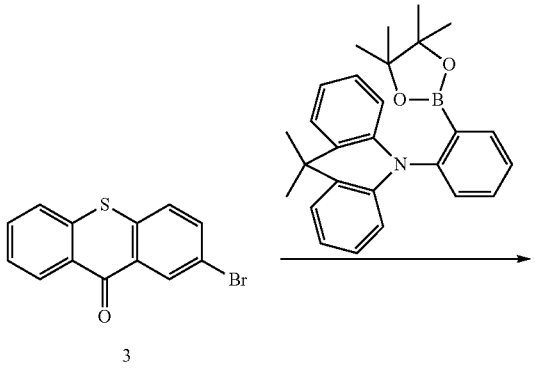

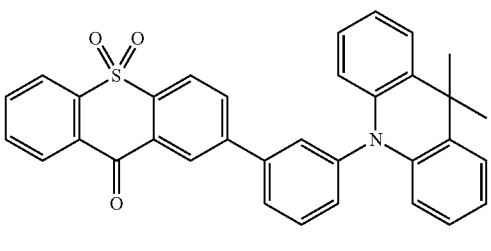

P31

Specific implementation steps are that:

the benzoic carbazole borate ester in the embodiment 15 is replaced with the equivalent amount of benzene-substituted acridine borate ester, other raw materials and steps are the same as that in the embodiment 15, thereby a white solid product of 0.737 g is obtained, and the yield is 78%. $C_{46}H_{33}NS$ M/S=631.23, theoretical values: 631.23 (100.0%), 632.24 (51.7%), 633.24 (13.5%), 633.23 (4.6%), 634.23 (2.3%), 634.24 (2.3%), 632.23 (1.2%). Elemental analysis: C, 87.44; H, 5.26; N, 2.22; S, 5.07.

Embodiment 32

This embodiment prepares the compound P32, a structural formula and a synthetic route thereof are shown as follows:

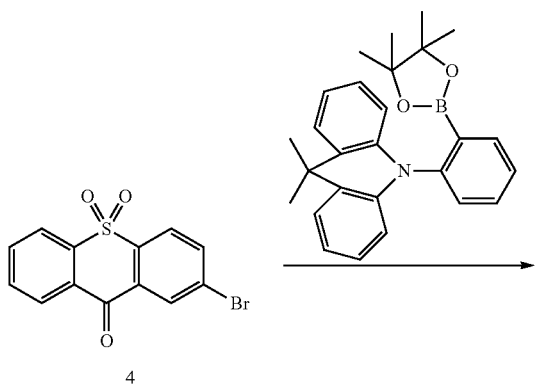

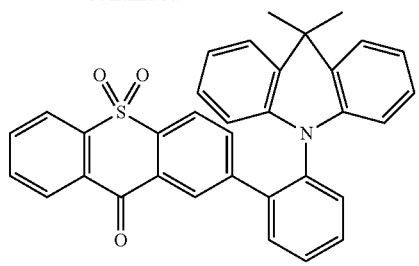

P32

Specific implementation steps are that:

the phenylcarbazole borate ester in the embodiment 15 is replaced with the equivalent amount of benzene-substituted acridine borate ester, the intermediate 3 is replaced with the equivalent amount of the intermediate 4, other raw materials and steps are the same as that in the embodiment 15, thereby a white solid product of 0.77 g is obtained, and the yield is 78%. $C_{46}H_{33}NO_2S$ M/S=663.22, theoretical values: 663.22 (100.0%), 664.23 (51.7%), 665.23 (13.9%), 665.22 (4.6%), 666.23 (2.5%), 666.22 (2.3%), 664.22 (1.2%). Elemental analysis: C, 83.23; H, 5.01; N, 2.11; O, 4.82; S, 4.83.

Embodiment 33

This embodiment prepares the compound P33, a structural formula and a synthetic route thereof are shown as follows:

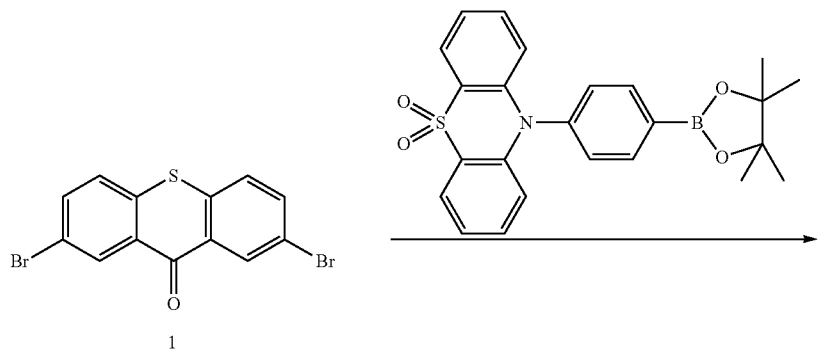

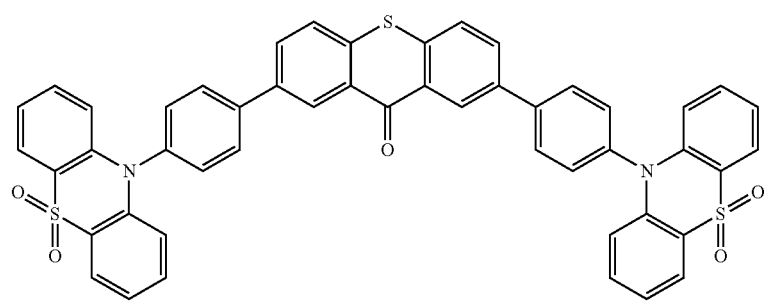

P33

Specific implementation steps are that:

the benzoic carbazole borate ester in the embodiment 9 is replaced with the equivalent amount of benzene-substituted phenothiazine-dioxide borate ester, other raw materials and steps are the same as that in the embodiment 9, thereby a white solid product of 1.10 g is obtained, and the yield is 77%. $C_{61}H_{38}N_2O_4S_3$ M/S=958.20, theoretical values: 958.20 (100.0%), 959.20 (71.1%), 960.21 (23.1%), 960.20 (16.3%), 961.20 (9.3%), 961.21 (6.2%), 962.20 (3.4%), 962.21 (1.2%). Elemental analysis: C, 76.38; H, 3.99; N, 2.92; O, 6.67; S, 10.03.

Embodiment 34

This embodiment prepares the compound P34, a structural formula and a synthetic route thereof are shown as follows:

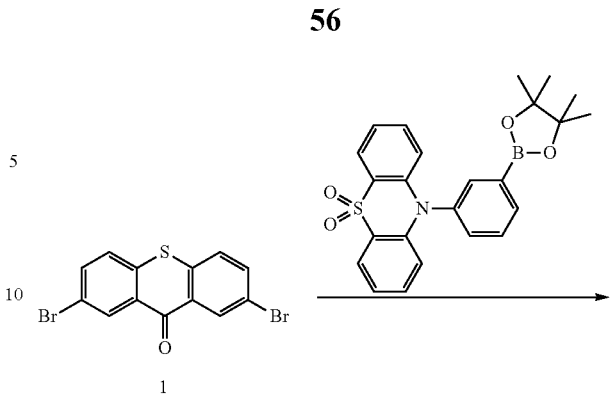

Specific implementation steps are that:

the benzoic carbazole borate ester in the embodiment 9 is replaced with the equivalent amount of benzene-substituted phenothiazine-dioxide borate ester, the intermediate 1 is replaced with the equivalent amount of the intermediate 2, other raw materials and steps are the same as that in the embodiment 9, thereby a white solid product of 1.13 g is obtained, and the yield is 76%. $C_{61}H_{38}N_2O_6S_3$ M/S=990.19, theoretical values: 990.19 (100.0%), 991.19 (71.2%), 992.20 (23.2%), 992.18 (13.3%), 993.19 (9.4%), 993.20 (6.5%), 994.19 (3.5%), 992.19 (3.4%), 994.20 (1.3%). Elemental analysis: C, 73.92; H, 3.86; N, 2.83; O, 9.69; S, 9.71.

Embodiment 35

This embodiment prepares the compound P35, a structural formula and a synthetic route thereof are shown as follows:

Specific implementation steps are that:

the benzoic carbazole borate ester in the embodiment 9 is replaced with the equivalent amount of benzene-substituted phenothiazine-dioxide borate ester, other raw materials and steps are the same as that in the embodiment 9, thereby a white solid product of 1.07 g is obtained, and the yield is 75%. $C_{61}H_{38}N_2O_4S_3$ M/S=958.20, theoretical values: 958.20 (100.0%), 959.20 (71.1%), 960.21 (23.1%), 960.20 (16.3%), 961.20 (9.3%), 961.21 (6.2%), 962.20 (3.4%), 962.21 (1.2%). Elemental analysis: C, 76.38; H, 3.99; N, 2.92; O, 6.67; S, 10.03.

Embodiment 36

This embodiment prepares the compound P36, a structural formula and a synthetic route thereof are shown as follows:

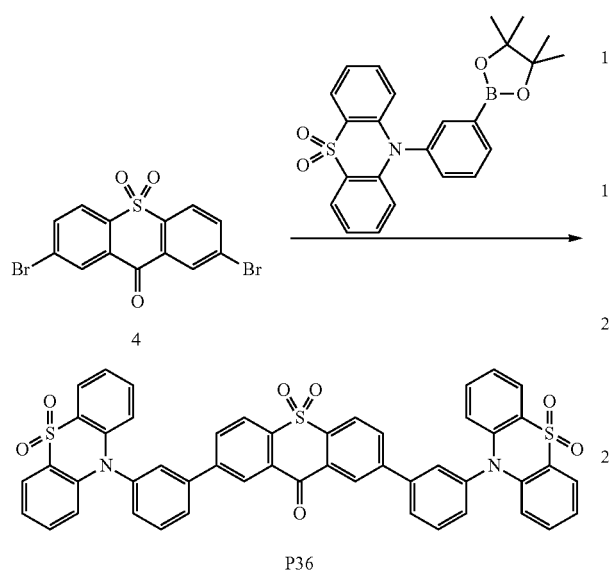

P36

Specific implementation steps are that:

the benzoic carbazole borate ester in the embodiment 32 is replaced with the equivalent amount of benzene-substituted phenothiazine-dioxide borate acid ester, the intermediate 3 in the embodiment 32 is replaced with the equivalent amount of the intermediate 4, other raw materials and steps are the same as that in the embodiment 32, thereby a white solid product of 1.10 g is obtained, and the yield is 74%. $C_{61}H_{38}N_2O_6S_3$ M/S=990.19, theoretical values: 990.19 (100.0%), 991.19 (71.2%), 992.20 (23.2%), 992.18 (13.3%), 993.19 (9.4%), 993.20 (6.5%), 994.19 (3.5%), 992.19 (3.4%), 994.20 (1.3%). Elemental analysis: C, 73.92; H, 3.86; N, 2.83; O, 9.69; S, 9.71.

Embodiment 37

This embodiment prepares the compound P37, a structural formula and a synthetic route thereof are shown as follows:

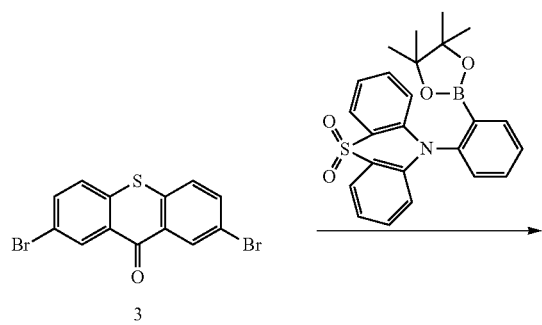

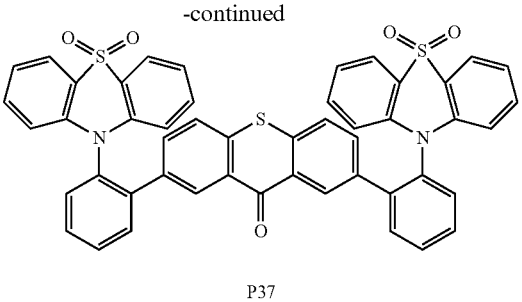

P37

Specific implementation steps are that:

the benzoic carbazole borate ester in the embodiment 9 is replaced with the equivalent amount of benzene-substituted phenothiazine-dioxide borate ester, other raw materials and steps are the same as that in the embodiment 9, thereby a white solid product of 1.06 g is obtained, and the yield is 74%. $C_{61}H_{38}N_2O_4S_3$ M/S=958.20, theoretical values: 958.20 (100.0%), 959.20 (71.1%), 960.21 (23.1%), 960.20 (16.3%), 961.20 (9.3%), 961.21 (6.2%), 962.20 (3.4%), 962.21 (1.2%). Elemental analysis: C, 76.38; H, 3.99; N, 2.92; O0, 6.67; S, 10.03.

Embodiment 38

This embodiment prepares the compound P38, a structural formula and a synthetic route thereof are shown as follows:

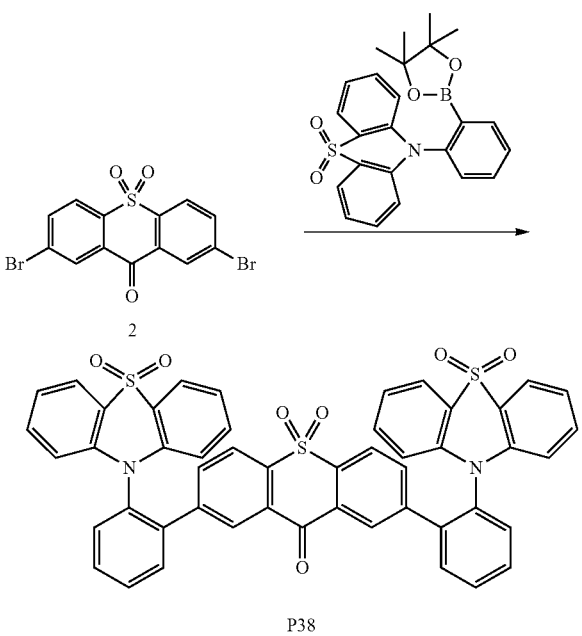

P38

Specific implementation steps are that:

the benzoic carbazole borate ester in the embodiment 9 is replaced with the equivalent amount of benzene-substituted phenothiazine-dioxide borate ester, the intermediate 1 is replaced with the equivalent amount of the intermediate 2, other raw materials and steps are the same as that in the embodiment 9, thereby a white solid product of 1.07 g is obtained, and the yield is 72%. $C_{61}H_{38}N_2O_6S_3$ M/S=990.19, theoretical values: 990.19 (100.0%), 991.19 (71.2%), 992.20 (23.2%), 992.18 (13.3%), 993.19 (9.4%), 993.20 (6.5%), 994.19 (3.5%), 992.19 (3.4%), 994.20 (1.3%). Elemental analysis: C, 73.92; H, 3.86; N, 2.83; O, 9.69; S, 9.71.

Embodiment 39

This embodiment prepares the compound P39, a structural formula and a synthetic route thereof are shown as follows:

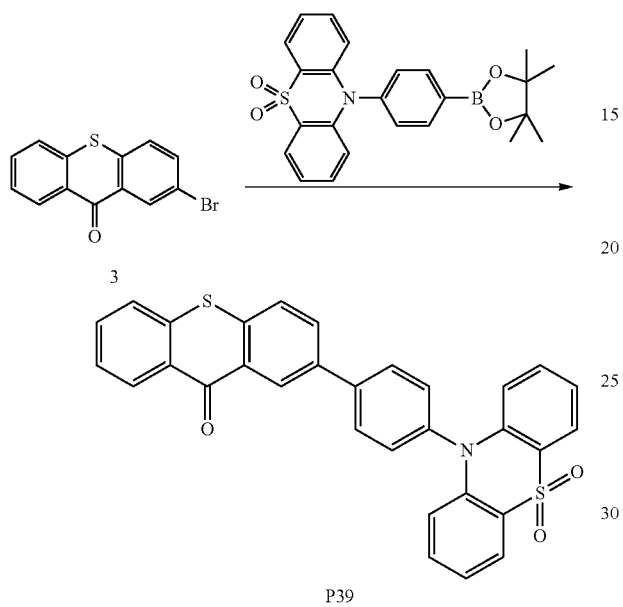

P39

Specific implementation steps are that:

the benzoic carbazole borate ester in the embodiment 15 is replaced with the equivalent amount of benzene-substituted phenothiazine borate ester, other raw materials and steps are the same as that in the embodiment 15, thereby a white solid product of 0.76 g is obtained, and the yield is 78%. $C_{43}H_{27}NO_2S_2$ M/S=653.15, theoretical values: 653.15 (100.0%), 654.15 (50.3%), 655.16 (11.4%), 655.14 (8.9%), 656.15 (4.5%), 656.16 (1.9%), 655.15 (1.3%), 657.15 (1.1%). Elemental analysis: C, 78.99; H, 4.16; N, 2.14; O, 4.89; S, 9.81.

Embodiment 40

This embodiment prepares the compound P40, a structural formula and a synthetic route thereof are shown as follows:

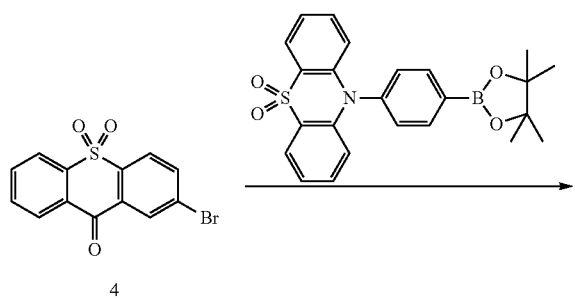

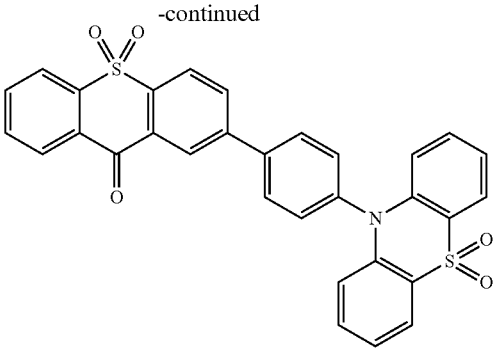

P40

Specific implementation steps are that:

the benzoic carbazole borate ester in the embodiment 15 is replaced with the equivalent amount of benzene-substituted phenothiazine borate ester, the intermediate 3 is replaced with the equivalent amount of the intermediate 4, other raw materials and steps are the same as that in the embodiment 15, thereby a white solid product of 0.76 g is obtained, and the yield is 74%. $C_{43}H_{27}NO_4S_2$ M/S=685.14, theoretical values: 685.14 (100.0%), 686.14 (50.3%), 687.14 (12.9%), 687.13 (8.9%), 688.14 (4.5%), 688.15 (2.2%), 689.14 (1.1%), elemental analysis: C, 75.31; H, 3.97; N, 2.04; O, 9.33; S, 9.35.

Embodiment 41

This embodiment prepares the compound P41, a structural formula and a synthetic route thereof are shown as follows:

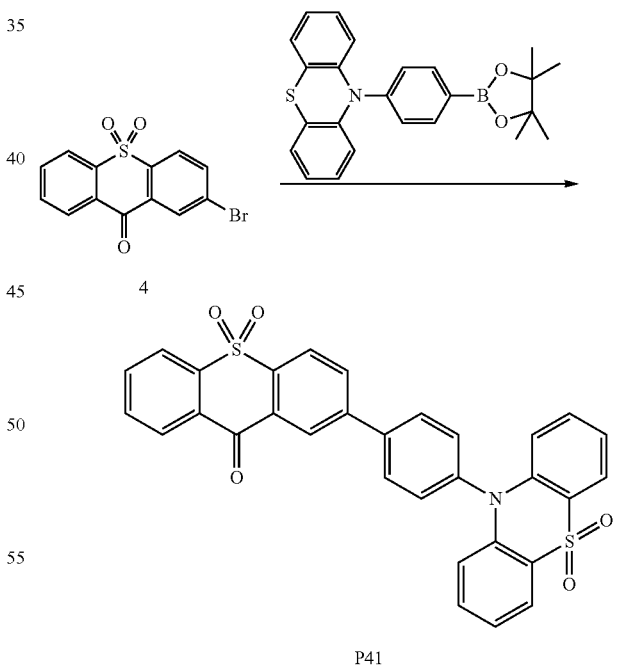

P41

Specific implementation steps are that:

the benzoic carbazole borate ester in the embodiment 15 is replaced with the equivalent amount of benzene-substituted phenothiazine borate ester, the intermediate 3 is replaced with the equivalent amount of the intermediate 4, other raw materials and steps are the same as that in the embodiment 15, thereby a white solid product of 0.72 g is obtained, and the yield is 74%. $C_{43}H_{27}NO_2S_2$ M/S=653.15, theoretical values: 653.15 (100.0%), 654.15 (50.3%), 655.16 (11.4%), 655.14 (8.9%), 656.15 (4.5%), 656.16 (1.9%), 655.15 (1.3%), 657.15 (1.1%), elemental analysis: C, 78.99; H, 4.16; N, 2.14; O, 4.89; S, 9.81.

Embodiment 42

This embodiment prepares the compound P42, a structural formula and a synthetic route thereof are shown as follows:

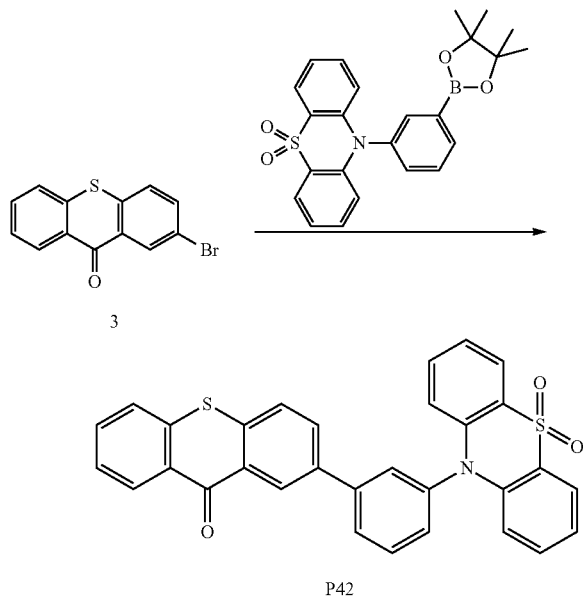

Specific implementation steps are that:
the benzoic carbazole borate ester in the embodiment 15 is replaced with the equivalent amount of benzene-substituted phenothiazine borate ester, other raw materials and steps are the same as that in the embodiment 15, thereby a white solid product of 0.74 g is obtained, and the yield is 72%. $C_{43}H_{27}NO_4S_2$ M/S=685.14, theoretical values: 685.14 (100.0%), 686.14 (50.3%), 687.14 (12.9%), 687.13 (8.9%), 688.14 (4.5%), 688.15 (2.2%), 689.14 (1.1%), elemental analysis: C, 75.31; H, 3.97; N, 2.04; O, 9.33; S, 9.35.

Embodiment 43

This embodiment prepares the compound P43, a structural formula and a synthetic route thereof are shown as follows:

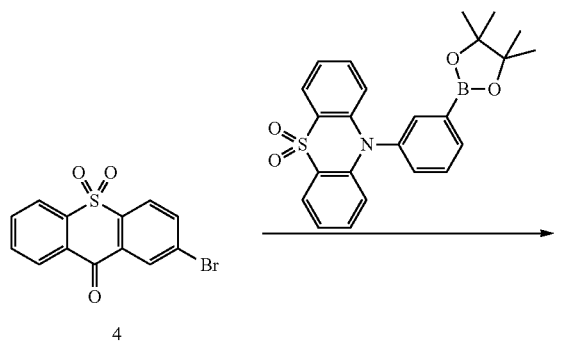

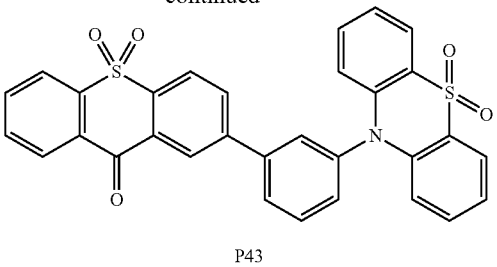

P43

Specific implementation steps are that:
the benzoic carbazole borate ester in the embodiment 15 is replaced with the equivalent amount of benzene-substituted phenothiazine borate ester, the intermediate 3 is replaced with the equivalent amount of the intermediate 4, other raw materials and steps are the same as that in the embodiment 15, thereby a white solid product of 0.72 g is obtained, and the yield is 74%. $C_{43}H_{27}NO_2S_2$ M/S=653.15, theoretical values: 653.15 (100.0%), 654.15 (50.3%), 655.16 (11.4%), 655.14 (8.9%), 656.15 (4.5%), 656.16 (1.9%), 655.15 (1.3%), 657.15 (1.1%), elemental analysis: C, 78.99; H, 4.16; N, 2.14; O, 4.89; S, 9.81.

Embodiment 44

This embodiment prepares the compound P44, a structural formula and a synthetic route thereof are shown as follows:

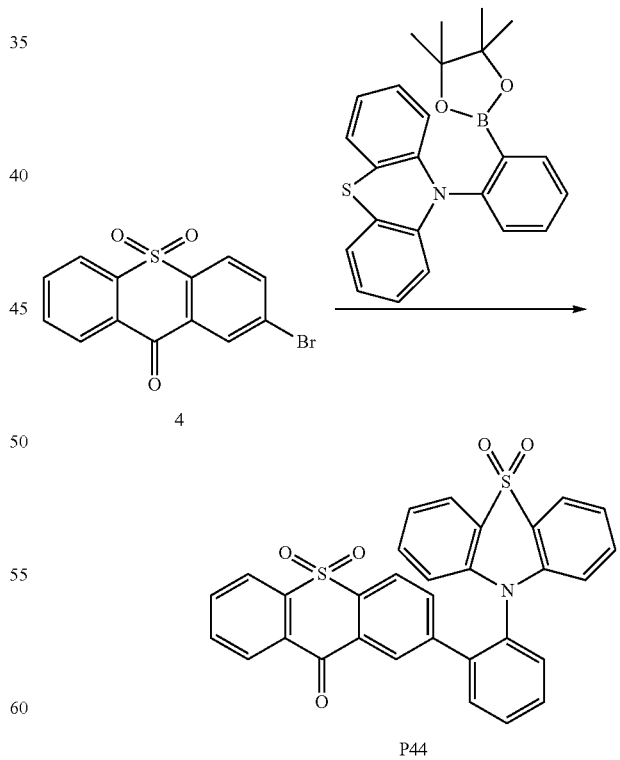

Specific implementation steps are that:
the benzoic carbazole borate ester in the embodiment 15 is replaced with the equivalent amount of benzene-substituted phenothiazine borate ester, the intermediate 3 is replaced with the equivalent amount of the intermediate 4, other raw materials and steps are the same as that in the embodiment 15, thereby a white solid product of 0.78 g is obtained, and the yield is 76%. $C_{43}H_{27}NO_4S_2$ M/S=685.14, theoretical values: 685.14 (100.0%), 686.14 (50.3%), 687.14 (12.9%), 687.13 (8.9%), 688.14 (4.5%), 688.15 (2.2%), 689.14 (1.1%), elemental analysis: C, 75.31; H, 3.97; N, 2.04; O, 9.33; S, 9.35.

The above mentioned thioxanthone aromatic amine compounds each have single structure, determinate molecular weight, and better solubility and film-forming property, and also have low biochemical temperature and decomposition temperature, stable film morphology; conjugation length and light emission color of the material can be adjusted by changing the connected chemical structure, and moreover, physical characteristics and performance of photoelectric devices based on the thioxanthone aromatic amine compounds can be further improved by changing the modified groups contained on the aromatic structure.

Figure 7:
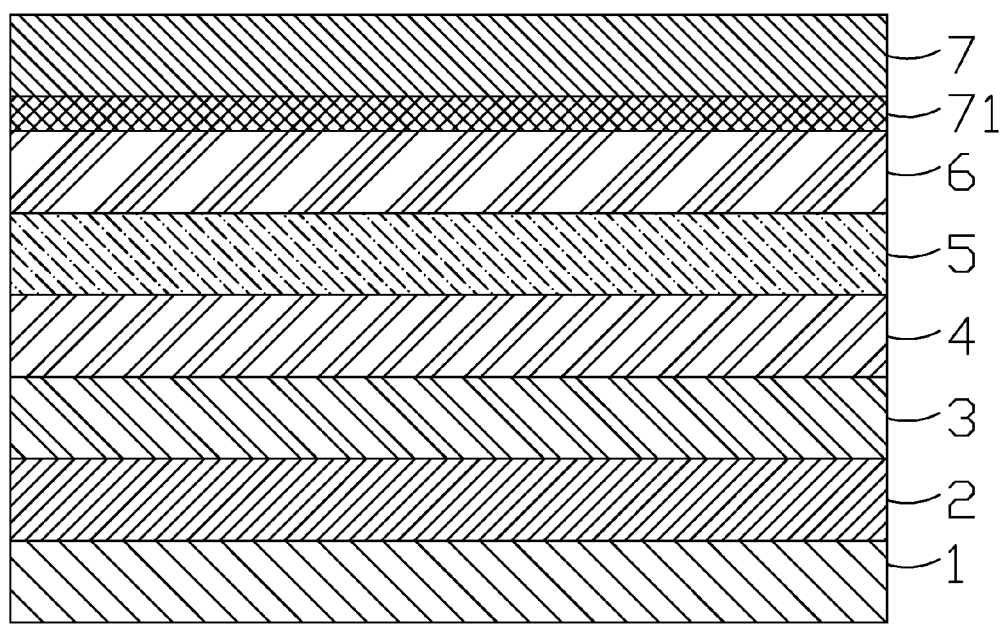
FIG. 7 is a structural schematic view of an organic light emitting device of the invention.
Figure 8:
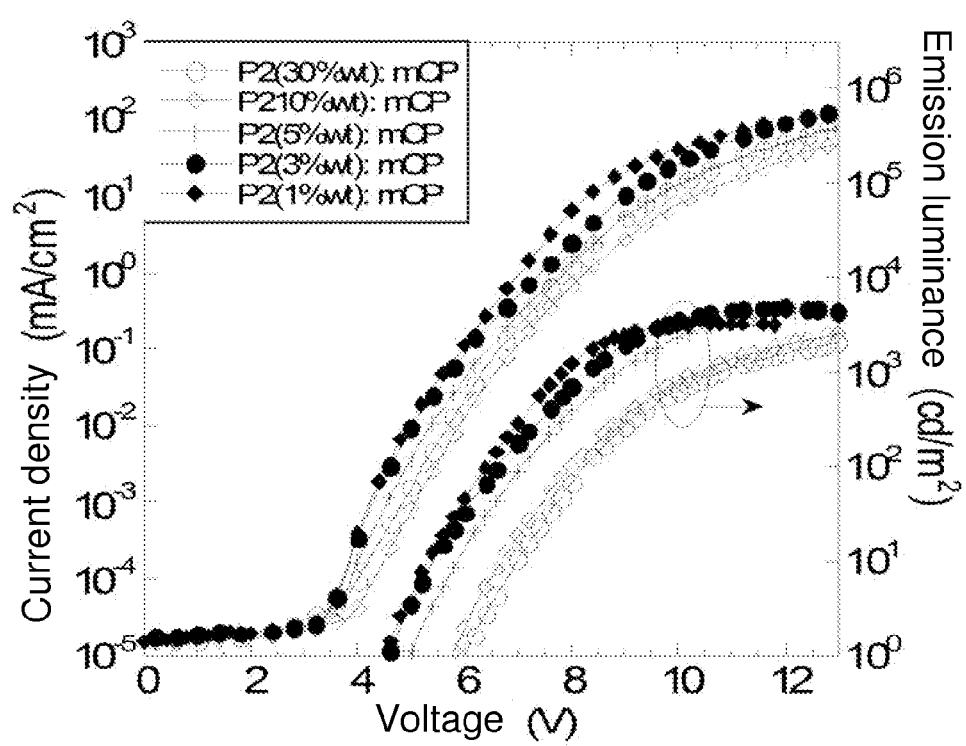
FIG. 8 is a current density-emission luminance-voltage relationship curve graph of organic light emitting devices doped with different concentrations of thioxanthone aromatic amine compound P2 of the invention.
Figure 9:
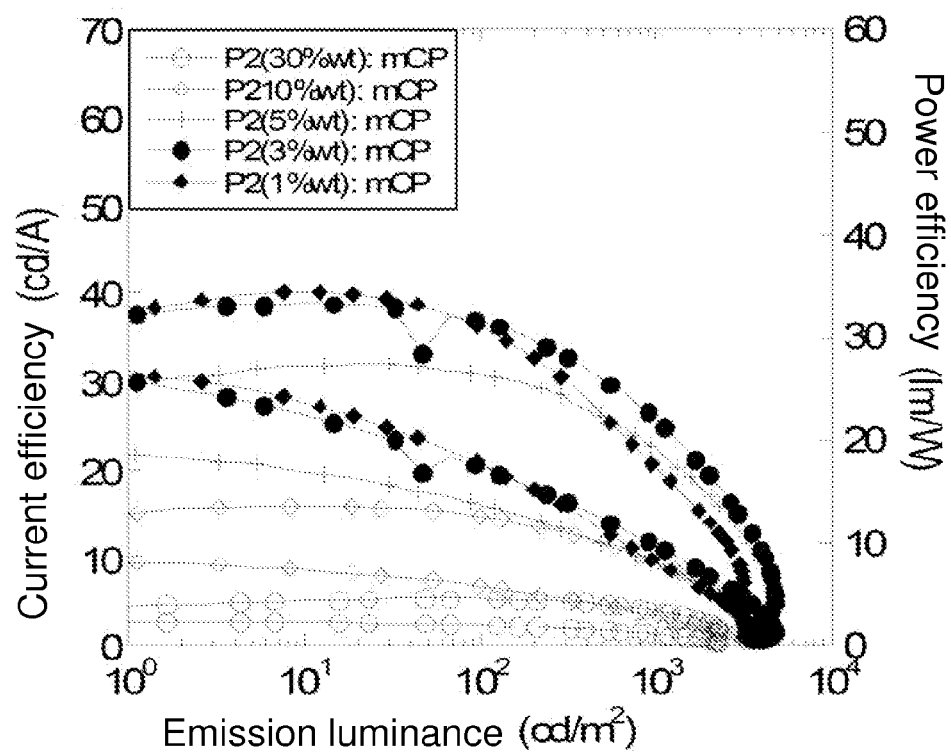
FIG. 9 is an emission luminance-current efficiency-power efficiency relationship curve graph of organic light emitting devices doped with different concentrations of thioxanthone aromatic amine compound P2 of the invention.
Figure 10:
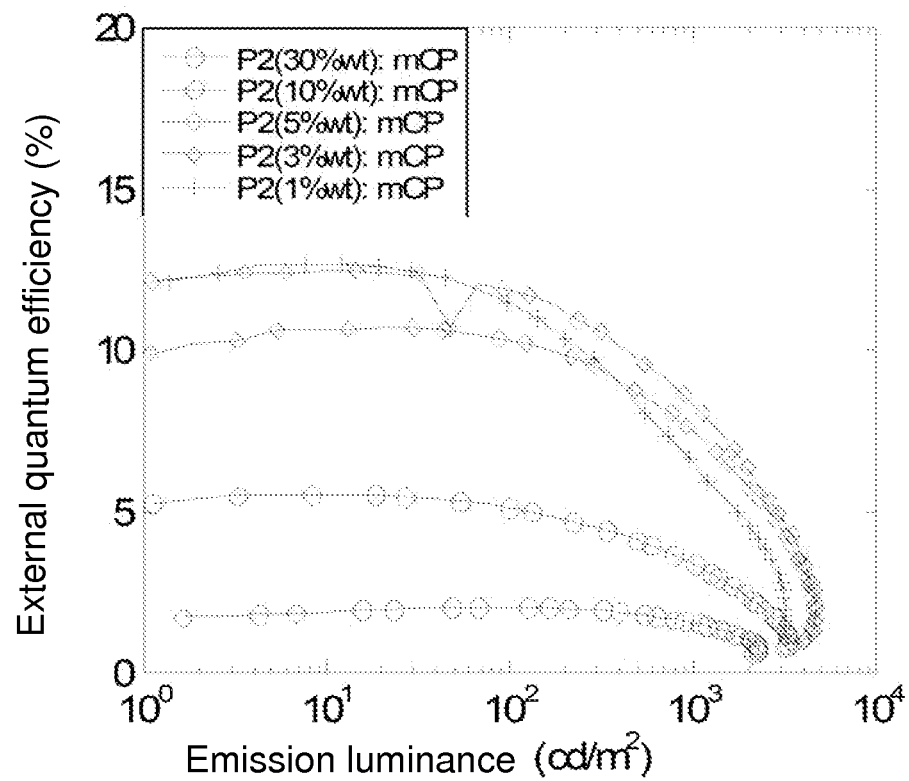
FIG. 10 is an emission luminance-external quantum efficiency relationship curve graph of organic light emitting devices doped with different concentrations of thioxanthone aromatic amine compound P2 of the invention.
Figure 11:
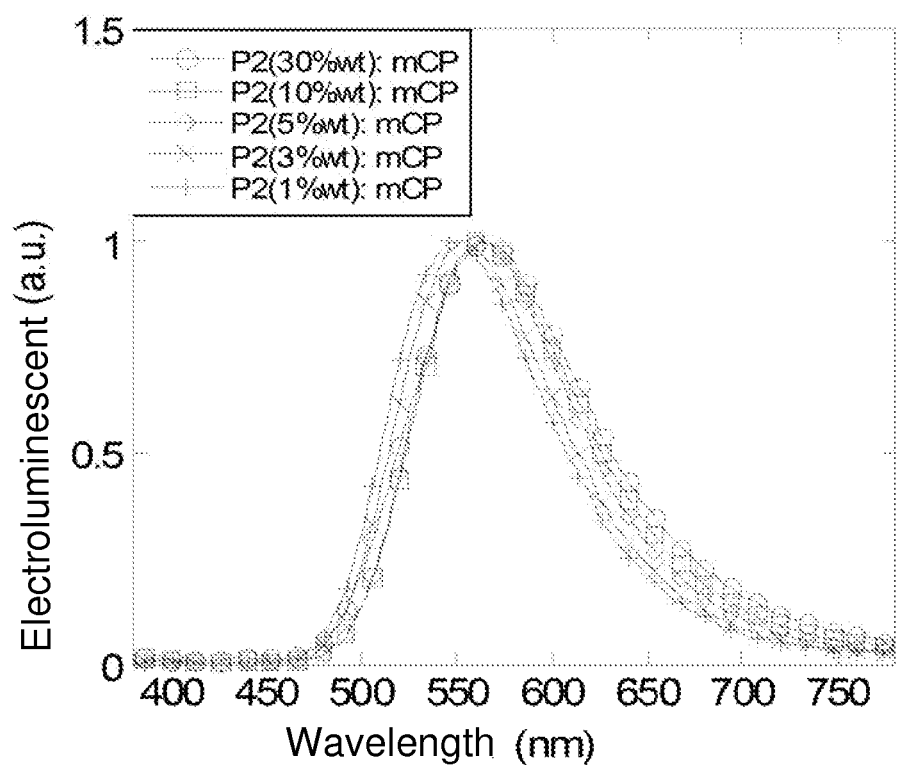
FIG. 11 is an emission spectra view of organic light emitting devices doped with different concentrations of thioxanthone aromatic amine compound P2 of the invention.

Referring to FIG. 7, the invention also provides an organic light emitting device including a substrate 1, an anode 2 formed on the substrate 1, a hole injection layer 3 formed on the anode 2, a hole transport layer 4 formed on the hole injection layer 3, multiple light-emitting layers 5 formed on the hole transport layer 4, an electron transport layer 6 formed on the multiple light-emitting layers 5, and a cathode 7 formed on the electron transport layer 6. A material of the multiple light-emitting layers 5 is one or more of the above mentioned thioxanthone aromatic amine compounds.

Specifically, a material of the anode 2 is indium tin oxide, an electron injection layer 71 is provided between the cathode 7 and the electron transport layer 7, a material of the cathode 7 is aluminum, a material of the electron injection layer 71 is lithium fluoride.

Specifically, a thickness of the anode 2 is 95 nm, a thickness of the hole injection layer 3 is 5 nm, a thickness of the hole transport layer 4 is 20 nm, a thickness of the light-emitting layers 5 is 35 nm, a thickness of electron transport layer 6 is 55 nm, a thickness of the cathode 7 is greater than 80 nm, and a thickness of the electron injection layer 71 is 1 nm.

Specifically, a material of the hole injection layer 3 is 2,3,6,7,10,11-hexacyano-1,4,5,8,9,12-hexaazatriphenylene-hexacabonitrile (HAT-CN), and its structural formula is:

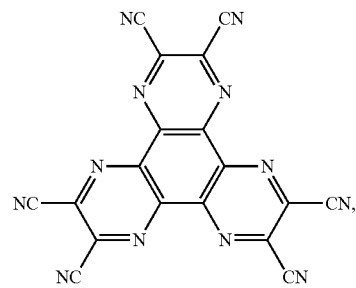 [SMILES: N#Cc1nc2c3nc(C#N)c(C#N)nc3c3nc(C#N)c(C#N)nc3c2nc1C#N]

a material of the hole transport layer 4 is 4-(2-thiazoly-lazo)-phenyl-2-glycine (TAPC), and its structural formula is:

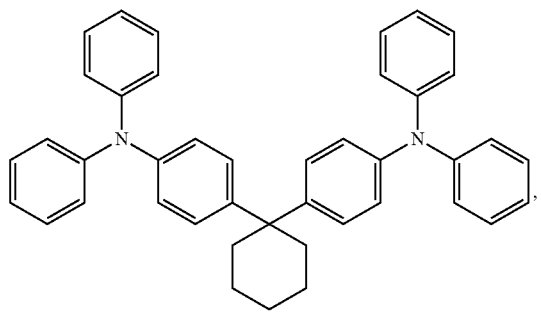 [SMILES: c1ccc(N(c2ccccc2)c2ccc(C3(c4ccc(N(c5ccccc5)c5ccccc5)cc4)CCCCC3)cc2)cc1]

a material of the light-emitting layers 5 is 1,3-di-carbazolyl benzene (mCP) doped with thioxanthone aromatic amine compound P2, a structural formula of the 1,3-di-carbazolyl benzene (mCP) is:

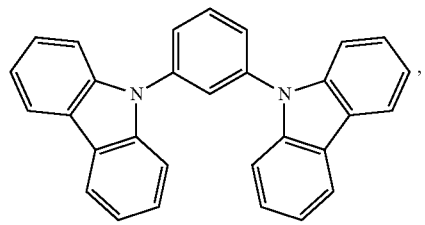 [SMILES: c1cc(-n2c3ccccc3c3ccccc32)cc(-n2c3ccccc3c3ccccc32)c1]

a structural formula of the thioxanthone aromatic amine compound P2 is:

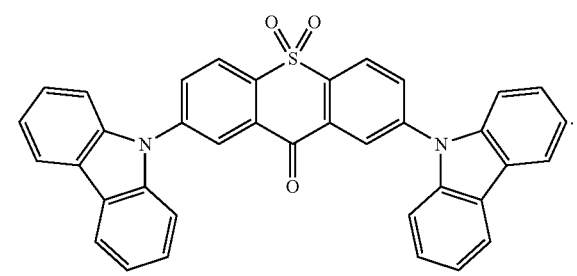

P2

A material of the electron transport layer 6 is 1,3,5-tri[(3-pyridyl)-3-phenyl] benzene (TmPyPB), and its structural formula is:

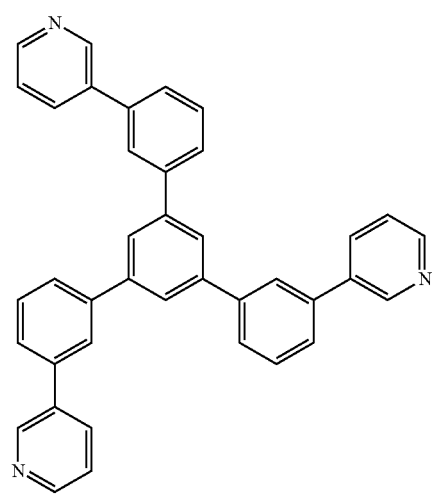 [SMILES: c1cncc(-c2cccc(-c3cc(-c4cccc(-c5cccnc5)c4)cc(-c4cccc(-c5cccnc5)c4)c3)c2)c1]

A preparation process of the organic light emitting device is as follows: ultrasonic processing the indium tin oxide (ITO) transparent conductive glass in a cleaning agent, then washing with deionized water, ultrasonic degreasing in a mixed solvent of acetone/ethanol, after that baking under a clean environment to remove moisture completely, and then cleaning with ultraviolet light and ozone, bombarding with low energy cations to obtain the anode 2, placing the anode 2 in a vacuum chamber, evacuating to $1\times10^{-5}\sim9\times10^{-3}$ Pa, sequentially evaporating the hole injection layer 3, the hole transport layer 4, the multiple light-emitting layers 5, the electron transport layer 6, the electron injection layer 71 and the cathode 7 on the anode 2, and thereby the organic electroluminescent device of the present embodiment is obtained as a result.

Performance datum of the above mentioned organic electroluminescent device are shown in Table 1. A light-emitting layer of device A is 1,3-di-carbazolyl benzene (mCP) doped with 1±0.2% wt the thioxanthone aromatic amine compound P2, a light-emitting layer of device B is 1,3-di-carbazolyl benzene (mCP) doped with 3±0.2% wt the thioxanthone aromatic amine compound P2, a light-emitting layer of device C is 1,3-di-carbazolyl benzene (mCP) doped with 5±1% wt the thioxanthone aromatic amine compound P2, a light-emitting layer of device D is 1,3-di-carbazolyl benzene (mCP) doped with 10±1% wt the thioxanthone aromatic amine compound P2, a light-emitting layer of device E is 1,3-di-carbazolyl benzene (mCP) doped with 30±2% wt the thioxanthone aromatic amine compound P2, and the turn-on voltage represents a driving voltage when the luminance is 1 cd/m².

and also has low biochemical temperature and decomposition temperature; conjugation length and light-emitting color of the material can be adjusted by changing of the connected chemical structures, and moreover, physical characteristics and performance of photoelectric device based on the thioxanthone aromatic amine compound can be further improved by changing the modified groups contained on aromatic structure. The organic light emitting device of the invention can achieve high luminous efficiency and stability resulting from the material of its light-emitting layer adopting the thioxanthone aromatic amine compound.

Based on the above description, the ordinary skill in the art may made other various changes and modifications according to the technical solutions and the technical concept of the invention, and all the changes and modifications should belong to the scope of protection of the appended claims of the invention.

What is claimed is:

1. A thioxanthone aromatic amine compound comprising: a compound expressed by formula (I):

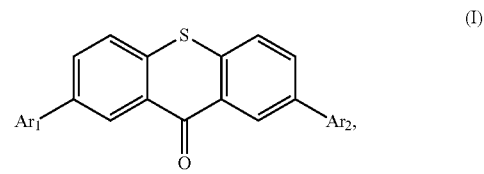

(I)

where $Ar_1$ and $Ar_2$ each are selected from the ammonia compounds with the structures respectively expressed by the formula (III) to the formula (VII), and the $Ar_1$ and the $Ar_2$ having the same structure or having different structures,

TABLE 1

Performance datum summary of organic electroluminescent devices of the invention

| Device number | Turn-on voltage (V) | Maximum efficiency | | At the luminance of 100 cd/m² | | | | At the luminance of 1000 cd/m² | | | |
|---|---|---|---|---|---|---|---|---|---|---|---|
| | | Current efficiency (cd/A) | External quantum efficiency (%) | Voltage (V) | Current efficiency (cd/A) | Power efficiency (lm/W) | Color coordinates | Voltage (V) | Current efficiency (cd/A) | Power efficiency (lm/W) | Color coordinates |
| A | 4.5 | 40.2 | 12.7 | 6.4 | 36.4 | 17.8 | (0.397, 0.564) | 7.8 | 20.7 | 8.32 | (0.402, 0.555) |
| B | 4.6 | 38.8 | 12.5 | 6.6 | 37.0 | 17.6 | (0.415, 0.556) | 8.2 | 26.6 | 10.2 | (0.417, 0.554) |
| C | 5.0 | 31.9 | 10.7 | 7.0 | 31.0 | 13.9 | (0.441, 0.540) | 8.8 | 22.8 | 8.13 | (0.440, 0.540) |
| D | 5.8 | 15.8 | 5.53 | 8.0 | 14.7 | 5.75 | (0.450, 0.531) | 10.4 | 9.49 | 2.87 | (0.450, 0.529) |
| E | 6.0 | 5.40 | 2.03 | 8.2 | 5.34 | 2.04 | (0.460, 0.518) | 10.8 | 3.96 | 1.15 | (0.475, 0.506) |

FIG. 8, FIG. 9, FIG. 10 and FIG. 11 are respectively a current density-emission luminance-voltage relationship curve graph, an emission luminance-current efficiency-power efficiency relationship curve graph, an emission brightness-external quantum efficiency relationship curve graph and an emission spectra view of organic light emitting device of the invention doped with different concentrations of thioxanthone aromatic amine compound P2.

The above organic light emitting devices, owing to the material of its light-emitting layers adopting the thioxanthone aromatic amine compound, can achieve high luminous efficiency and stability.

In summary, the thioxanthone aromatic amine compound of the invention has single structure, determinate molecular weight, and has better solubility and film-forming property,

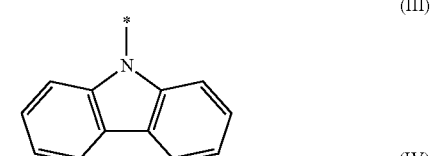

(III)

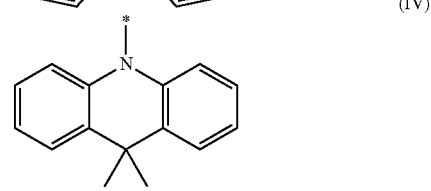

(IV)

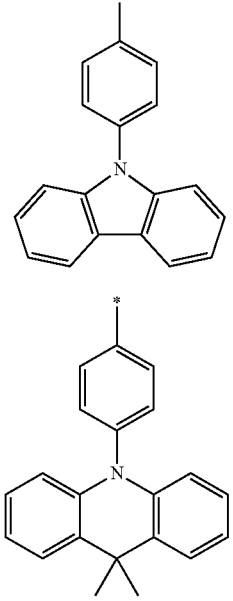
(V)
(VI)
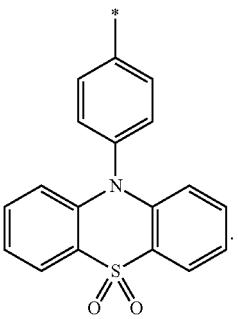
(VII)
2. The thioxanthone aromatic amine compound as claimed in claim 1, wherein the thioxanthone aromatic amine compound is one selected from the group consisting of compounds P1, P5, P9, P11, P13, P21, P23, P25, P33, P35 and P37 respectively having the following structural formulas:
P1
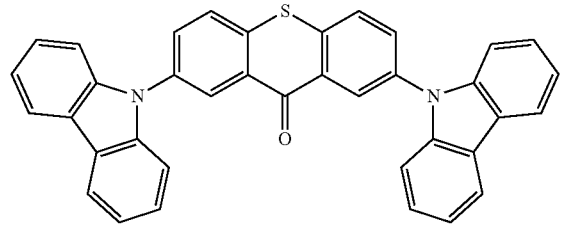
P5
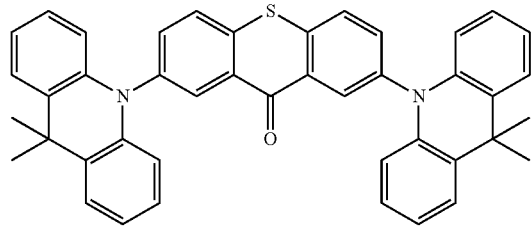
P9
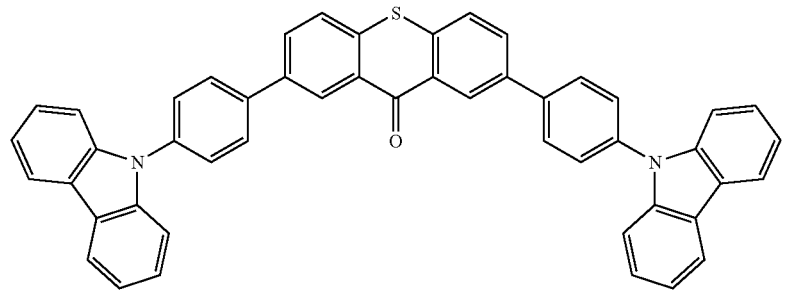
P11
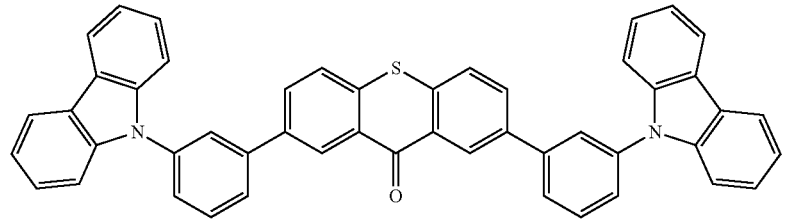
P13
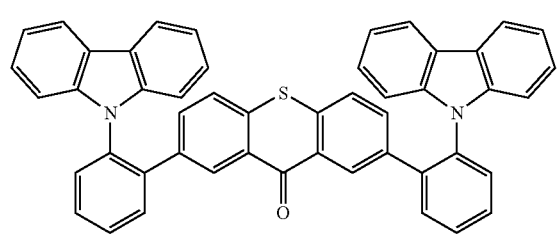
P14
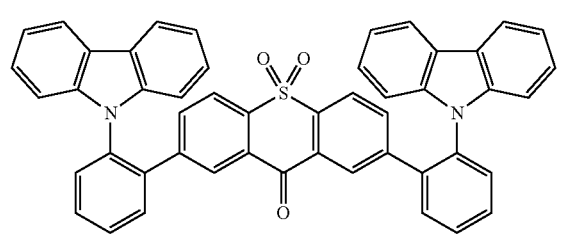

-continued

P21 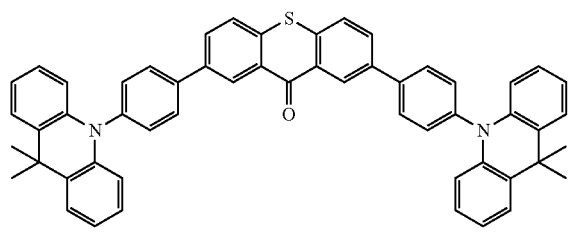

P23 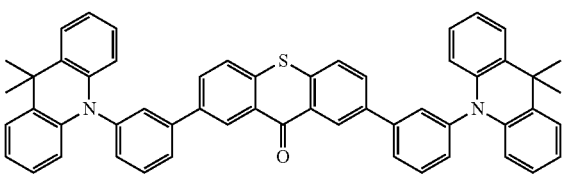

P25 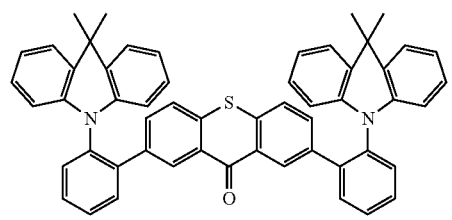

P33 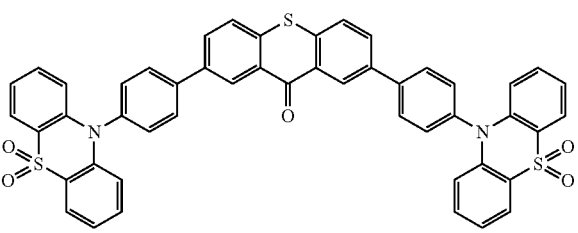

P35 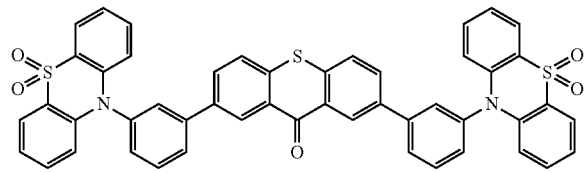

P37 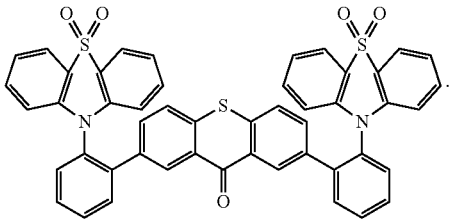

3. An organic light emitting device comprising: a substrate, an anode formed on the substrate, a hole injection layer formed on the anode, a hole transport layer formed on the hole injection layer, a plurality of light-emitting layers formed on the hole transport layer, an electron transport layer formed on the plurality of light-emitting layers, and a cathode formed on the electron transport layer; a material of the plurality of the light-emitting layers is one or more the thioxanthone aromatic amine compounds as claimed in claim 1.

4. The organic light emitting device as claimed in claim 3, wherein a material of the anode is indium tin oxide, an electron injection layer is provided between the cathode and the electron transport layer, a material of the cathode is aluminum, and a material of the electron injection layer is lithium fluoride.

5. The organic light emitting device as claimed in claim 4, wherein a thickness of the anode is 95 nm, a thickness of the hole injection layer is 5 nm, a thickness of the hole transport layer is 20 nm, a thickness of the plurality of light-emitting layers is 35 nm, a thickness of electron transport layer is 55 nm, a thickness of the cathode is greater than 80 nm, and a thickness of the electron injection layer is 1 nm.

6. The organic light emitting device as claimed in claim 3, wherein a material of the hole injection layer is 2,3,6,7,10,11-hexacyano-1,4,5,8,9,12-hexaazatriphenylenehexacabonitrile (HAT-CN) whose structural formula is:

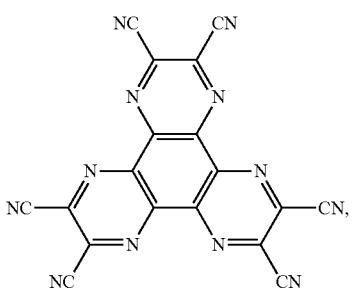 [SMILES: N#Cc1nc2c3nc(C#N)c(C#N)nc3c3nc(C#N)c(C#N)nc3c2nc1C#N]

a material of the hole transport layer is 4-(2-thiazolylazo)-phenyl-2-glycine (TAPC) whose structural formula is:

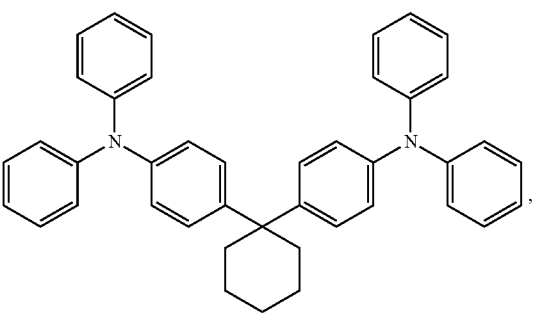 [SMILES: c1ccc(N(c2ccccc2)c2ccc(C3(c4ccc(N(c5ccccc5)c5ccccc5)cc4)CCCCC3)cc2)cc1]

a material of the plurality of light-emitting layers is 1,3-di-carbazolyl benzene (mCP) doped with a thioxanthone aromatic amine compound P2, a structural formula of the 1,3-di-carbazolyl benzene (mCP) is

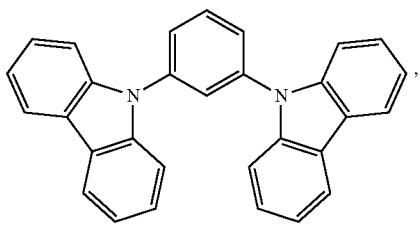 [SMILES: c1cc(-n2c3ccccc3c3ccccc32)cc(-n2c3ccccc3c3ccccc32)c1]

a structural formula of the thioxanthone aromatic amine compound P2 is:

P2

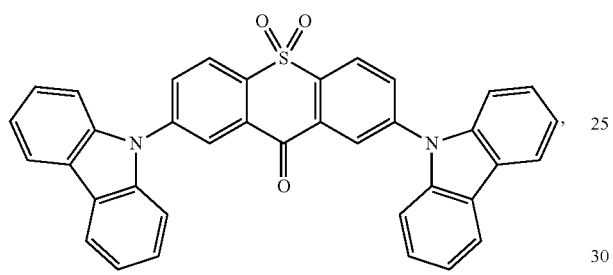

a material of the electron transport layer is 1,3,5-tri[(3-pyridyl)-3-phenyl] benzene (TmPyPB) whose structural formula is:

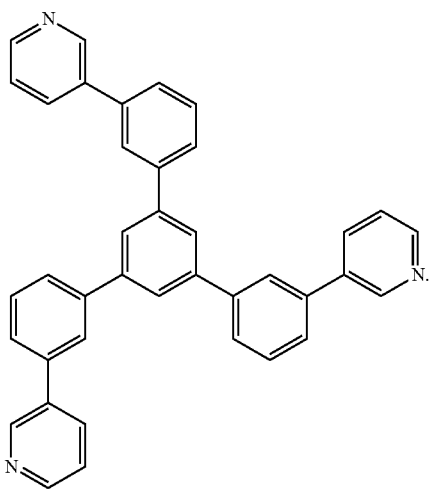 [SMILES: c1cncc(-c2cccc(-c3cc(-c4cccc(-c5cccnc5)c4)cc(-c4cccc(-c5cccnc5)c4)c3)c2)c1]

7. An organic light emitting device comprising: a substrate, an anode formed on the substrate, a hole injection layer formed on the anode, a hole transport layer formed on the hole injection layer, a plurality of light-emitting layers formed on the hole transport layer, an electron transport layer formed on the plurality of light-emitting layers, and a cathode formed on the electron transport layer; a material of the plurality of the light-emitting layers is one or more thioxanthone aromatic amine compounds as claimed in claim 1;
wherein, a material of the anode is indium tin oxide, an electron injection layer is provided between the cathode and the electron transport layer, a material of the cathode is aluminum, a material of the electron injection layer is lithium fluoride;

wherein, a material of the hole injection layer is 2,3,6,7,10,11-hexacyano-1,4,5,8,9,12-hexaazatriphenylene-hexacabonitrile (HAT-CN) whose structural formula is:

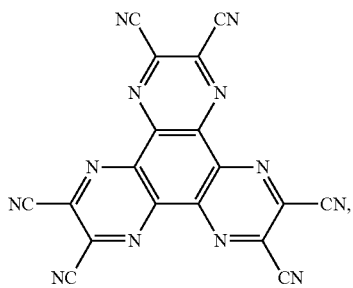 [SMILES: N#Cc1nc2c3nc(C#N)c(C#N)nc3c3nc(C#N)c(C#N)nc3c2nc1C#N]

a material of the hole transport layer is 4-(2-thiazolylazo)-phenyl-2-glycine (TAPC) whose structural formula is:

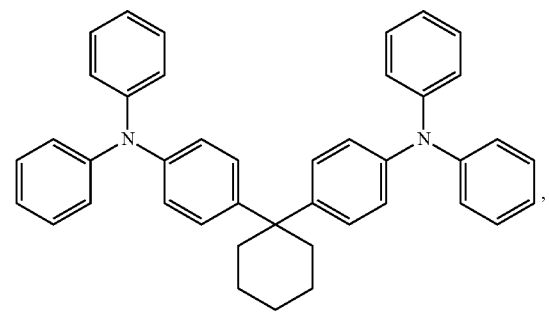 [SMILES: c1ccc(N(c2ccccc2)c2ccc(C3(c4ccc(N(c5ccccc5)c5ccccc5)cc4)CCCCC3)cc2)cc1]

a material of the luminescent layer is 1,3-di-carbazolyl benzene (mCP) doped with a thioxanthone aromatic amine compound P2, a structural formula of the 1,3-di-carbazolyl benzene (mCP) is:

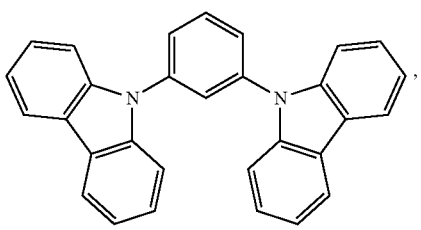 [SMILES: c1cc(-n2c3ccccc3c3ccccc32)cc(-n2c3ccccc3c3ccccc32)c1]

a structural formula of the thioxanthone aromatic amine compound P2 is:

P2

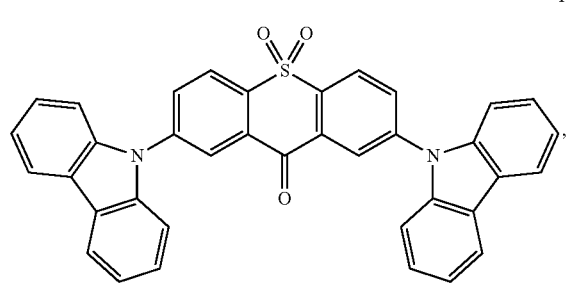

a material of the electron transport layer is 1,3,5-tri[(3-pyridyl)-3-phenyl] benzene (TmPyPB) whose structural formula is:

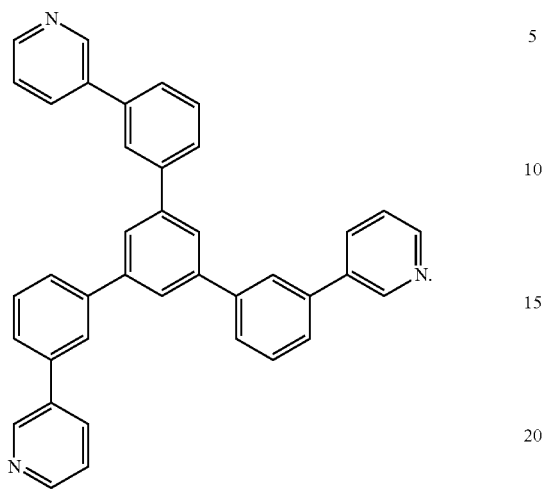

8. The organic light emitting device as claimed in claim 7, wherein a thickness of the anode is 95 nm, a thickness of the hole injection layer is 5 nm, a thickness of the hole transport layer is 20 nm, a thickness of the plurality of light-emitting layers is 35 nm, a thickness of electron transport layer is 55 nm, a thickness of the cathode is greater than 80 nm, and a thickness of the electron injection layer is 1 nm.

* * * * *